US010470518B1

(12) United States Patent
Walsh et al.

(10) Patent No.: US 10,470,518 B1
(45) Date of Patent: Nov. 12, 2019

(54) SYSTEMS AND METHODS FOR ADJUSTING VARIABLE GEOMETRY, HEIGHT, WEIGHT DISTRIBUTION IN FOOTWEAR DEVICES AND EQUIPMENT

(71) Applicant: Alliance Design and Development Group, Inc., Matawan, NJ (US)

(72) Inventors: Robert Walsh, Matawan, NJ (US); Peter B. Tarlton, Reading (GB)

(73) Assignee: Alliance Deign and Development Group, Inc., Matawan, NJ (US)

( * ) Notice: Subject to any disclaimer, the term of this patent is extended or adjusted under 35 U.S.C. 154(b) by 223 days.

(21) Appl. No.: 15/431,703

(22) Filed: Feb. 13, 2017

Related U.S. Application Data

(63) Continuation-in-part of application No. 14/543,883, filed on Nov. 17, 2014, now Pat. No. 9,609,911, (Continued)

(51) Int. Cl.
| *A61F 5/01* | (2006.01) |
| *A43B 7/32* | (2006.01) |
| *A43B 3/00* | (2006.01) |
| *A43B 7/14* | (2006.01) |
| *A43B 13/38* | (2006.01) |
| *A43B 5/00* | (2006.01) |
| *A43B 7/24* | (2006.01) |
| *A43B 17/04* | (2006.01) |
| *A43B 17/02* | (2006.01) |
| *A43B 3/24* | (2006.01) |
| *A43B 17/14* | (2006.01) |

(Continued)

(52) U.S. Cl.
CPC ............. *A43B 7/24* (2013.01); *A01K 87/00* (2013.01); *A01L 7/00* (2013.01); *A43B 3/0015* (2013.01); *A43B 3/246* (2013.01); *A43B 7/141* (2013.01); *A43B 7/1445* (2013.01); *A43B 13/141* (2013.01); *A43B 13/183* (2013.01); *A43B 17/02* (2013.01); *A43B 17/04* (2013.01); *A43B 17/14* (2013.01); *A61F 5/0123* (2013.01); *A63B 21/045* (2013.01); *A63B 21/0442* (2013.01); *A63B 21/4029* (2015.10); *A63C 10/00* (2013.01)

(58) Field of Classification Search
CPC ......... A43B 7/14–7/145; A43B 13/141; A43B 13/183; A43B 13/38; A43B 13/386; A43B 3/0036–3/0073; A61F 5/14
See application file for complete search history.

(56) References Cited

U.S. PATENT DOCUMENTS 4,922,631 A * 5/1990 Anderie ................... A43B 5/06
36/102
5,070,629 A * 12/1991 Graham ............... A43B 1/0072
36/27
(Continued)

*Primary Examiner* — Jila M Mohandesi
(74) *Attorney, Agent, or Firm* — Law Office of Carl Giordano, PC

(57) ABSTRACT

An active footwear suspension system is disclosed. The footwear system provides dynamic suspension using at least one or more variable resistance beams. At least one or more VRB from an anchor plate positioned forward of and/or aft of an arch section of the footwear, thus providing selectable suspension to the wearer. The selected rotation of the VRBs from a first position to a second position provides customized suspension between a minimum resistance to a maximum resistance per zone.

20 Claims, 54 Drawing Sheets

Related U.S. Application Data which is a continuation-in-part of application No. 13/622,331, filed on Sep. 18, 2012, now abandoned.

(60) Provisional application No. 62/379,602, filed on Aug. 25, 2016, provisional application No. 61/905,688, filed on Nov. 18, 2013, provisional application No. 61/585,315, filed on Jan. 11, 2012.

(51) Int. Cl.
| | | |
|---|---|---|
| *A43B 13/14* | (2006.01) | |
| *A43B 13/18* | (2006.01) | |
| *A63B 21/00* | (2006.01) | |
| *A63B 21/045* | (2006.01) | |
| *A63B 21/04* | (2006.01) | |
| *A01K 87/00* | (2006.01) | |
| *A01L 7/00* | (2006.01) | |
| *A63C 10/00* | (2012.01) | |

(56) References Cited

U.S. PATENT DOCUMENTS

| | | | | |
|---|---|---|---|---|
| 6,138,385 | A * | 10/2000 | Jungkind | A43B 1/0018 36/102 |
| 6,216,365 | B1 * | 4/2001 | Cohen | A43B 7/144 36/102 |
| 7,263,788 | B2 * | 9/2007 | Johnson | A43B 3/0063 36/107 |
| 7,421,805 | B2 * | 9/2008 | Geer | A43B 3/0036 36/102 |
| 8,453,344 | B2 * | 6/2013 | Nishiwaki | A43B 13/10 36/103 |
| 8,567,097 | B2 * | 10/2013 | Edy | A43B 3/0036 36/107 |
| 8,850,721 | B2 * | 10/2014 | Long | A43B 5/12 36/107 |
| 2010/0275460 | A1 | 11/2010 | Ha | |
| 2013/0178344 | A1 * | 7/2013 | Walsh | A01K 87/00 482/122 |
| 2015/0057587 | A1 * | 2/2015 | Walsh | A61F 5/0123 602/16 |

\* cited by examiner

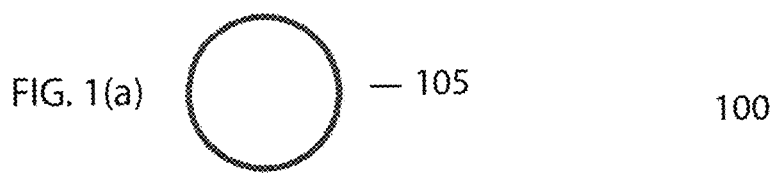
FIG. 1(a) — 105    100
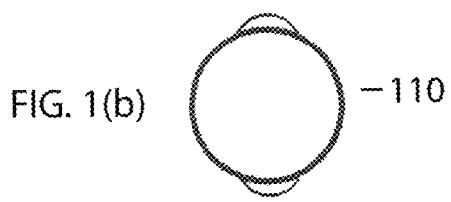
FIG. 1(b) — 110
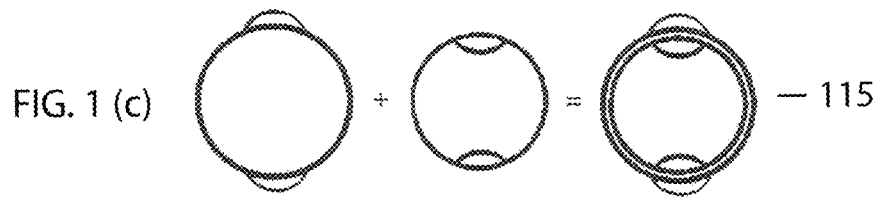
FIG. 1 (c) — 115
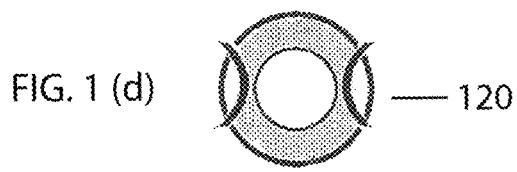
FIG. 1 (d) — 120
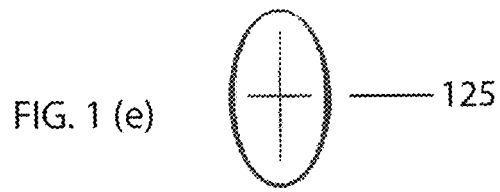
FIG. 1 (e) — 125
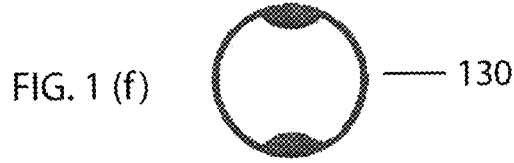
FIG. 1 (f) — 130
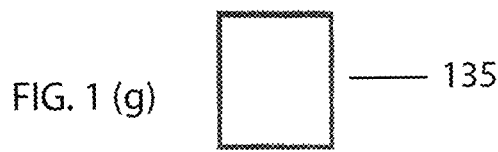
FIG. 1 (g) — 135

Type I

Fulcrum Resistance = Hand Positions = A, B, C, D, E, Indicia

Type II

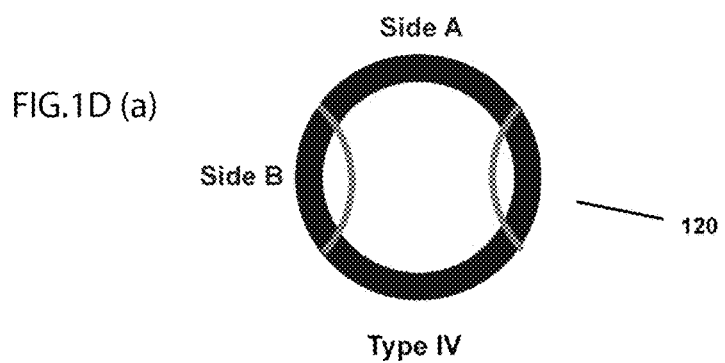
FIG.1D (a)
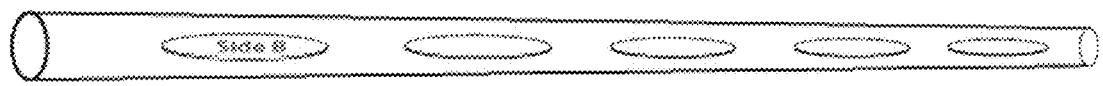
FIG.1D (b)
FIG. 1D (c)
FIG.1D (d)
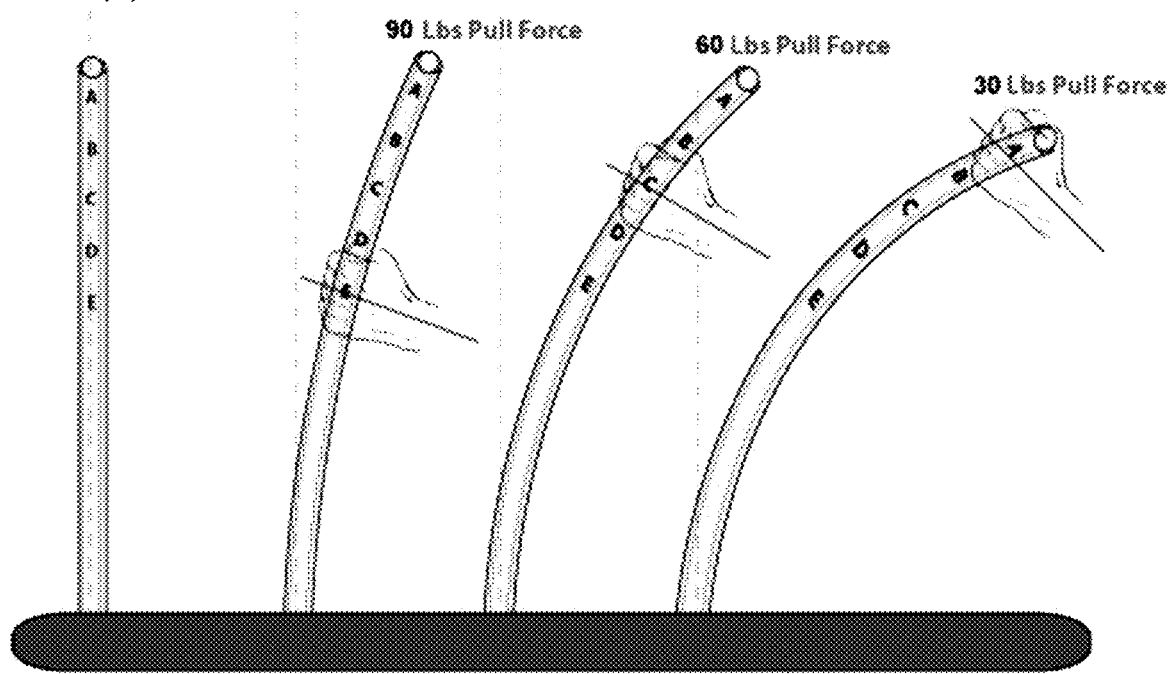

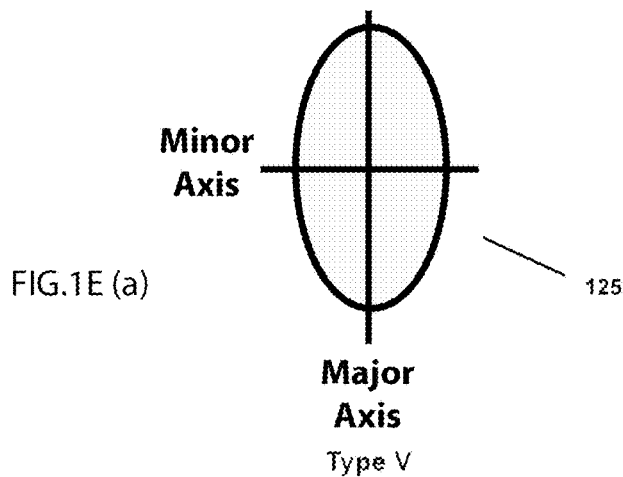
FIG.1E (a)
Type V
FIG.1E (b)
FIG.1E (c)
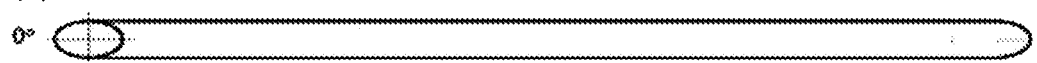
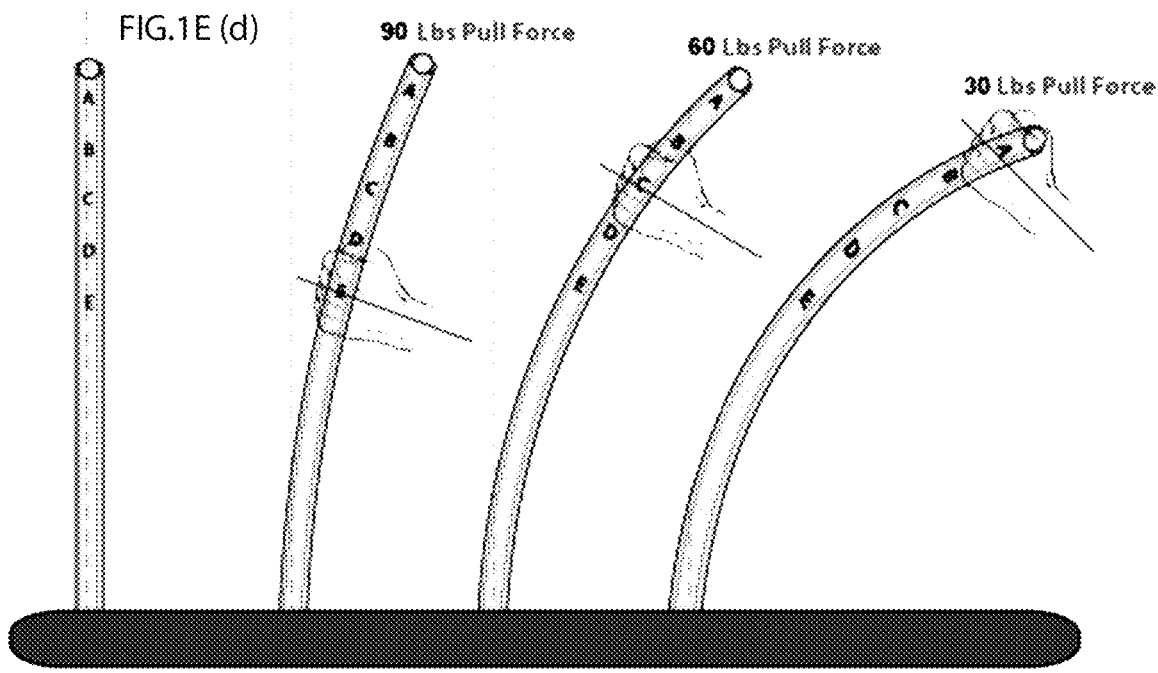
FIG.1E (d)

Type VI

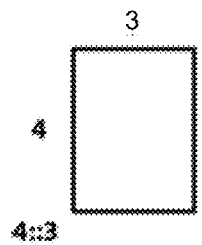 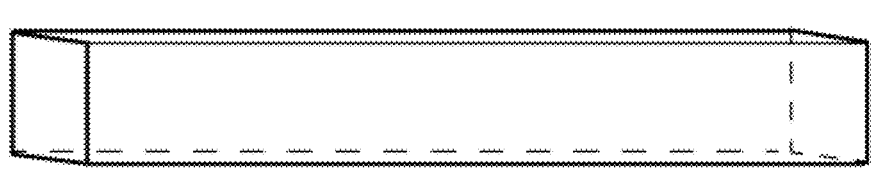
FIG.1G (a)
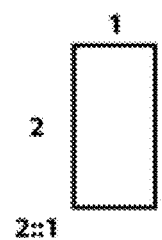
FIG.1G (b)
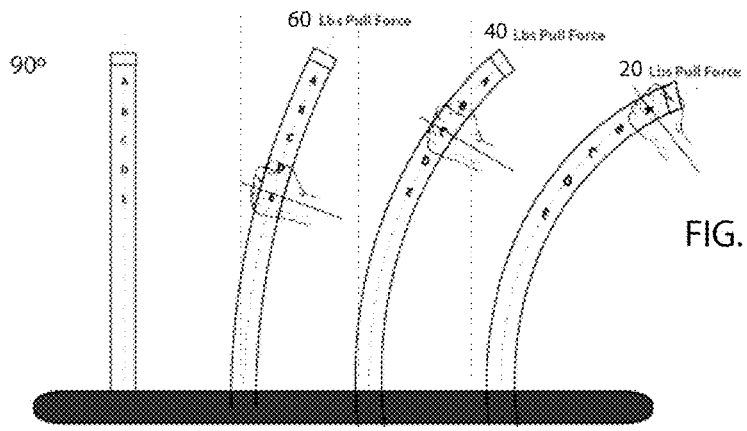
FIG.1G (c)
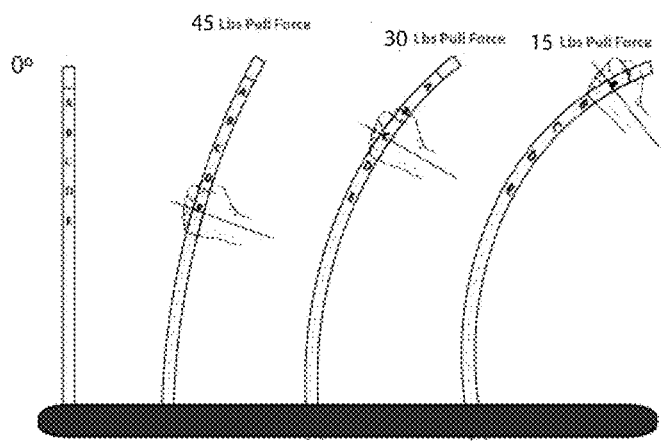
FIG.1G (d)

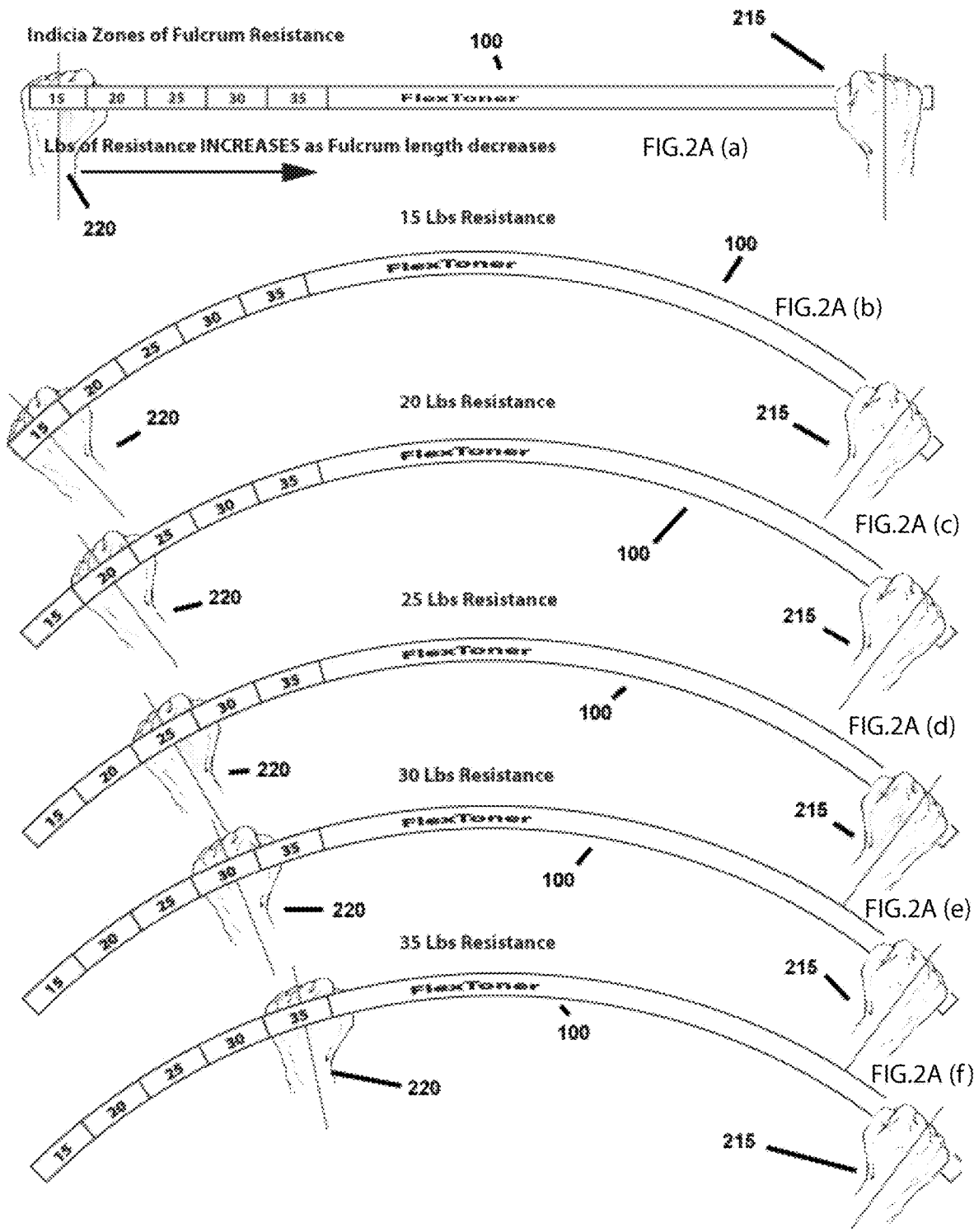

FIG.3 (a)
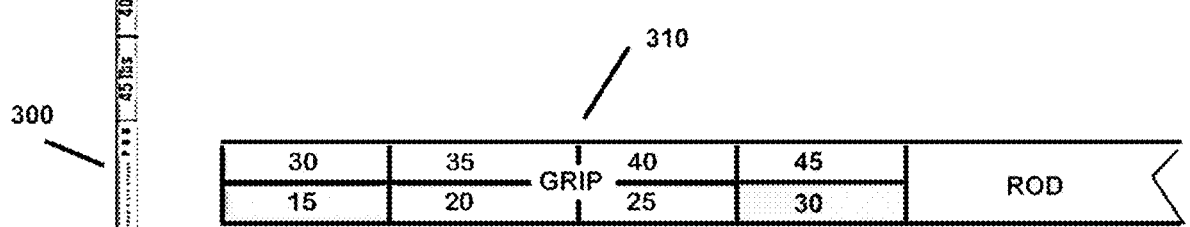
FIG.3 (b)
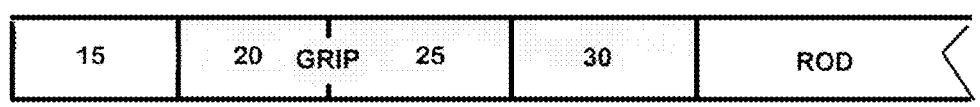
FIG.3 (c)

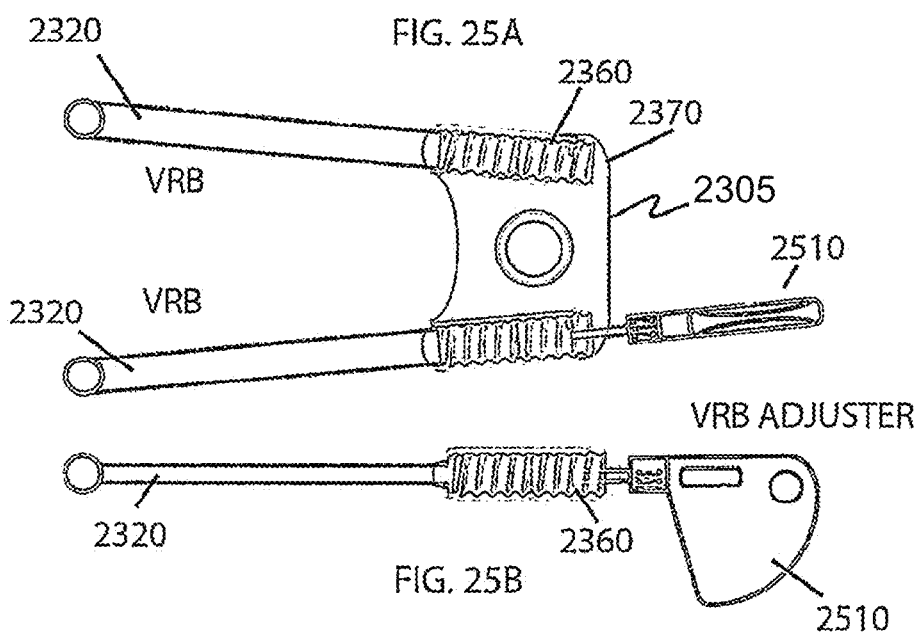
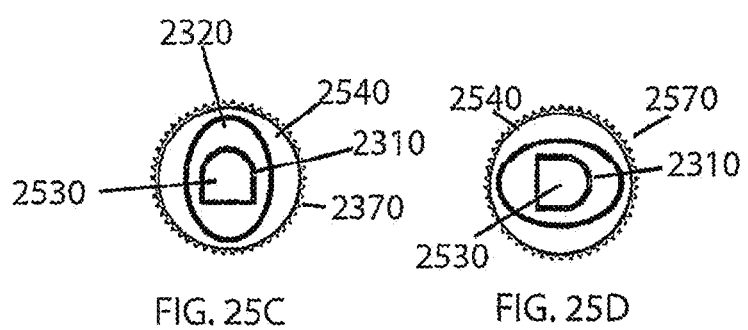

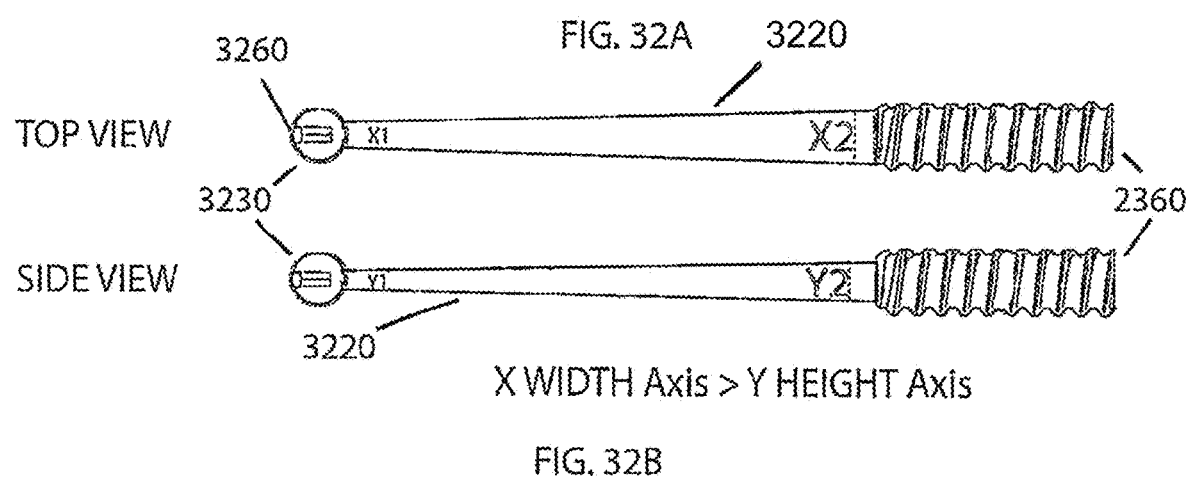

SYSTEMS AND METHODS FOR ADJUSTING VARIABLE GEOMETRY, HEIGHT, WEIGHT DISTRIBUTION IN FOOTWEAR DEVICES AND EQUIPMENT

CLAIM OF PRIORITY

This application claims, pursuant to 35 USC 119, priority to and the benefit of the earlier filing date of
that patent application filed on Aug. 25, 2016 and afforded Ser. No. 62/237,9602, and
further claims, pursuant to 35 USC 120, as a Continuation in part, priority to and the benefit of the earlier filing date of that
patent application filed on Nov. 17, 2014 (foot-001) and afforded Ser. No. 14/543,883 (now U.S. Pat. No. 9,609,911), which claimed, pursuant to 35 USC 119, priority to and the benefit of the earlier filing date of that
provisional patent application filed on Nov. 18, 2013 and afforded Ser. No. 61/905,688 and
pursuant to 35 USC 120, as a Continuation in part, priority to and the benefit of the earlier filing date of
that patent application filed on Sep. 18, 2012 and afforded Ser. No. 13/622,331, (now Abandoned) which claimed the benefit of the earlier filing date of
that provisional patent application filed on Jan. 11, 2012 and afforded Ser. No. 61/585,315, the entire contents of all of which are incorporated by reference, herein.

RELATED APPLICATION

The instant application is related to
that patent application filed on Feb. 6, 2017 and afforded Ser. No. 15/45772 (U.S. Pat. No. 10,188,173), which claimed priority to and the benefit of the earlier filing date of
that patent application filed on Nov. 17, 2014 and afforded Ser. No. 14/543,870 (U.S. Pat. No. 9,603,416), which claimed priority to
that patent application filed on Nov. 18, 2013 and afforded Ser. No. 61/905,99, and further claimed, pursuant to 35 USC 120, as a continuation in part,
that patent application filed on Sep. 18, 2012 and afforded Ser. No. 13/622,331, (now Abandoned) which claimed priority to and the benefit of the earlier filing date of
that patent application filed on Jan. 11, 2012 and afforded Ser. No. 61/585,315, the contents of all of which are incorporated by reference, herein.

FIELD OF THE INVENTION

This application is related to the field of footwear and, specifically with regard to systems and methods for controlling a degree of flex within the footwear.

BACKGROUND

There is a need for varying and adjusting the flexibility and stiffness of associated devices, apparatus and equipment to customize to a user's unique needs, and to the requirements of a particular task or desired outcome.

For example, in recent years, as it relates to the category of sports and fitness equipment, manufacturers and marketers have increasingly turned to different kinds of methods to enhance the customization and performance of sporting and fitness equipment. In some cases, entire lines of sporting equipment have been developed whose stiffness or flexibility characteristics are different from each other and are designed to be matched to the user's unique needs. Such differences, however, may be enough to give the individual equipment user an edge over the competition in that the equipment can be more personally customized, matched to a desired goal, and, therefore, enhance performance.

Until now, the user may choose a particular piece of sporting or fitness equipment having a desired stiffness or flexibility characteristic and, during play, switch to a different piece of sporting equipment that is slightly more flexible or stiffer to suit changing playing conditions or to help compensate for weariness or fatigue or some other anomaly that prevents optimum performance. Such switching, of course, is subject to the availability of different pieces of sporting or fitness equipment from which to choose, at the precise moment the change or adjustment is needed. In many cases, the availability is limited due to cost and over all impracticability.

Additionally, subtle but important changes in the stiffness or flexibility characteristics of sporting or fitness equipment may not be available between different pieces of sporting equipment, because the characteristics may be set by the manufacturer from the choice of materials, design, etc., and to change the characteristics would be impossible, as such customization isn't offered to the user. Further, the user must have the different pieces of sporting equipment nearby during play or they are essentially in practice unavailable to the user.

Thus, it can be seen how the lack of adjustability in stiffness and flexibility may adversely affect optimum performance of a device, apparatus, and equipment.

Turning to additional types of devices, apparatus and equipment, it can be seen how the lack of a practical means of adjustability in stiffness and flexibility may adversely affect performance.

Medical Devices, Apparatus, and Equipment

Medical devices, apparatus and equipment, such as braces that are used for supporting injured limbs, require the flexibility of the device to be adjusted based on the degree of the injury, type of surgery, and the progress of the healing of the injured party. Further, there is a need for on-going protection even after recovery. Yet the degree of adjustability of braces is limited, and, in most cases, fixed. Adjustability of the flexibility of the brace the brace to the specific needs and requirements of the user, may enhance recovery and protection from further injury.

Fitness Devices, Apparatus, and Equipment

Fitness equipment, apparatus and devices require the creation of different amounts of resistance to perform the exercise. For example, with free-weight training the user must change the weight levels to progressively increase the resistance that the user experiences. This often involves the continued and time consuming adjustment of equipment through an exercise cycle and makes changes impractical at best, and at the least a hassle.

Numerous heavy metal plates, large oily machines, weights, rubber bands, and singular resistance rods are the many known forms of fitness training. When the user changes resistance/weight or machine during an exercise set, it is time consuming and interrupts the user's conditioning.

Running Shoes, Training Shoes, Basketball Shoes

The transmission of the shoe wearer's strength (power) from their legs into the ground is directly affected by the sole stiffness of the shoe. Runners may gain more leverage and, thus, more speed by using a stiffer sole. Basketball players may also affect the height of their jumps through the leverage transmitted by the sole of their shoes. If the sole is too stiff, however, the toe-heel flex of the foot is hindered. Thus, athletic shoes are tailored, by the manufacturer, to the particular sport to which the shoe is to be used. In some case, it may be possible for the user have the ability to tailor the sole stiffness to his/her individual weight, strength, height, running style, and ground conditions. However, this process is performed by the manufacturer and is beyond the ability of the average user.

In footwear, various methods of materials and geometry have attempted to improve absorption of energy when the user's feet strike the pavement, ground or sports surface, and/or then release a greater percentage of this energy through the gait cycle. To date, static materials and various geometries have been common solutions. Yet none are dynamic or adjustable by the user in real time. Spring designs in shoe soles attempt to in part absorb energy and release energy but they have significant limitations and cannot be practically adjusted nor can they be dynamically adjusted in real time to current conditions.

Additionally, there is also no known way to control or adjust various zones of the sole to produce extra traction and/or grip during pronation of supination, or to adjust the flex of a particular sole zone to customize for greater comfort and support.

Golf

Golf clubs may be formed of graphite, wood, titanium, glass fiber or various types of composites or metal alloys. Each material varies to some degree with respect to stiffness and flexibility. However, golfers generally carry onto the golf course only a predetermined number of golf clubs. Varying the stiffness or flexibility of the golf club is not possible, unless the golfer brings another set of clubs. Nevertheless, it is impractical to carry a large number of golf clubs onto the course, wherein each club having a slight nuance of difference in flexibility and stiffness than another. Golf players prefer taking onto the course a set of clubs that are suited to the player's specific swing type, strength and ability.

Hockey

Hockey (hockey includes, but is not limited to, ice hockey, street hockey, roller hockey, held hockey and floor hockey) players may require that the flexure of the hockey stick be changed to better assist in the wrist shot or slap shot needed at that particular junction of a game or which the player was better at making.

Younger players may require more flex in the hockey stick due to lack of strength; such flex may mean the difference between the younger player being able to lift the puck or not when making a shot since a stiffer flex in the stick may not allow the player to achieve such lift. In addition, as the younger players ages and increases in strength, the player may desire a stiffer hockey stick, which in accordance with conventional means the hockey player would need to purchase additional hockey stick shafts with the desired stiffness and flexibility characteristics. Indeed, to cover a full range of nuances of differing stiffness and flexibility characteristics, hockey players would have available many different types of hockey sticks. Even so, the hockey player may merely want to make a slight adjustment to the stiffness or flexibility of a hockey stick to improve the nuances of the play; which is not possible with conventional technology Tennis Tennis players also may want some stiffness and/or adjustability in their tennis rackets and to resist unwanted torsional effects caused by the ball striking the strings during play. The torsional effects may be more pronounced in the case where the ball strikes near the rim of the racket rather than the center of the strings.

Lacrosse

Lacrosse players use their lacrosse sticks to scoop up a lacrosse ball and pass the ball to other players or toward the goal. The stiffness or flexibility of the lacrosse stick may affect performance during the game.

Other Racket Sports

Other types of racket sports also suffer from the drawback of being unable to vary the stiffness and/or flexibility of the racket during the course of play to suit the needs of the player at that time, whether those needs arise from weariness, desired held positions, or training for improvement. Such racket sports include racquetball, paddleball, squash, badminton, and court tennis.

For conventional rackets, the stiffness and flexibility is set by the manufacturer and invariable. If the player tires of such characteristics being fixed or otherwise wants to vary the stiffness and flexibility, the only practical recourse is to switch to a different racket whose stiffness and flexibility characteristics better suit the needs of the player at that time.

Skiing, Snowboarding, Snow Skating, Ski-Boarding

Skis are made from a multitude of different types of materials and dimensions, the strength and flexibility of each type differing to a certain extent. Skis include those for downhill, ice skiing, cross-country skiing and water-skiing. For soft snow conditions, the rider may want to have more flexibility so as to allow the board to float. For icier conditions, the rider may want to stiffen the highback to provide greater leverage and power, which results in greater edge control.

Bicycle Shoes

Bicycle specific shoes are rigid and may or may not be attached to bicycle pedals usually through a binding or clip mechanism that prohibits the shoe from slipping of the pedal. The shoe is positioned on the pedal so the ball of the foot is directly over the pedal. The rider's foot flexes as the pedal moves. However, the bicycle shoe is designed for pedaling and walking in these shoes is uncomfortable.

Fishing Rods

Fishing rods are flexed for casting out a line. The whip effect from the casting is affected by the stiffness or flexibility of the rod. Depending upon the fishing conditions and the individual tastes of the user, the user may prefer the rod to be either more flexible or stiffer to optimize the whip effect of the cast and to deal with wind, current, types of fish, and the like. Thus, the user must select the type of flexibility or stiffness when purchasing the fishing rod.

Fins

Diving and swimming fins provide different degrees of stiffness that are fixed, and unchangeable. However, the need to have more flex or less flex and, thus, control fin bend is dependent on the changing conditions. Optimum performance that matches the conditions may be possible with dynamically adjustable fin spine(s). It would also be advantages in that the swimmer/diver would not be unnecessarily fatigued if they had proper matching flex to the conditions.

Sailboating and Sailboarding

Masts of sailboats and sailboards support sails. In many cases the users must adjust the amount of sail that is hanging from the mast according to the weather conditions to prevent damaging the mast caused by stress on the mast.

Canoeing, Rowboating and Kayaking

Paddles for canoes, row boats, and kayaks are subjected to forces as they are stroked through water. The flexibility or stiffness of the paddles, while different depending upon its design and materials, is fixed by the manufacturer. Thus, a rower who desired to change such characteristics would need to switch to a different type of paddle. Carrying a multitude of different types of paddles for use with a canoe, row boat or kayak, however, is generally impractical for the typical rower from the standpoint of cost, bulk and storage.

Lawn Rake

There are times when the flex of a rake's tines are either too flexible or too stiff for the task at hand, be it for raking gardens, light leaf, matted thatch, wet grass, debris. Often the user has to purchase a second rake to accommodate these additional needs.

In addition to athletes desiring to customize their equipment and disclosed previously, athletes have increased physical performance demands for each sport specialty they play, and therefore require different shoe types to enhance their athletic performance, style and technique.

Athletes and the general population all, to some degree, have pronation, supination and heel cushion issues when walking, running and/or playing.

Shoe soles are typically generic, static and are not adjustable once assembled or molded. This fixed or static quality offers the wearer no after-market method to adjust the performance of a shoe or shoe sole.

Hence, there is a need in the footwear industry of a platform system integrated into the sole of footwear that provides the user with the ability to customize or adapt their footwear in order to provide a comfortable fit during different activities, to improve performance, and specifically for the ability of the user to customize and control the degree of energy absorption, and release of energy commensurate with the activity demands.

SUMMARY OF THE INVENTION

The invention relates to a variable resistance beam or rod that may dynamically control the stiffness and flexibility of devices, apparatus, and equipment. The resilient rods, beams or shafts of solid, semi-solid or hollow construction produce resistance and variable resistances when orientated in a direction of x, y, z plane or combination of planes in 360 degrees of rotation or bending movement.

The variable resistance rod (VRB) technology may be incorporated into different equipment (sports & fitness, lawn, medical, etc.) that require different degrees and direction of stiffness and flexibility, wherein the different degrees of stiffness and flexibility may be controlled in the field in real time by means of a selector, a worm gear, or other mechanical methods to affect a rotated orientation of the variable resistance rods, or by simple hand placement in relation to the fulcrum indicated by an indicia of color, number, symbol or other means.

One aspect of the invention resides in a resilient or resistance rod acting to create variable resistance that incorporates a selectable or adjustable flex resistance by means of hand position and placement.

One aspect of the invention resides in a resilient rod, beam or shaft, including at least one spine, extending substantially the length of the rod, beam or shaft, that provides for variable degrees of flexibility of the rod, shaft or beam depending upon the orientation of the spine with regard to a direction of flex One aspect of the invention resides in equipment that adjusts to provide variations in stiffness and flexibility. The equipment may have a rod, beam or shaft with an elongated cavity or rod, an elongated flexure resistance spine, one, two or more locking elements that secure the rod, shaft or beam against rotation at spaced apart locations within the cavity. The rod, shaft or beam is stiffer and less flexible in one direction than in another.

Another aspect of the invention resides in sports equipment that provides variations in stiffness and flexibility. The sports equipment may have an elongated cavity, and a means imparting stiffness and flexibility variations within the cavity so the sports equipment becomes stiffer, and less flexible, in one direction than in another, and one or more locking elements that secure the means against rotation in spaced apart locations within the cavity.

A further aspect of the invention resides in a method of varying stiffness and flexibility, comprising providing equipment (e.g., sports & fitness, medical, footwear & sneakers) having an elongated cavity; imparting stiffness and flexibility variations within the cavity so that the equipment becomes stiffer and less flexible, in one direction than in a different direction; and securing against rotation at least one location within the cavity while imparting stiffness and flexibility variations.

An additional aspect of the invention resides in a resilient shaft or beam acting alone to create variable resistance that incorporates a selectable or adjustable flex resistance by means of varying hand position and placement on the resilient rod in relationship to the fulcrum of the bended rod.

An advantage of the present invention is the ability to provide constant and consistent flex adjustment. This advantage arises from the adjustment being locked in at the ends of the shaft and, depending upon the application, at one or more additional locations through the length of the shaft.

A resilient rod acting alone is also embodied to create resistance that incorporates adjustable flex or resistance by means of hand position and/or specific rotation for means of exercise employing progressive dynamic resistance, which relates to the advantages in exercise of varying degree weight and resistance through a particular cycle.

Footwear, as is known, generally provides a user with a stable platform upon which the user may walk, run, jog, exercise, etc. The present invention embodies a platform integrated into the sole of footwear whose rigidity provides leverage to the variable resistance beams (VRB) for selectable bio-mechanical advantage for the user.

In accordance with the principles of the invention, an adjustable and customizing support zones of a shoe sole is provided by the embedding or insert molding into the matrix of the sole, a new and novel footwear module or adjustable platform system to augment athletic and everyday performance.

The footwear platform is a module based design to be embedded into specific areas of the shoe sole, to maximize beneficial VRB mechanics, flexural leverage and energy return, to augment natural movement and correct misalignments of the foot across multiple shoe sole type.

The composite structure of a shoe sole combined with an insert molded module allows the shoe sole to flex in proportion and concert with the VRB flex seeting and/or per zone of the sole.

The incorporation of the VRB into the shoe sole provides a greater flexibility rand or lower resistance to sole flex when the VRB is in its low setting and greater resistance of sole flex and greater support, per zone when in its high setting.

In accordance with the principles of the invention, VRBs act as adjustable resistance cantilevers to provide a selectable range of dynamic and reactive suspension to the foot, in one or multiple zones.

In accordance with the principles of the invention one or more VRBs in an integrated platform system are applied to footwear structures to support the foot. The invention generally delineates one or more VRBs per zone to biomechanically affect, support, correct and or enhance any imbalance of the lower extremity or foot, or to proactively adjust stiffness in real time to gain greater performance benefits.

VRBs act as adjustable resistance cantilevers to provide a selectable range of dynamic and reactive suspension to the foot.

In accordance with the principles of the invention, Multiple VRBs or zones can be employed to correct and support the bio-mechanical needs of the user. Typically up to 4 or more VRBs or zones are employed to positively biomechanically correct imbalances or enhance athletic performance of the front right/left and rear right/left sections of the foot.

The invention also embodies flexible materials that form geometries and sole structures that ergonomically conform, deform, and/or change shape to the mechanical setting of the VRB resistance range settings.

Additionally, as one example of flexible mid arch material with adaptable geometry connected to a VRB to impart selective and corrective real-time reactive bio-mechanical support, a VRB would impart increasing or decreasing vertical height to meet the user's ergonomic arch shape and bio-mechanical arch support requirements.

In accordance with the principles of the invention, the integrated suspension system may be connected to a corresponding VRB to impart selective, reactive and corrective real-time, bio-mechanical support.

In accordance with the principles of the invention, the unique biomechanics feature of selectable dynamic suspension coupled to produce a conformal adapting orthotic shell geometry to support the foot in direct proportion to foot loading is called self or auto leveling.

In accordance with the principles of the invention, an optional synthetic plantar fascia or rubber connector tendon may be utilized to join two modules together, while embedded in the shoe, to capture and release additional stored energy from sole flexure.

In accordance with the principles of the invention, this synthetic (or rubber or elastomeric material) connector may provide additional energy return from being stretched and released, typically during the last ⅔ to ¾ toe off period of the gait cycle.

In accordance with the principles of the invention, a modular elastometic unibody or polymeric platform anchors each individual VRB via a threaded socket, that simultaneously acts as a VRB placement holder and a VRB resistance selector.

Each anchor module is typically comprised of an elastomeric material with one or two VRBs, threaded into a corresponding VRB placement holder i.e., threaded receiver).

In accordance with the principle of the invention, a plurality of VRBs (e.g., 4 VRBs, for quadrant zones) may be employed for each sole with typically one VRB for each zone to provide selectable support range to customize the shoe sole.

In accordance with the principles of the invention, the VRB incorporates a threaded or helix section that is typically located at a mid or an end joint location along the a long (longitudinal) axis of the VRB. The helix or screw thread provides continuous and incremental VRB adjustment capability in any of zero (0) to ninety (90) degrees of rotation. Thread pitch determines the travel distance the VRB forward or rearward (linear advance) while rotating from a minimum to a maximum resistive position.

In accordance with the principles of the invention, a modular elastomeric platform incorporates a threaded pocket or socket that anchors a corresponding VRB. The threaded socket operates simultaneously as a VRB selector and a VRB receiver. Each module anchor is mold engineered to a specific inside diameter with tight mating tolerance to each outside diameter VRB barrel with threaded helix. The combined inside diameter and outside diameter mating fit combined with the module's material coefficient of friction (i.e., material durometer) grips the vRB and holds the VRB in any incremental, fixed rotated or selected position.

Each module typically houses two vrb selectors/receivers aligned in either a perpendicular orientation and or in an obtuse (greater than 90° but less than 180°) spread angle or symmetrically flared configuration.

In accordance with the principles of the invention the module's selectors lay in a same flat or horizontal plane but may also be inclined to increase advantageous VRB flexural mechanics.

In accordance with the principles of the invention, the flexible elastomeric VRB anchor platform provides for independent torsion (side to side twisting or flexing) for each individual VRB zone.

The VRB modules can either be independently embedded into the shoe sole (unconnected) and/or connected by an elastomeric tendon acting as a second plantar fascia tendon.

In accordance with the principles of the invention, the optional use of a synthetic plantar fascia or rubber elastomeric connector tendon between the two modules embedded in the shoe sole to capture and release stored energy.

Additionally, an enhanced performance range of selectable support may be achieved by wrapping the elliptical or rectangular VRB cross section with high tenacity tensile thread (braided or not) made of cotton, nylon, polyester, kevlar, spectra, dyneema, nanowire et al.

The VRB may be molded from polymeric materials, GRP glass reinforced polymers or machined from high tensile spring metal and/or martensitic steels, all incorporating a threaded helix to rotate (and fasten) into a matched module receiver/selector threads.

Additionally, patterned guide grooves may be molded or machined into the VRB shank or flexing segment of the VRB for thread wrapping.

The guide grooves ensure a consistent structural wrapping pattern for the high tensile thread, to increase the VRB's mechanical (flexural) strength envelop achieved by forming a composite beam, formed from two complimentary materials.

VRB mechanical flex range can be increased or decreased dependent upon the number of thread windings or wraps along the VRB shank and or the tensile strength of the winding thread.

The net mechanical effect of using a VRB polymer with a high Young's modulus or spring strength (e.g., Nylon) wrapped by a high tensile thread, creates a modulated and super strong variable resistant composite beam, with a wider mechanical Minimum to Maximum selectable support range.

The composite mechanical flexural beam effect is analogous to slow and fast twitch muscle fibers and is self-moderating and provides for a controlled return rate.

In accordance with the principles of the invention, this moderation or rate level of reaction to being mechanically flexed can be engineered to match the flex cadence of the gait of the foot.

The VRB complimentary materials' compression and tension return rate characteristics may be engineered to return to their natural or neutral state at a controlled rate matched to the cyclic human gait.

In accordance with the principles of the invention, It is possible to match the beam's flexural characteristics with the natural cadence of the human gait, by controlling the Young's modulus of a VRB's core polymer matched with a tensile strength of high tenacity wrapping thread, e.g., flexural cadence of the foot gait cycle matched to the flex recovery time of the two composite VRB (polymeric) materials.

In accordance with the principles of the invention, additional capability may be achieved by applying sensors to one or up to four or more flexing VRBs, to provide the ability to measure VRB beam performance and predictably that of the wearer or athlete. This imparts useful biomechanics data to monitor, quantify and record the physical exertion and warn of potential injury factors from overuse. Data is either collected onboard an embedded PCB (printed circuit board) or transmitted wirelessly to a smart device.

The foot supporting plate described herein incorporates a superior, elastomeric based module to anchor the vrbs. The modular system provides for multiple placements within any existing shoe sole, brand or type.

BRIEF DESCRIPTION OF THE DRAWINGS

For a better understanding of exemplary embodiments and to show how the same may be carried into effect, reference is made to the accompanying drawings. It is stressed that the particulars shown are by way of example only for purposes of illustrative discussion of the preferred embodiments of the present disclosure, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings:

FIG. 1(a)-FIG. 1(g) represents exemplary views and cross sections of resilient rods, beams or shafts of solid, semi-solid or hollow construction in accordance with a first aspect of the invention that produce resistance and variable resistances when orientated in a direction of x, y, z plane or combination of planes in 360 degrees of rotation or bending movement.

FIG. 1(a) represents a Type I I-Beam configuration that is substantially circular;

FIG. 1(b) represents a Type II I-Beam configuration that includes a spline;

FIG. 1(c) represents a Type III Dual I-Beam configuration that includes an inner and outer spline;

FIG. 1(d) represents a Type IV Conical beam configuration having cut-out section;

FIG. 1(e) represents a Type V Ellipsoidal beam configuration having a major and minor axis;

FIG. 1(f) represents a Type VI Internal 'I-beam' configuration having a internal spline; and FIG. 1(g) represents a Type VII Rectangular beam configuration.

FIGS. 1A(a)-(c) thru FIGS. 1G(a)-(d) 'illustrate examples of the resilient rods in accordance with aspects of the embodiment of the invention as shown in FIG. 1(a) thru FIG. 1(g) regarding cross-section, resistance and bending force applied to different hand positions.

FIG. 2A(a)-FIG. 2A(f) Illustrates a comparison of a symmetric or basically round and an asymmetric or elongated cross sectional rod held at two positions.

FIG. FIG. 3(a)-FIG. 3(c) illustrates a rod with an outside diameter with marked sets of indicia that specify the range of flexural resistances proportionate to the tensile strength of the beam material and fulcrum length per hand position[s] for symmetric or basically round (1 set) and (2 set) asymmetric or elongated cross sections.

Figure 20A:
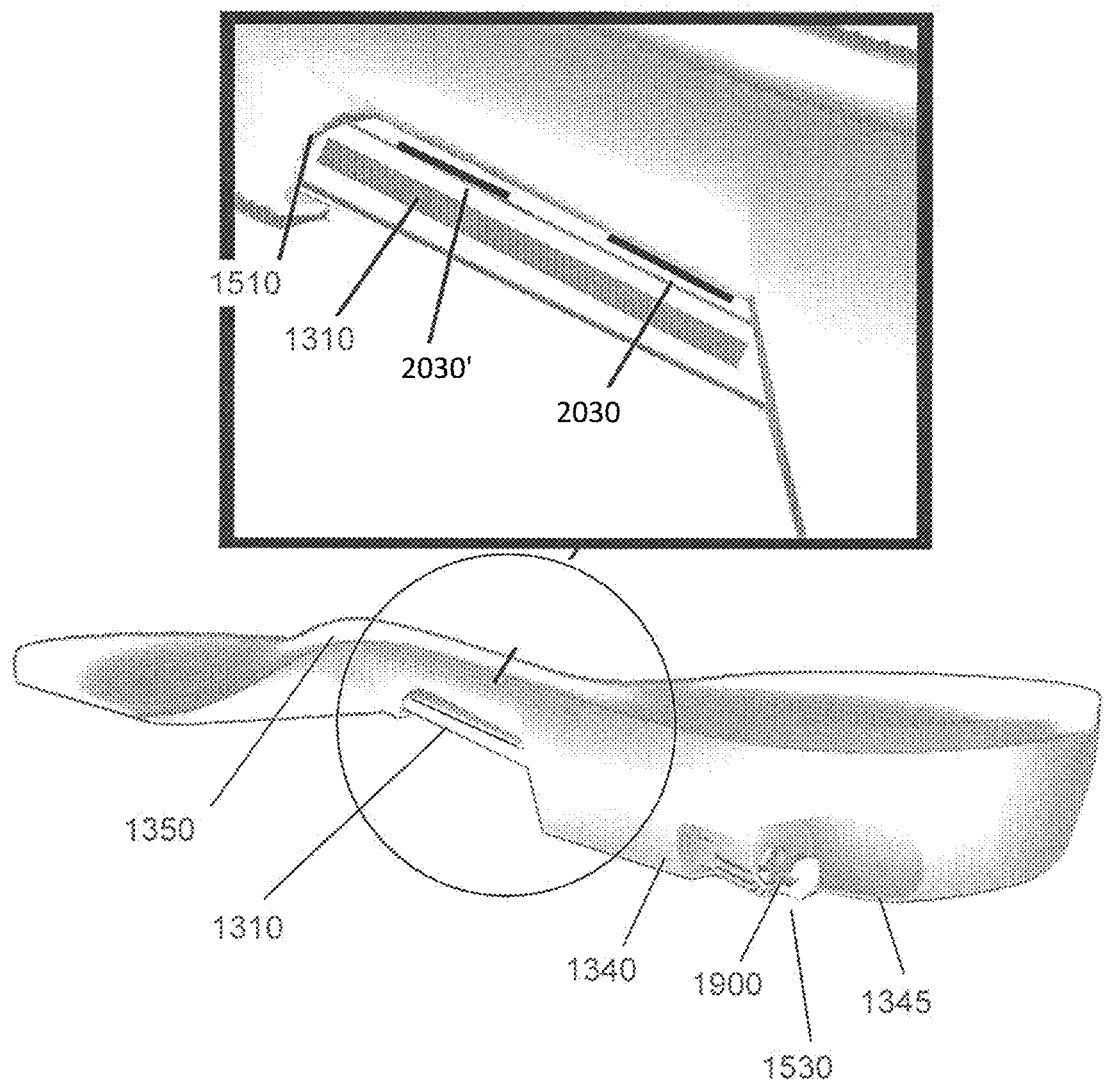
FIG. 20A illustrates a planar view (a) and a side view (b) of an exemplary embodiment of a footwear incorporating VRB and sensing technology in accordance with the principles of the invention.

FIG. illustrates an application of the aspect of the configuration shown in FIG. 20A.

Figure 22A:
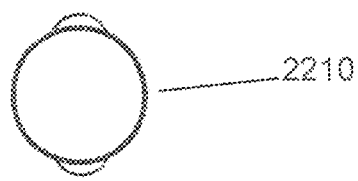
Figure 22B:
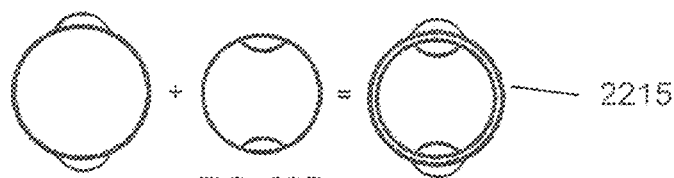
Figure 22C:
Figure 22D:
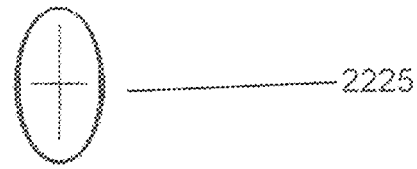
Figure 22E:
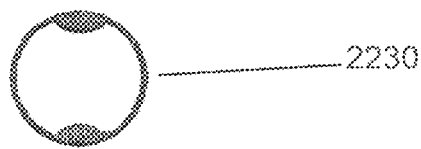

FIG. 22A-FIG. 22F illustrate edge views of exemplary configurations of a variable resistance beam in accordance with the principles of the invention, wherein FIG. 22A represents a Type II I-Beam configuration;

FIG. 22B represents a Type III Dual I-Beam configuration;

FIG. 22C represents a Type IV Conical beam configuration;

FIG. 22D represents a Type V Ellipsoidal beam configuration;

FIG. 22E represents a Type VI Internal 'I-beam' configuration; and

Figure 22F:
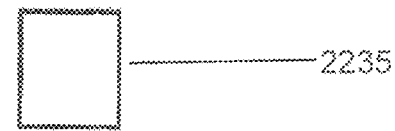

FIG. 22F represents a Type VII Rectangular beam configuration.

Figure 23A:
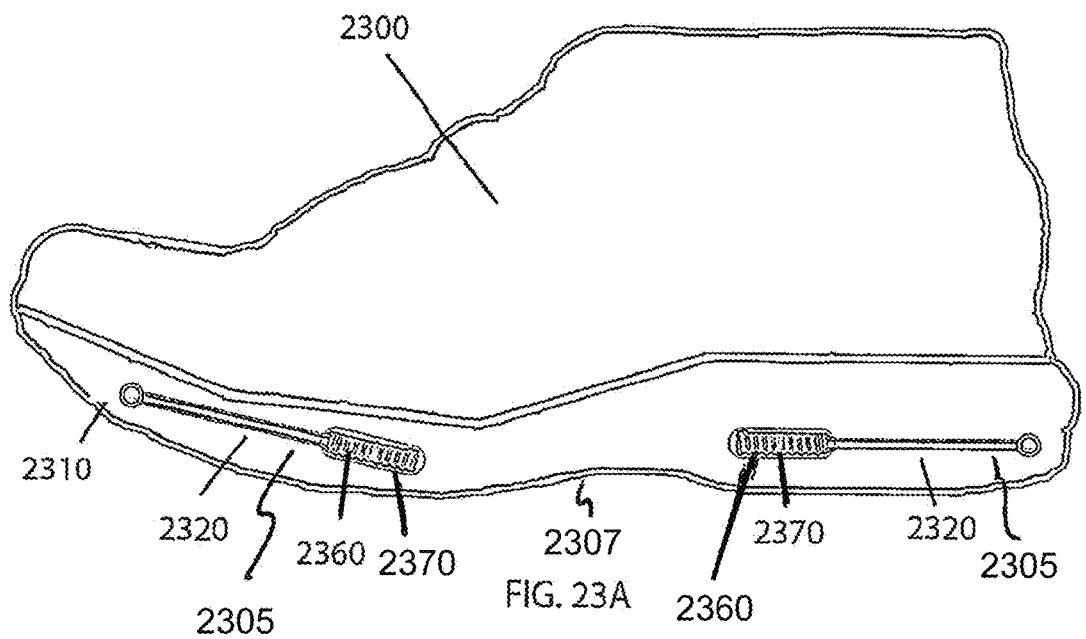

FIG. 23A illustrates a side view of an exemplary shoe configuration in accordance with the principles of the invention.

Figure 23B:
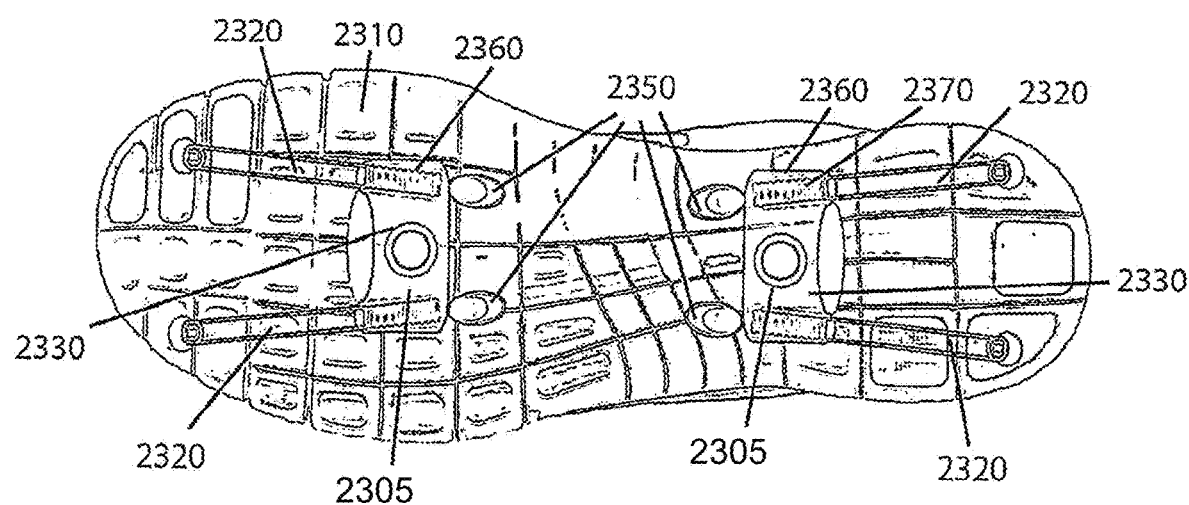

FIG. 23B illustrates a bottom view of the exemplary shoe configuration in accordance with the principles of the invention.

Figure 24A:
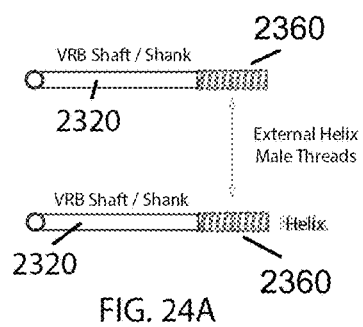

FIG. 24A illustrates an exemplary VRB utilized in the exemplary configuration shown in FIG. 23A, in accordance with the principles of the invention.

Figure 24B:
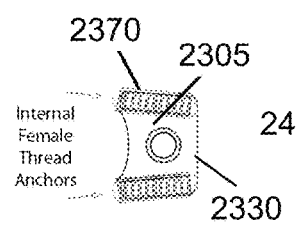

FIG. 24B illustrates an exemplary anchor module in accordance with the principles of the invention.

Figure 24C:
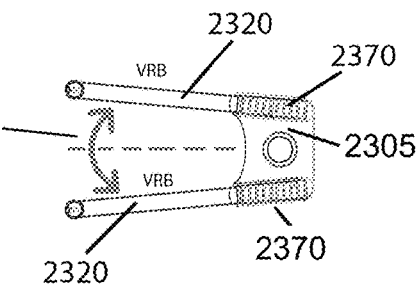

FIG. 24C illustrates a combined VRB and anchor module in accordance with the principles of the invention.

FIG. 25A illustrates a bottom view of a combined VRB and anchor module and an adjustment tool suitable altering an orientation of the VRB in accordance with the principles of the invention.

FIG. 25B illustrates a side view of the combined VRB and anchor module and adjustment tool shown in FIG. 25A.

FIG. 25C illustrates an end view of a VRB, in a maximum resistance position, showing an exemplary indentation matching the adjustment tool.

FIG. 25D illustrates an end view of a VRB in a minimum resistance position, showing the exemplary indentation shown in FIG. 25C.

Figure 26A:
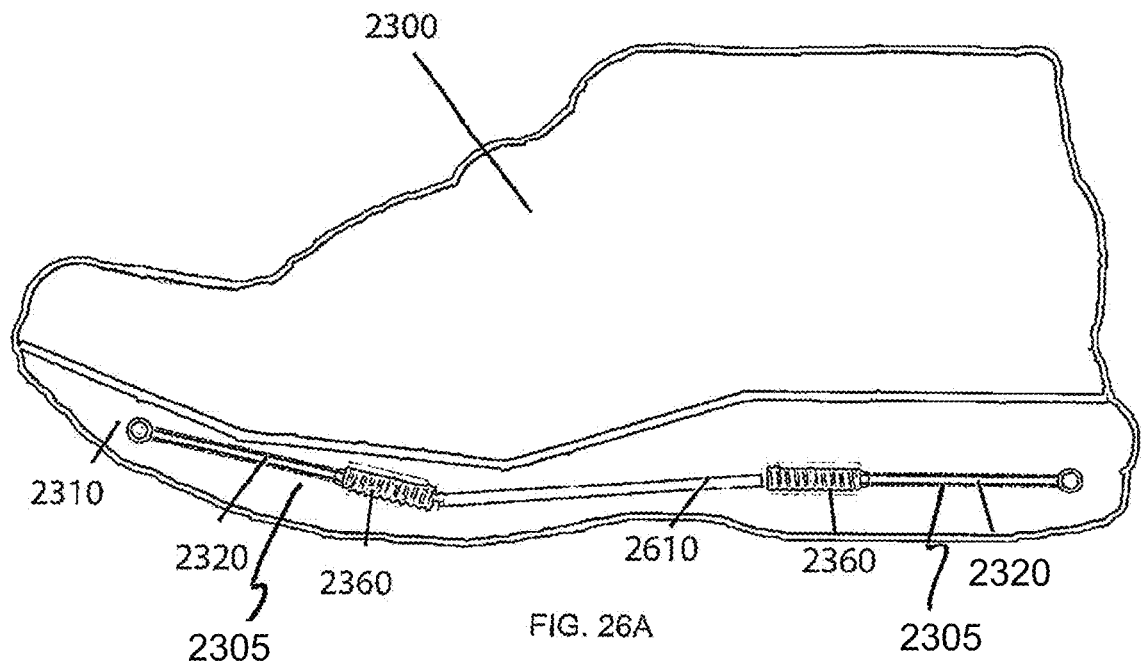

FIG. 26A illustrates a side view of a second exemplary shoe configuration in accordance with the principles of the invention.

Figure 26B:
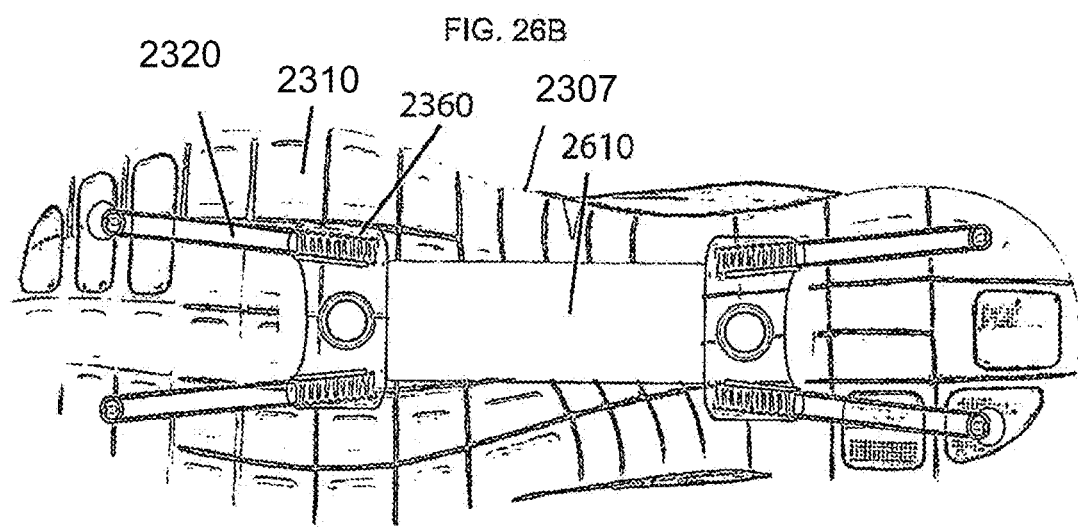

FIG. 26B illustrates a bottom view of the second exemplary shoe configuration shown in FIG. 26A.

Figure 26C:
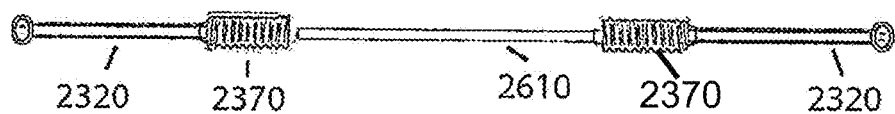

FIG. 26C illustrates a side view of the footwear module or adjustable platform configuration shown in FIG. 26A.

Figure 27A:

FIG. 27A illustrates a side view on a second exemplary VRB configuration in accordance with the principles of the invention.

Figure 27B:
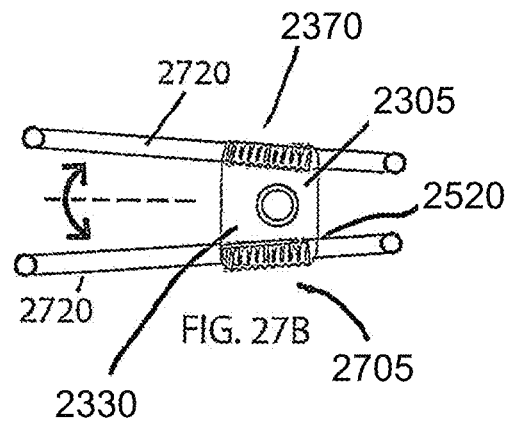

FIG. 27B illustrates a combined VRB/anchor configuration shown in FIG. 27A.

Figure 28A:
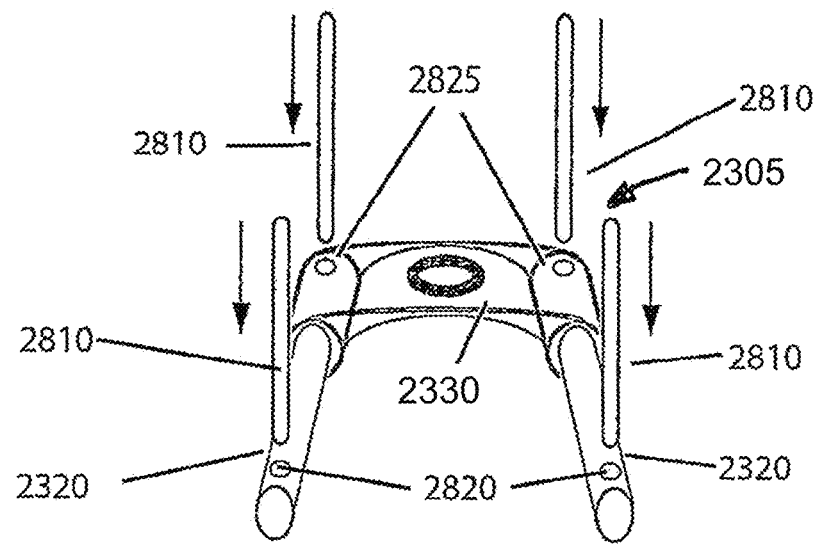
Figure 28B:
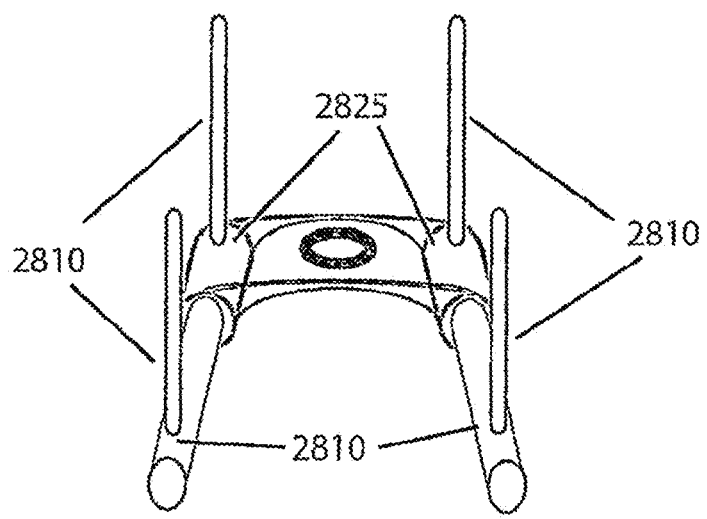

FIG. 28A and FIG. 28B illustrate a front prospective view of a combined VRB/anchor configuration including alignment pins.

Figure 29A:
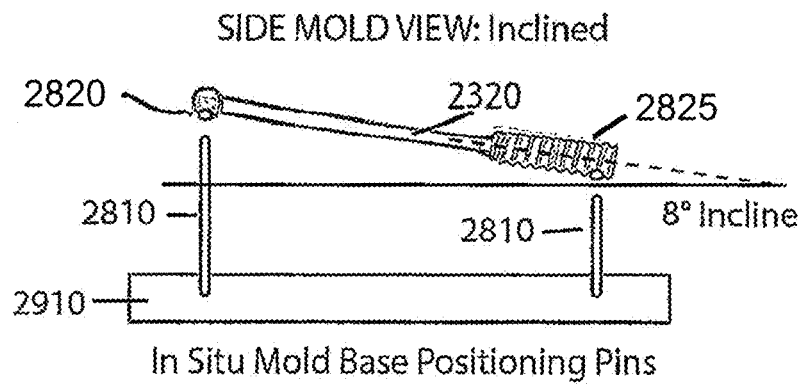
Figure 29B:
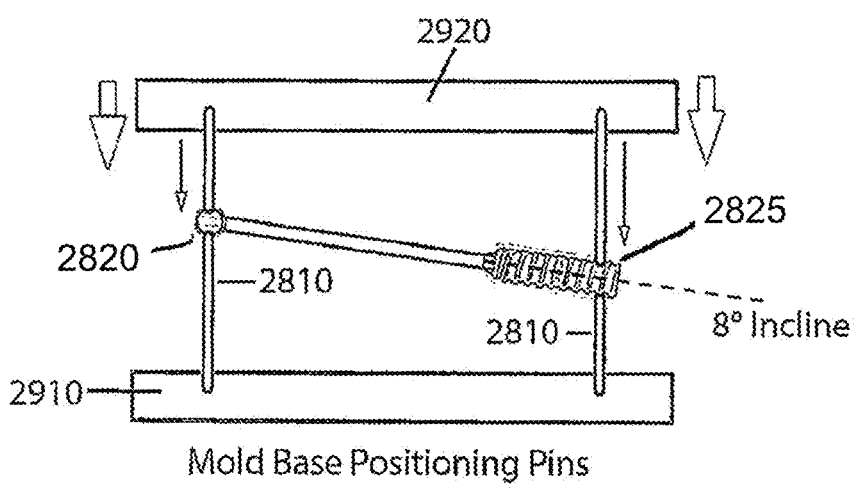

FIG. 29A and FIG. 29B illustrates an exemplary mold forming alignment configuration in accordance with the principles of the invention.

Figure 30:
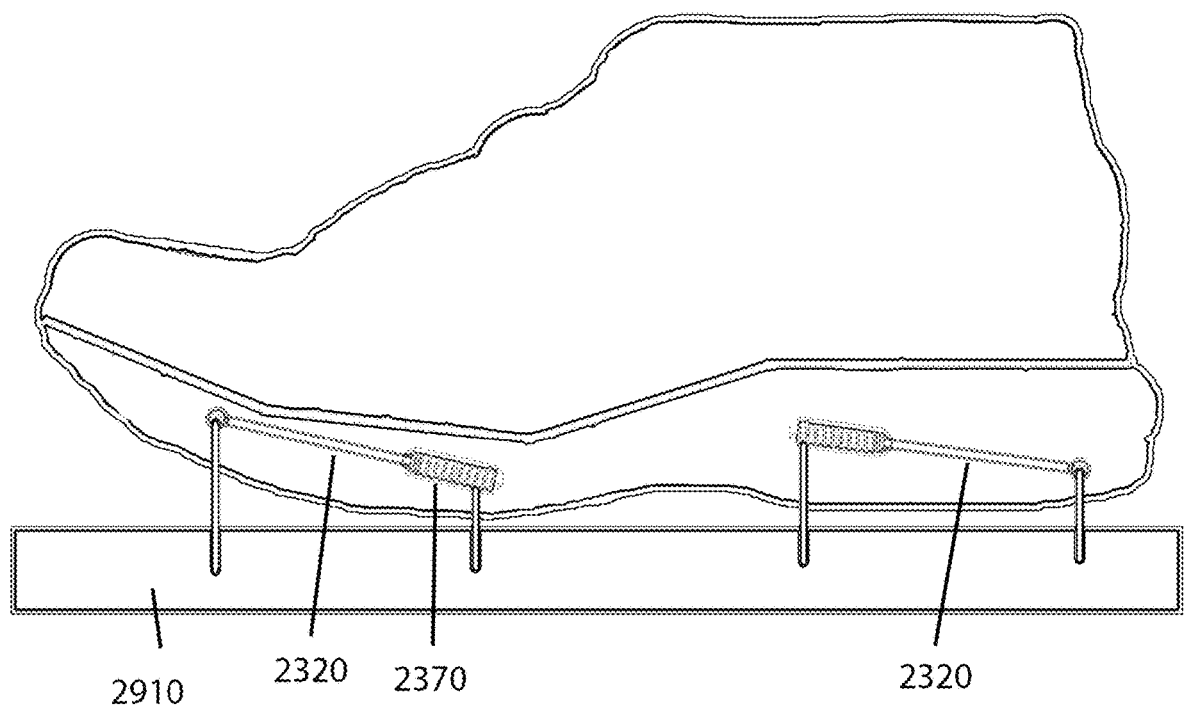

FIG. 30 illustrates an exemplary mold configuration associated with the shoe configuration shown in FIG. 23.

Figure 31:
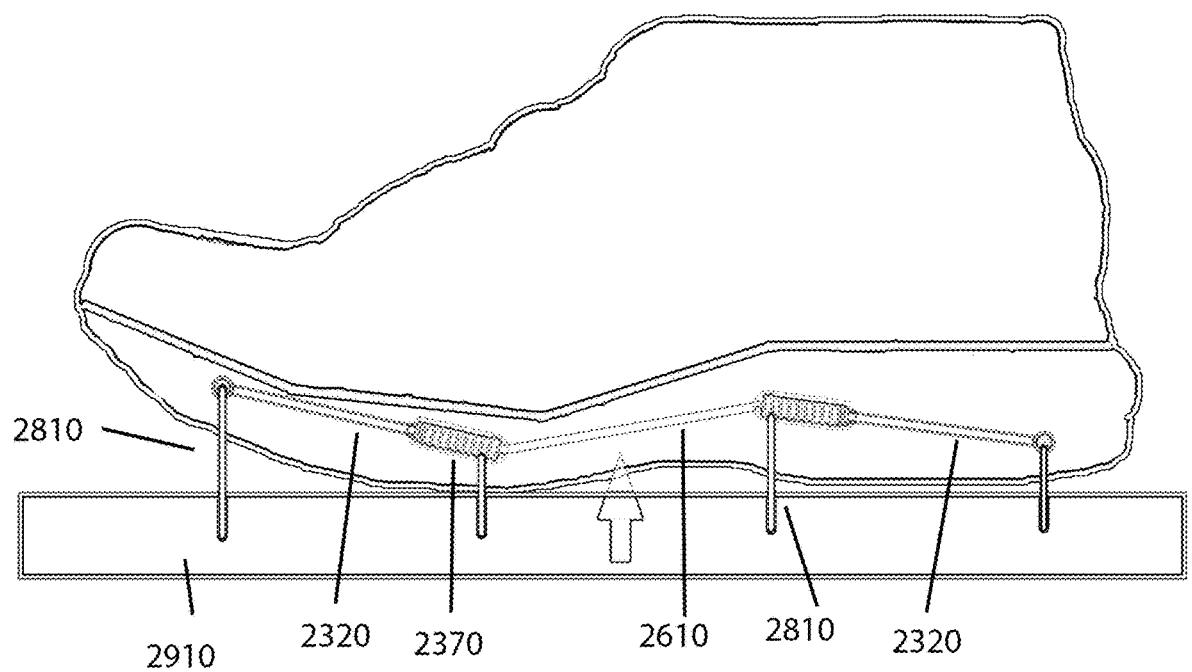

FIG. 31 illustrates an exemplary mold configuration associated with the shoe configuration shown in FIG. 26.

FIGS. 32A and 32B illustrate top and side, respectively, views of an exemplary VRB in accordance with the principles of the invention.

Figure 33A:
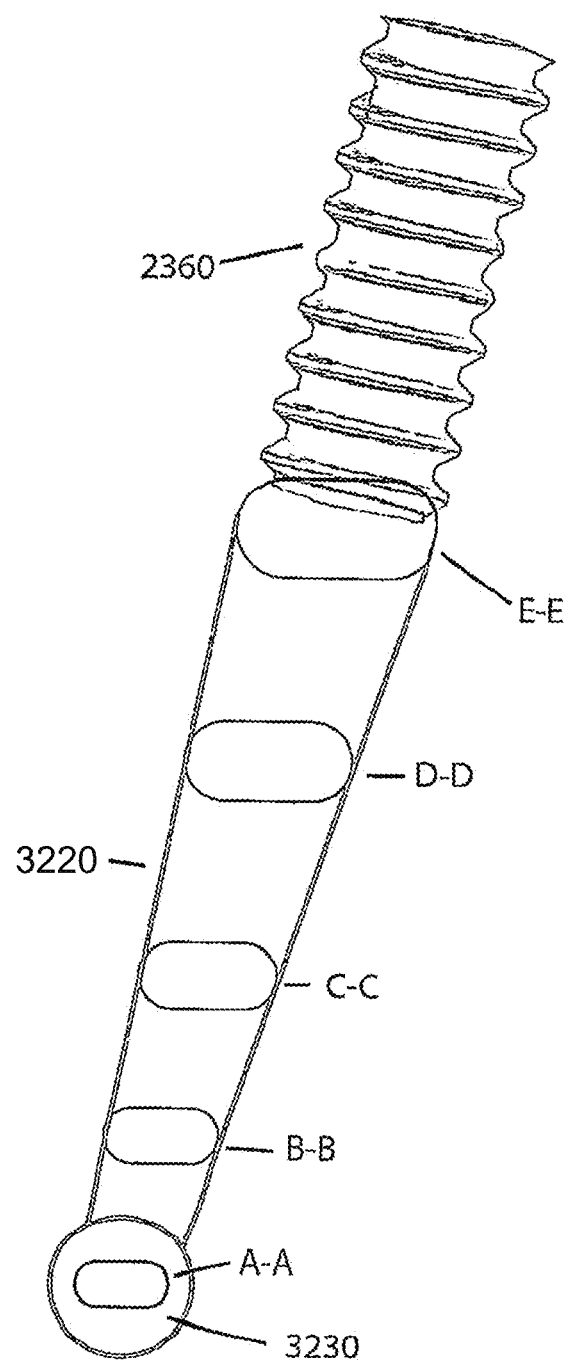

FIG. 33A illustrates a prospective view of a variable resistance beam in accordance with the principles of the invention.

Figures 33B, 34B:
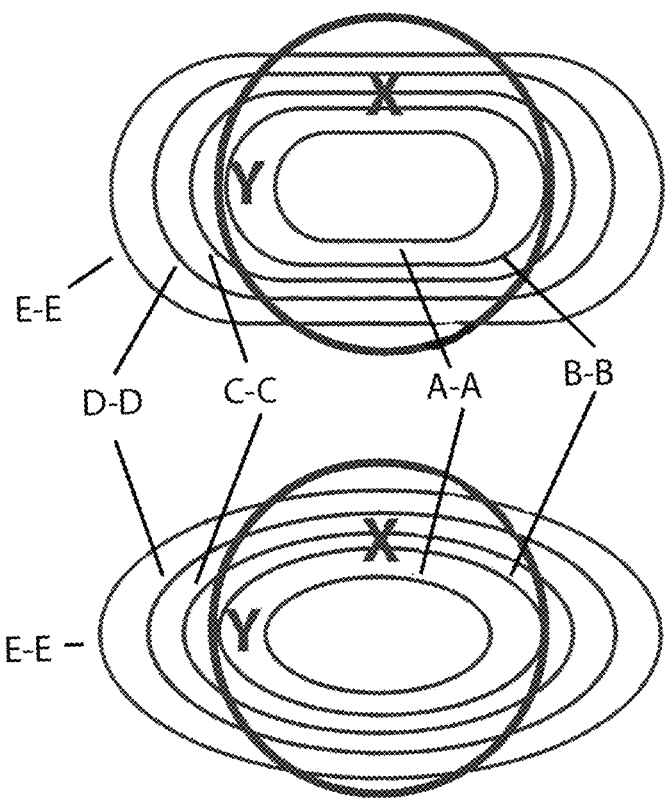

FIG. 33B illustrates a multi-sectional cross sectional view of the VRB shown in FIG. 33A.

Figure 34A:
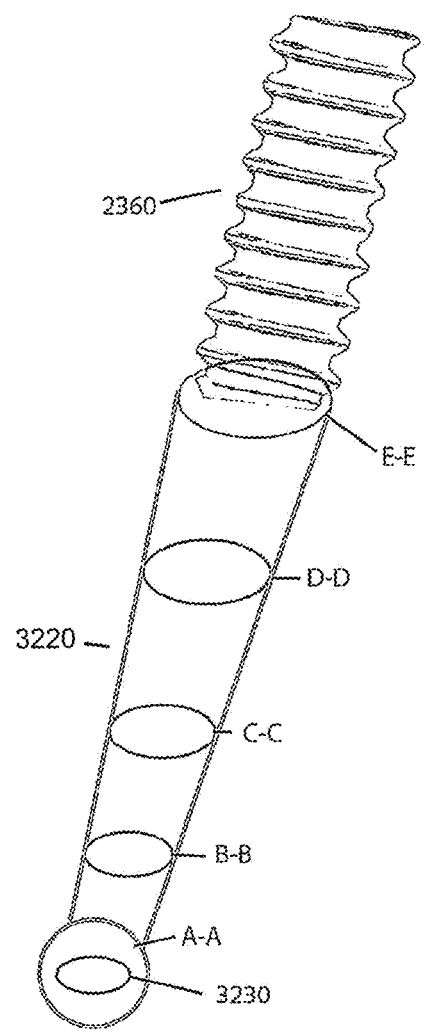

FIG. 34A illustrates a prospective view of another aspect of a variable resistance beam in accordance with the principles of the invention.

FIG. 34B illustrates a multi-sectional cross sectional view of the VRB shown in FIG. 34A.

It is to be understood that the figures and descriptions of the present invention described herein have been simplified to illustrate the elements that are relevant for a clear understanding of the present invention, while eliminating, for purposes of clarity many other elements. However, because these elements are well-known in the art, and because they do not facilitate a better understanding of the present invention, a discussion of such elements is not provided herein. The disclosure herein is also directed to variations and modifications known to those skilled in the art.

DETAILED DESCRIPTION OF THE INVENTION

The object of the present invention is to adjust the flexibility and thereby the resistance of a rod by hand positioning in relationship to the fulcrum of rod; or by bending a rod and spine within the shaft; or by bending a single solid rod; or both the bending of an outer beam and an inner beam in another example. This affects the longitudinal flex and the kick or hinge point of flexure where maximum flexure bending forces arise, depending on the hand position or anchor point in relationship to the fulcrum.

A shaft includes any tube-like structure by itself, attached to the outside of another surface or incorporated within a structure. Examples of a tube-like shaft by itself include hockey sticks, golf clubs, lacrosse sticks, pole vaulting poles, fishing rods, sailboard/sailboard masts, canoe/kayak paddles or oars, baseball bats, archery bows, tennis racquets and exercise machine tensioning rods. Examples of products to which a tube-like shaft might be attached externally include skis, snowboard bindings and bicycle frames.

A beam or rod includes any solid, semi-solid or hollow elongated structure or rod, wherein the rigidity of the beam or rod is dependent at least upon the thickness of the material constructing the beam and the type of material. In the case of hollow beams or rods, the rigidity of the beam is also dependent upon the thickness of the wall forming the beam or rods and the material constructing the wall.

A spine includes any longitudinal structure whose flexure is different in one plane than another, in any increment of 0 to 90 degrees. This can be achieved using many materials. Examples of design shapes that have this property include, but are not limited to, I-beams, ovals, stars, triangles, rectangles, stacked circles, ellipses, etc. The spine may be solid or hollow in construction and utilize combinations of different materials and material thicknesses to achieve the preferred flexibility profile and characteristics.

FIG. 1 represents exemplary views and cross sections of resilient rods, beams or shafts of solid, semi-solid or hollow construction in accordance with embodiment a first aspect of the invention that produce resistance and variable resistances when orientated in a direction of x, y, z plane or combination of planes in 360 degrees of rotation or bending movement.

FIG. 1 illustrates exemplary embodiments of the invention claimed, wherein;

Type I (FIG. 1(*a*)): Non-I-Beam: includes a circular cross-section having no outside or internal diameter geometry that would create an i-beam effect: Unlike a single static rod that is intended to produce a single measurement of static resistance, fulcrum adjustable resistance is relative and proportional to hand position as indicated by an indicia zone indicated by graphics, ergonomic ridges, structures, textures and or zones of color.

Type II (FIG. 1(*b*)): I-Beam includes one of: static outside and/or internal diameter geometry or combination, thereof: I-Beam cross section geometry produces proportional adjustable resistance to rotated orientation: Geometric relationship to resistance.

Type III (FIG. 1(*c*)) (FIG. 1(*c*)): Dual I-Beam: includes rotating inner and outer I-Beam tubes with inner and/or outer geometry or combination thereof to create variable I-beam resistance.

Dual I-Beam cross section geometry rotation produces proportional adjustable resistance to rotated orientation: geometric relationship to resistance.

Type IV (FIG. 1(*d*)): Conical beam with hollow, additive or subtractive wall geometry: Conical Beam cross section geometry produces proportional adjustable resistance to rotated orientation: Geometric relationship to resistance.

Type V (FIG. 1(*e*)): Ellipsoidal beam: solid, semi-solid or hollow beam with or without outside and/or internal diameter geometry or combination, thereof along its major axis generating additional I-beam mechanics and/or subtractive, e.g., conical hollow, geometry along its minor axis. Ellipsoidal beam with a major axis that is wider than the minor axis with or without internal or external geometry along the major axis.

Type VI (FIG. 1(*f*)): Internal Spine 'I-beam' with one or more spines within a hollow cylindrical or conical shaft.

Type VII (FIG. 1(*g*)): Rectangular beam with two sides wider than the remaining two sides.

More detail description of the different embodiments of the invention are further illustrated in FIG. 1A-FIG. 1G.

Figure 1A:
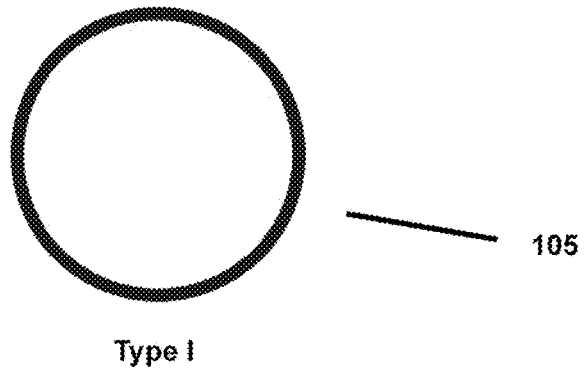
Figure 1A:
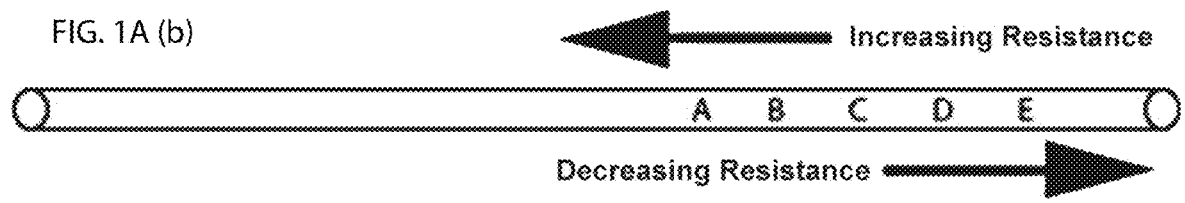
Figure 1A:
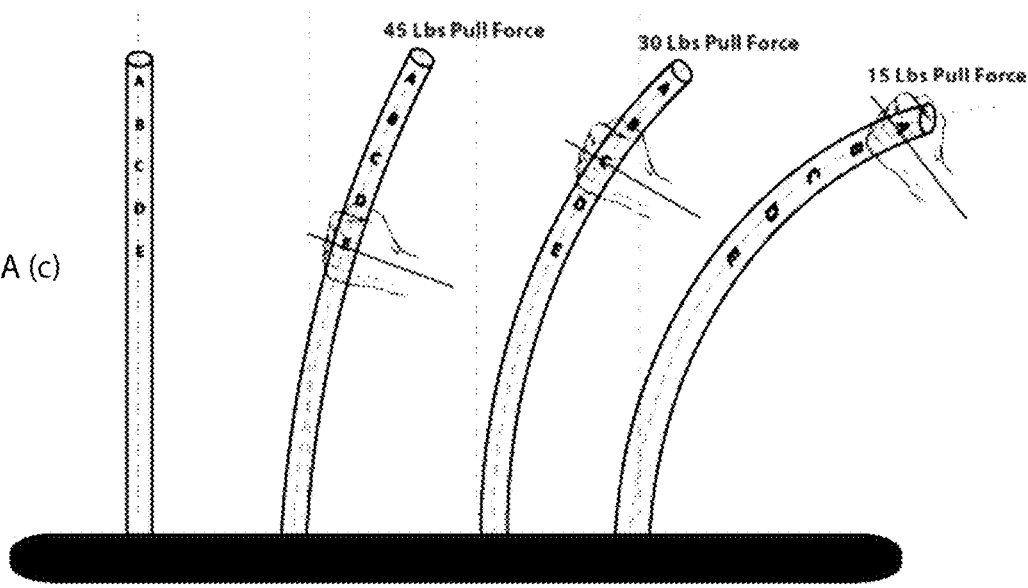

FIG. 1A (a)-(c) illustrates an exemplary embodiment of a type I VRB (variable resistance beam) 100 having a circular cross-sectional area 105. Also illustrated is a series of beams 100 having cross-sectional area 105 that demonstrate the various fulcrum changes through changing hand placement. Each new hand position provides a different resistance such that the resistance increases as a fulcrum length, from a fixed or attached point, decreases, and in the inverse, how resistance decreases as the fulcrum length increases.

Figure 1B:
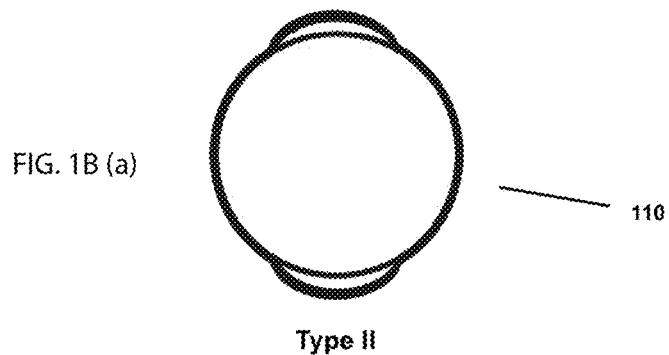
Figure 1B:
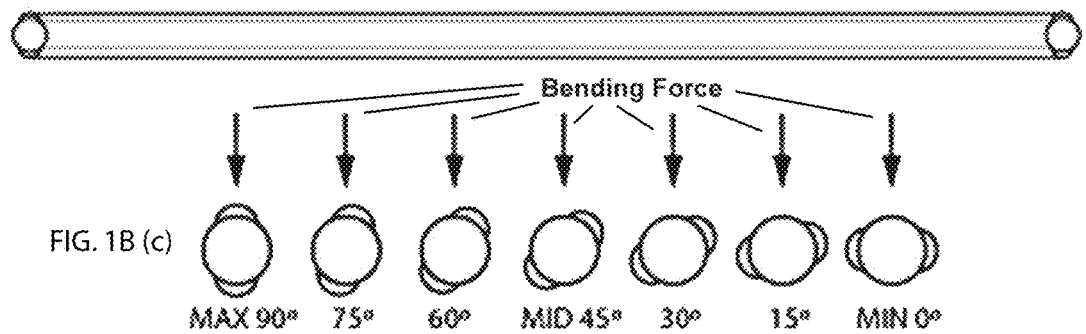
Figure 1B:
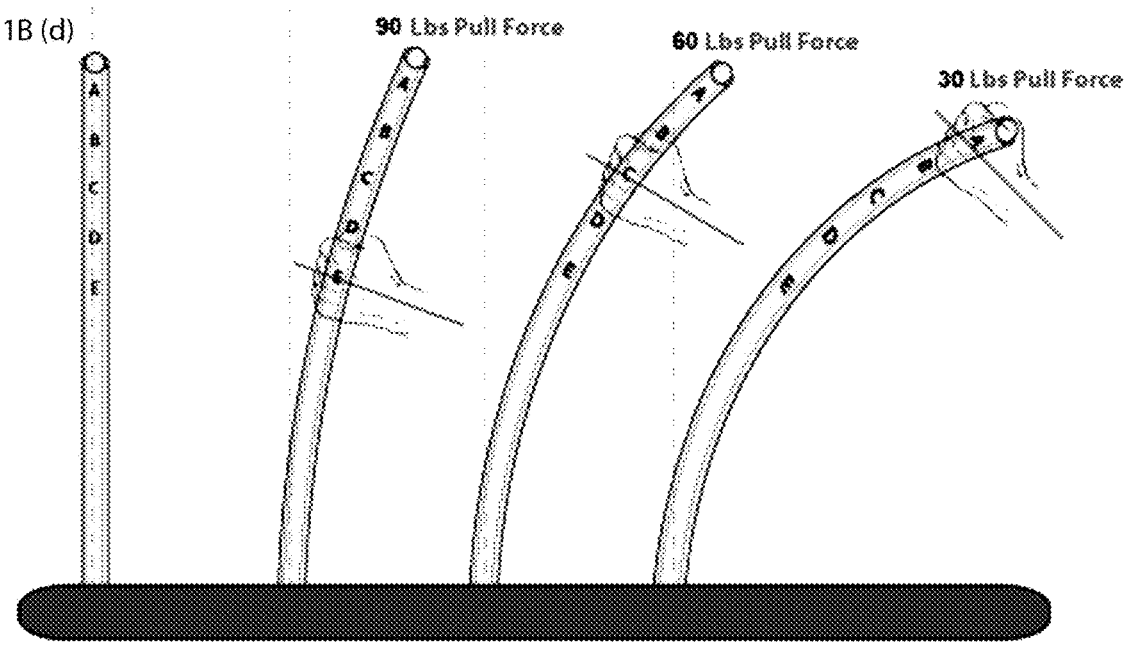

FIG. 1B (a)-(c) illustrates an exemplary embodiment of a type II VRB 100 having a circular cross-sectional area 110 including at least one outer geometric spline 112. Also illustrated is a series of beams 110 with outer geometric spines, demonstrating the various fulcrum changes through hand placement. Each new hand position provides a different resistance. Further illustrated is how the resistance increases as fulcrum length decreases, with respect to a fixed attachment point, and how resistance decreases as the fulcrum length increases.

Also illustrated is a change in the resistance of the VRB 100 having a circular cross-sectional area 110 as the orientation of the outer splines is rotated with respect to a bending force. In this illustrated example, the resistance to the bending force is maximum when the orientation of the outer splines is parallel to the bending force and minimum when the orientation of the outer splines is perpendicular to the bending force.

Figure 1C:
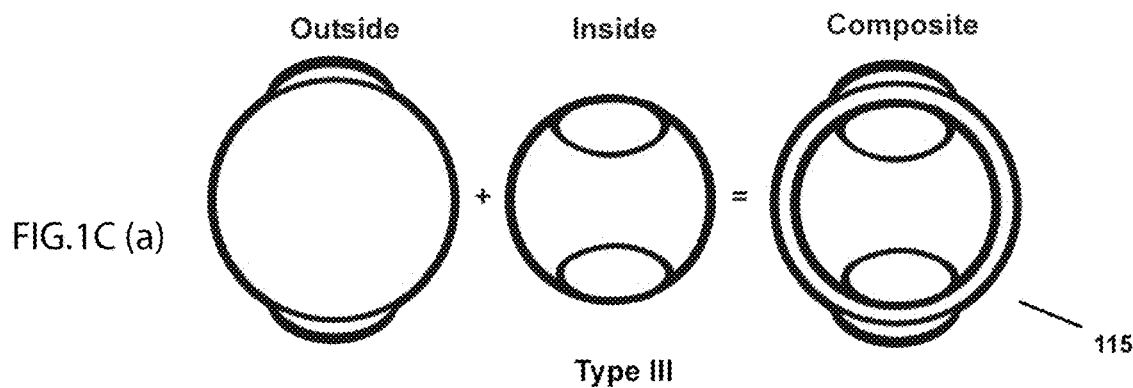
Figure 1C:
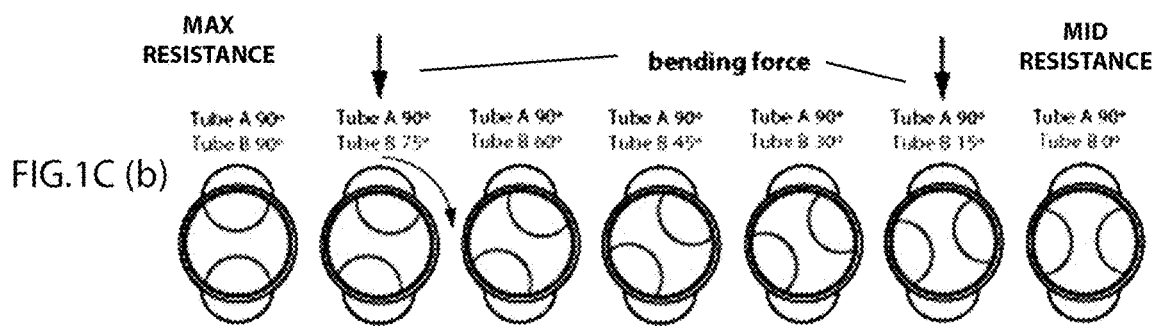
Figure 1C:
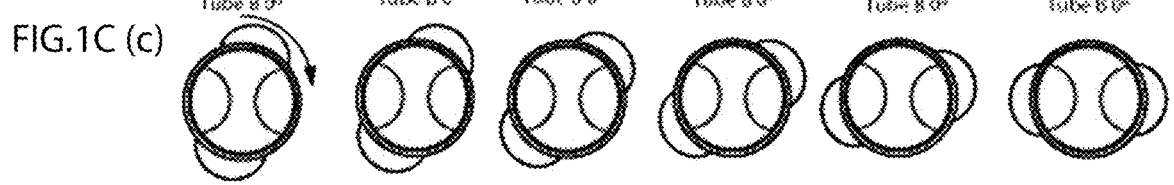
Figure 1C:
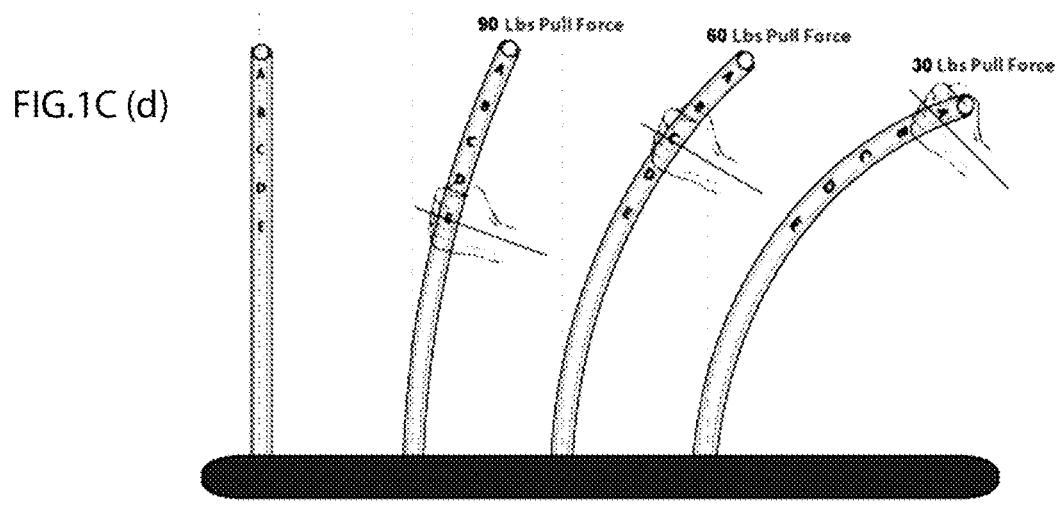

FIG. 1C(a)-(c) illustrates an exemplary embodiment of a type III VRB 100 having a cross-sectional area 115 including a combination of an outer shaft having external splines and an inner shaft having internal splines. That is, type III VRB 100 represents a hollow 2-cam cross section. Also illustrated is a series of beams with internal rods or shaft, that have geometric spines, demonstrating the various fulcrum changes through hand placement. Each new hand position provides a different resistance. Further illustrated is how the resistance increases as fulcrum length decreases with respect to a fixed attachment point, and how resistance decreases as the fulcrum length increases. With respect to the fixed attachment point. Also illustrated is a change in the resistance of the type III VRB 100 as the orientation of the inner splines is rotated with respect to a bending force. In this illustrated example, the resistance to the bending force is maximum when the orientation of the inner splines is parallel to the bending force and minimum when the orientation of the inner splines is perpendicular to the bending force.

FIG. 1D (a)-(c) illustrates an exemplary embodiment of a type IV VRB 100 wherein at least one elliptical section is removed from the cross section 120. In this illustrative example, the reference Side B represents an area within the type IV VRB 100 that is removed from the VRB. FIG. 1D further illustrates side views of type IV VRB 100 illustrating the removal of area referred to as Side B from the type IV VRB 100. Also illustrated is a type IV VRB 100, that has elliptical scallop cuts along the inner rod or shaft, demonstrating the various fulcrum changes through hand placement. Each new hand position provides a different resistance, wherein the resistance increases as a fulcrum length decreases, and decreases as the fulcrum length increases.

FIG. 1E(a)-(c) illustrates an exemplary embodiment of a type V VRB 100 having a cross-sectional area 125 comprising a major axis longer than minor axis. That is type V VRB 100 illustrates ellipsoidal beams (hollow or solid) with a major axis longer than a minor axis. Also shown is a series of type V VRB 100 demonstrating the various fulcrum changes through hand placement. Each new hand position provides a different resistance. Further illustrated is how the resistance increases as fulcrum length decreases, how resistance decreases as the fulcrum length increases.

Figure 1F:
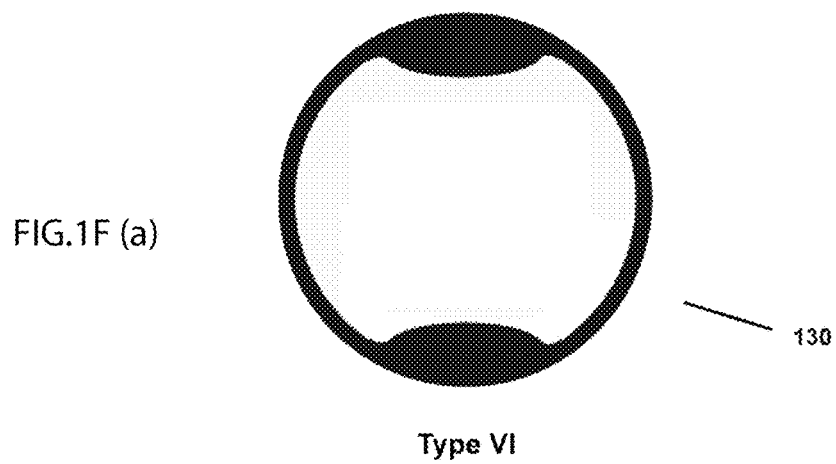
Figure 1F:
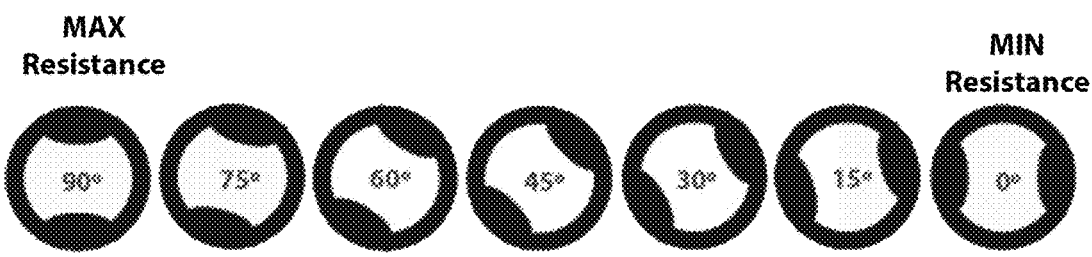
Figure 1F:
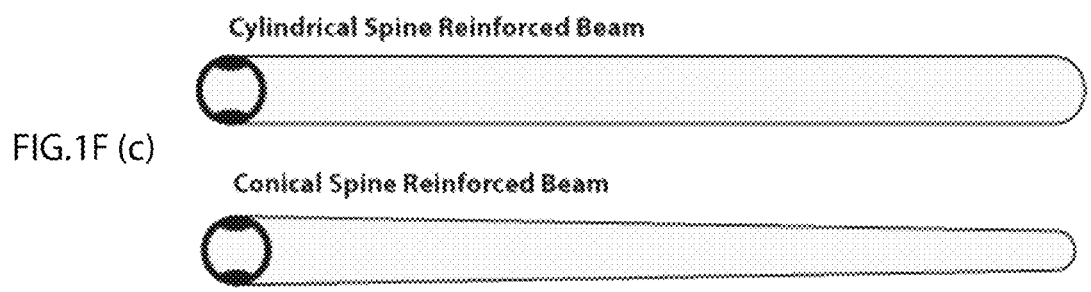
Figure 1F:
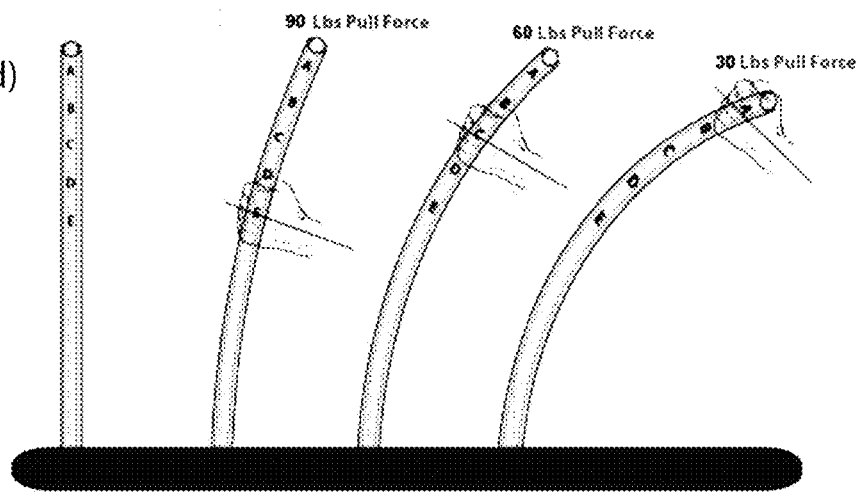

FIG. 1F (a)-(c) illustrates an exemplary embodiment of a type VI VRB 100 having a cross-sectional area 130 comprising a spine reinforced tubular or conical rod. Also illustrated is a series of type VI VRBs 100 demonstrating the various fulcrum changes through hand placement. Each new hand position provides a different resistance. Further illustrated is how the resistance increases as fulcrum length decreases, and in the inverse, how resistance decreases as the fulcrum length increases.

Also illustrated is a change in the resistance of the type VI VRBs 100 as the orientation of the inner splines is rotated with respect to a bending force. In this illustrated example, the resistance to the bending force is maximum when the orientation of the inner splines is parallel to the bending force and minimum when the orientation of the inner splines is perpendicular to the bending force.

FIG. 1F further illustrates that the type VI VRBs 100 may also be of a cylindrical or a conical shape.

FIG. 1G (a)-(d) illustrates an exemplary embodiment of a type VII VRB 100 beams having a rectangular cross-section 135. As shown the rectangular cross-section may be sized in different ratios (e.g., 4:3, 2:1) to provide different resistance to bending force. For example, in a case of a 2:1 ratio cross sectional area, the resistance to a bending force applied to the greater side is twice as great at that of the lesser side. The rectangular type VII VRB 100 may be solid or hollow as desired.

Additionally, the resistance rods (VRBs) may include a plurality of graduated indicia that indicate bending resistance by measurement of a fulcrum distance from an anchored position to a hand position[s], as shown.

Thus, in one aspect of the invention, rods with symmetrical cross sections vary their bending resistance by shortening and lengthening the arc length, from fulcrum to anchor point by hand position per indicia.

In another aspect of the invention, rods with asymmetrical cross sections may increase or decrease their bending resistance by rotation of the elongated orientation with respect to a bending force, while maintaining the same hand position or fulcrum length.

FIG. 2(a)-(f) illustrates the various fulcrum changes through hand placement. Each new hand position provides different resistances. VRB 205 illustrates the variables resistances from a cylindrical beam, rod or bar. VRB 210 illustrates the variable resistances from a type II VRB 100 beam, with added geometric spines, indicating, in this instance, the two-three times increase in pull resistance per identical hand positions along X/Y planes.

Figure 4:
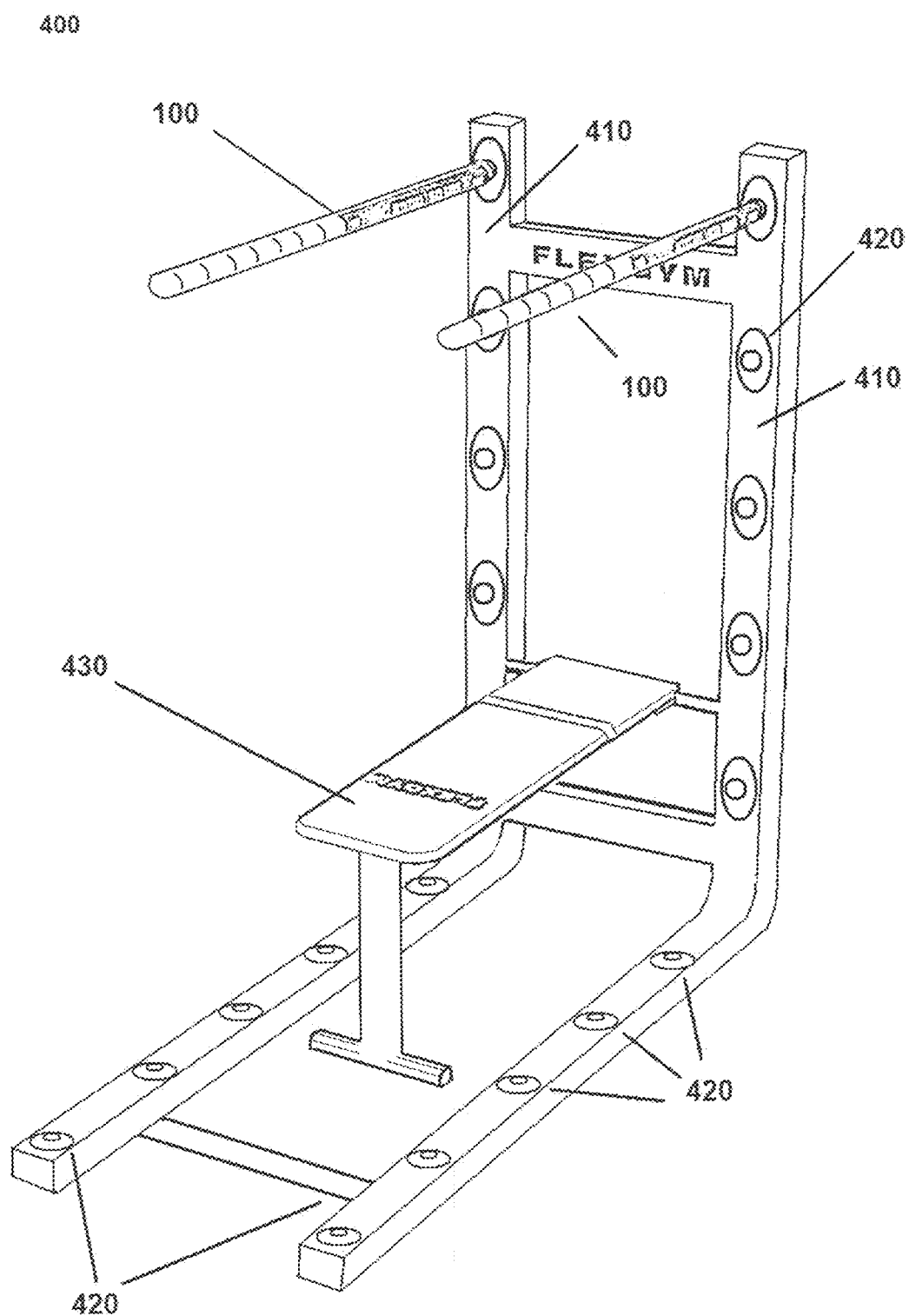
FIG. 4 illustrates an exemplary exercise system configuration in accordance with the principles of the invention that incorporate a plurality of rod holders or anchors affixed along a track or tracks that are designed for the rods to be inserted into and held in place during exercise. The rod holders are designed to increase exercise efficiency by ergonomic utility or facilitate a quick change over of rods that have a higher or lower resistance range.

Table 1 illustrates exemplary resistance levels for different configurations of the VRBs shown in FIG. 1 and FIG. 4 for a known material. In this case, resistance levels of VRB of 54 inch length, including 6 grip sections, each grip section being 3 inches for 9/16, 5/8 and 3/4 inch nominal VRBs are determined.

As shown in Table 1, the resistance level increases with the addition of a geometric spine in this example. In addition, by shortening or lengthening the arc length/fulcrum during bending of the beam the resistance may be decreased or increased.

TABLE 1

| Distance from fulcrum | 9/16 inch thick bar | | 5/8 inch thick bar | | 3/4 inch thick bar |
|---|---|---|---|---|---|
| | No Spine | With Spine Min/Max Res | No Spine | With Spine Min/Max Res | No Spine |
| 51 | 7 | 8/15 | 10 | 11/21 | 22 |
| 48 | 8 | 8/16 | 11 | 12/23 | 24 |
| 45 | 9 | 9/18 | 13 | 14/25 | 26 |
| 42 | 10 | 10/20 | 14 | 15/28 | 29 |
| 30 | 11 | 11/22 | 16 | 17/32 | 33 |
| 36 | 12 | 13/26 | 18 | 20/37 | 38 |

Also shown, the resistance level increases as the material thickness increases. In addition, the resistance level increases from a minimum to a maximum value as the orientation of the spine with respect to the direction of the flex increases.

Hence, the resistance level that may be achieved at each hand level depends on the thickness of the VRB and the material composing the VRB. Although not shown it would be recognized that the resistance level may further be based on whether the VRB is hollow. With a hollow VRB, the resistance of the VRB depends on a thickness of the outer wall of the VRB.

Figure 2:
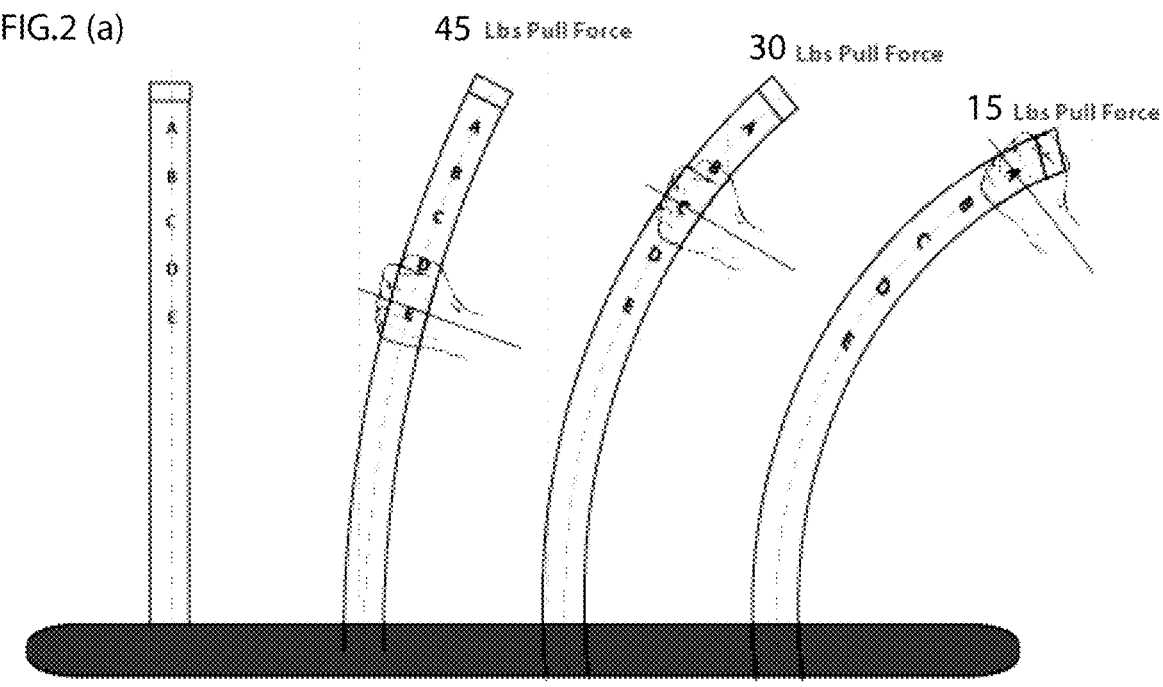
FIG. 2(a) and FIG. 2(b) illustrate a comparison of a symmetric or basically round and an asymmetric or elongated cross sectional resistances generated by each type of rod with the same hand position indicia.
Figure 2:
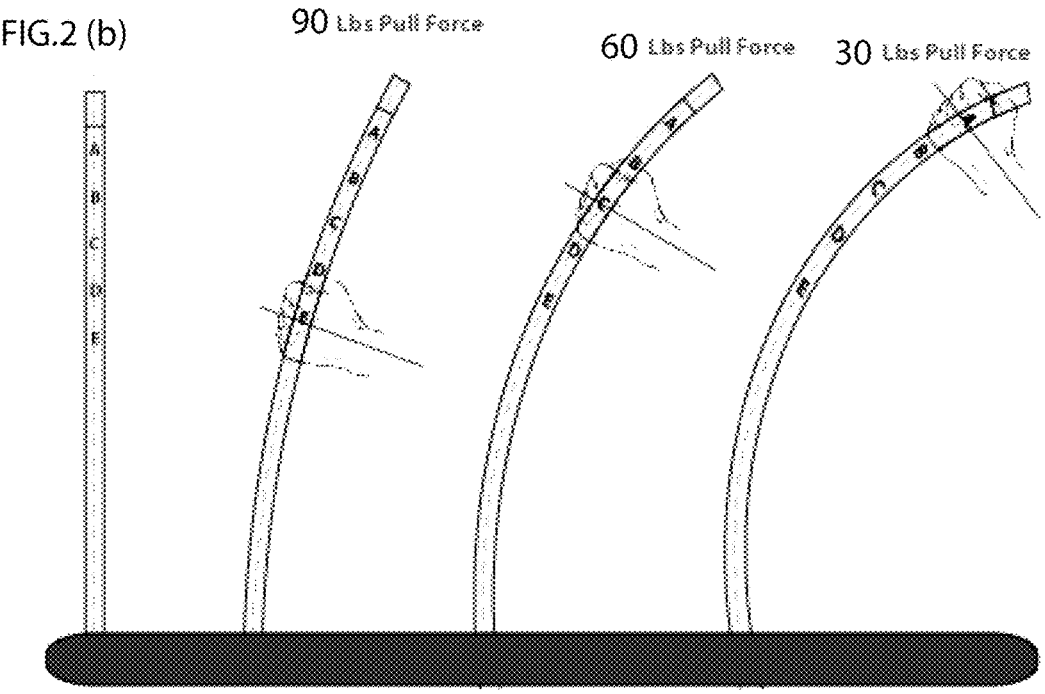

FIG. 2A(a)-(f) Illustrates a comparison of a symmetric or basically round and or an asymmetric or elongated cross sectional VRB 100 rod held at two positions. Increasing or decreasing resistance is generated by each rod with a fixed or anchored hand position 215 and a moving hand position 220 into each indicia zone. This distance between fixed hand position and the moving hand position is described as the fulcrum length.

As the fulcrum length or distance between the fixed hand position 215 and the moving hand position 220 increases, the resistance decreases. As the distance between the anchored hand position and the moving hand position decreases, resistance increases.

FIG. 3(a)-(c) illustrates a VRB 100 with an outside diameter with marked sets of indicia that specify the range of flexural resistances proportionate to the tensile strength of the beam material and fulcrum length per hand position[s] for symmetric or basically round (1 set) and (2 set) asymmetric or elongated cross sections.

FIG. 3 (a)-(c) illustrates a side view 300 of an exemplary embodiment of a VRB 100 in accordance with the principles of the invention. In this illustrative embodiment, a symmetric VRB 100 may include a plurality of hand positions 315, which indicate one set of resistance ranges in relationship to the fulcrum point. An asymmetric VRB 100, it may include a plurality of hand positions 310, which indicate two sets or multiple levels of resistance ranges in relationship to the fulcrum point and rotated orientation.

FIG. 4 illustrates a view of an exemplary embodiment 400 of an equipment incorporating a VRB 100 in accordance with the principles of the invention. In this illustrative embodiment, a VRB 100 can be inserted into a plurality of insertion points or rod holders 420. The exercise equipment includes a plurality of tracks 410, a plurality of rod holders 420, a bench 430 that may be positioned substantially perpendicular to the plurality of tracks 410 or at an incline angle with respect to the plurality of tracks.

The tracks may be mechanically fixed in vertical or horizontal planes or any combination to maximize rod bend, defined as mechanical work or exercise matched to human proportion or otherwise described as the ergonomic interface.

Figure 5:
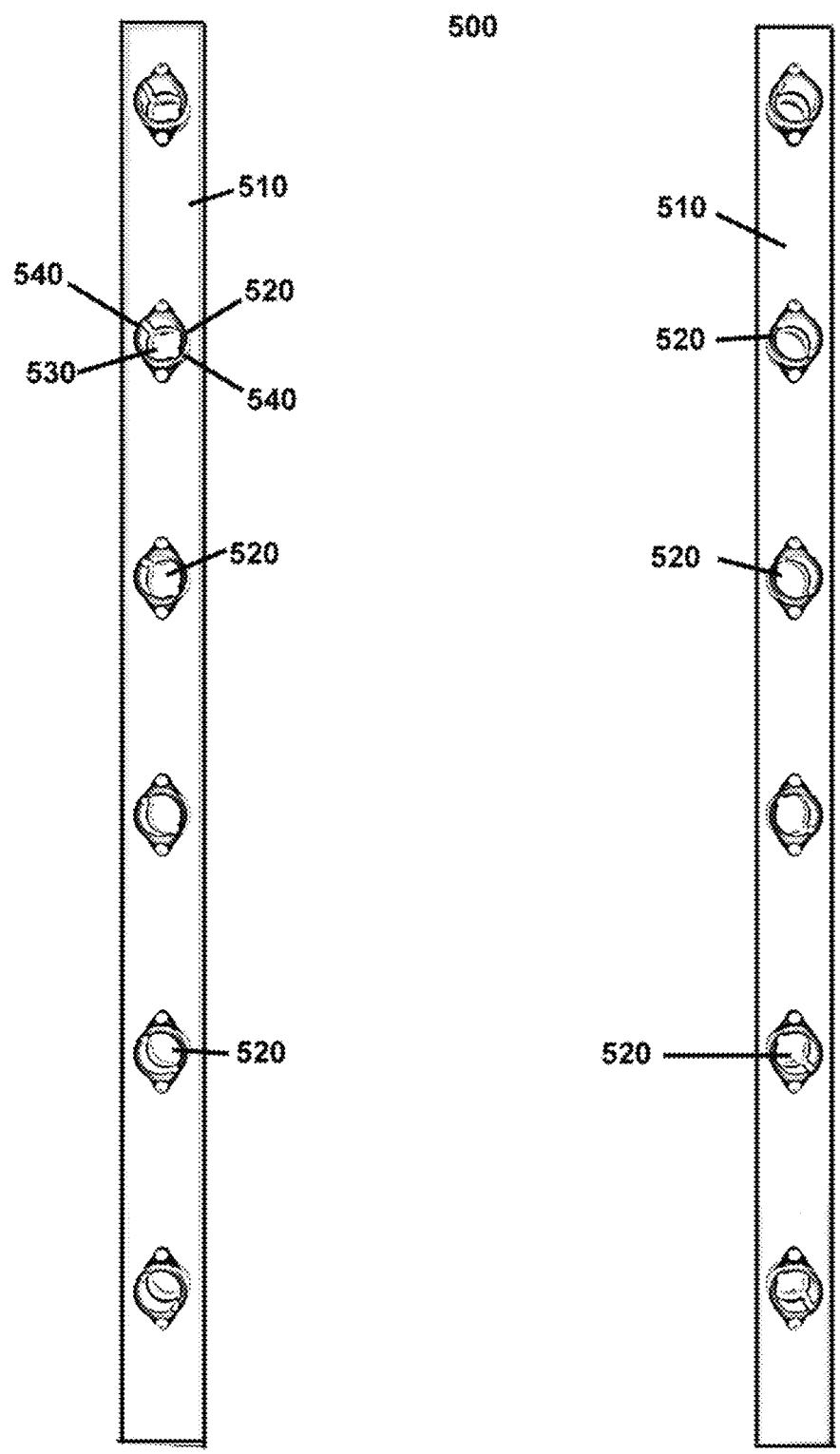
FIG. 5 illustrates an exemplary exercise system configuration of linear rigid tracks affixed with a plurality rod holders designed for the rods to be inserted into and held in place during exercise.

FIG. 5 illustrates a view of an exemplary embodiment of an equipment 500 in accordance with the principles of the invention. In this illustrative embodiment, a VRB 100 can be inserted into a plurality of insertion points. The equipment 510 includes at least one track, which can be wall or floor mounted. Each of the at least one tracks includes rod holders 520. In addition, the walls 530 of the rod holder may be perpendicular or conical with respect to the track 510. Rod holders 520 may further include a stabilizing foot 540 in contact with track 510.

The anchored resistance rod (VRB) generates increased or decreased resistance by anchoring the rod at its base and therefore the user can control the degree of rod bend.

This allows the rod to be used as a dynamic resistance beam for useful exercise. The beam resistance is dependent upon the degree of bend and hand position.

Figure 6:
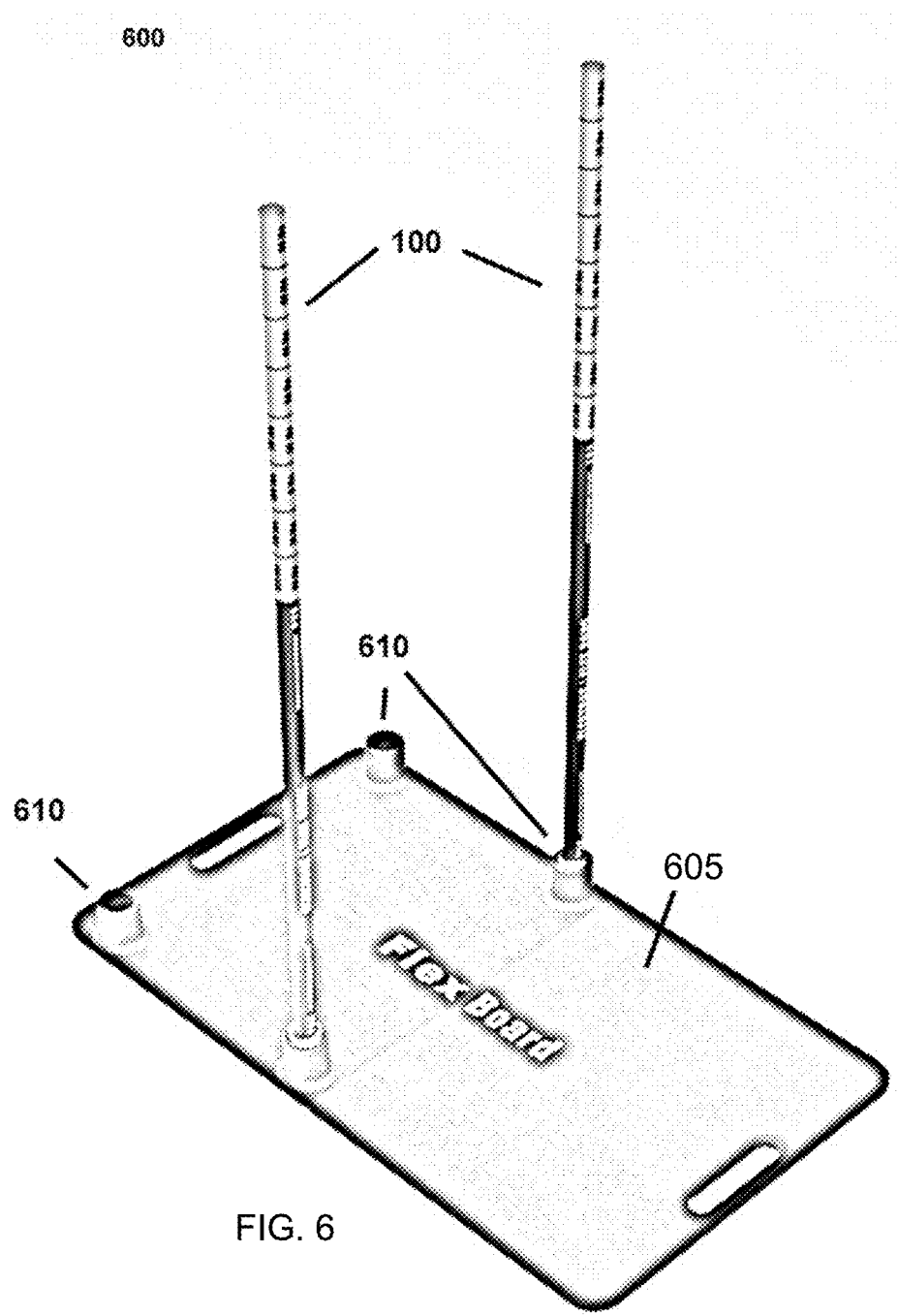
FIG. 6 illustrates an exemplary and portable exercise system configuration in accordance with the principles of the invention comprised of a folding flat workout surface, with a plurality of perpendicular rod holders designed for the rods to be inserted into and held in place during standing exercises.

FIG. 6 illustrates a view of an exemplary equipment 600 in accordance with the principles of the invention. In this illustrative embodiment, a VRB 100 can be inserted into selected ones of a plurality of insertion points 610. In this exemplary embodiment, a plurality of perpendicular rod holders or insertion points 610, similar to those described with regard to FIG. 5, may be incorporated onto a handheld transportable folding workout platform 600.

Figure 7:
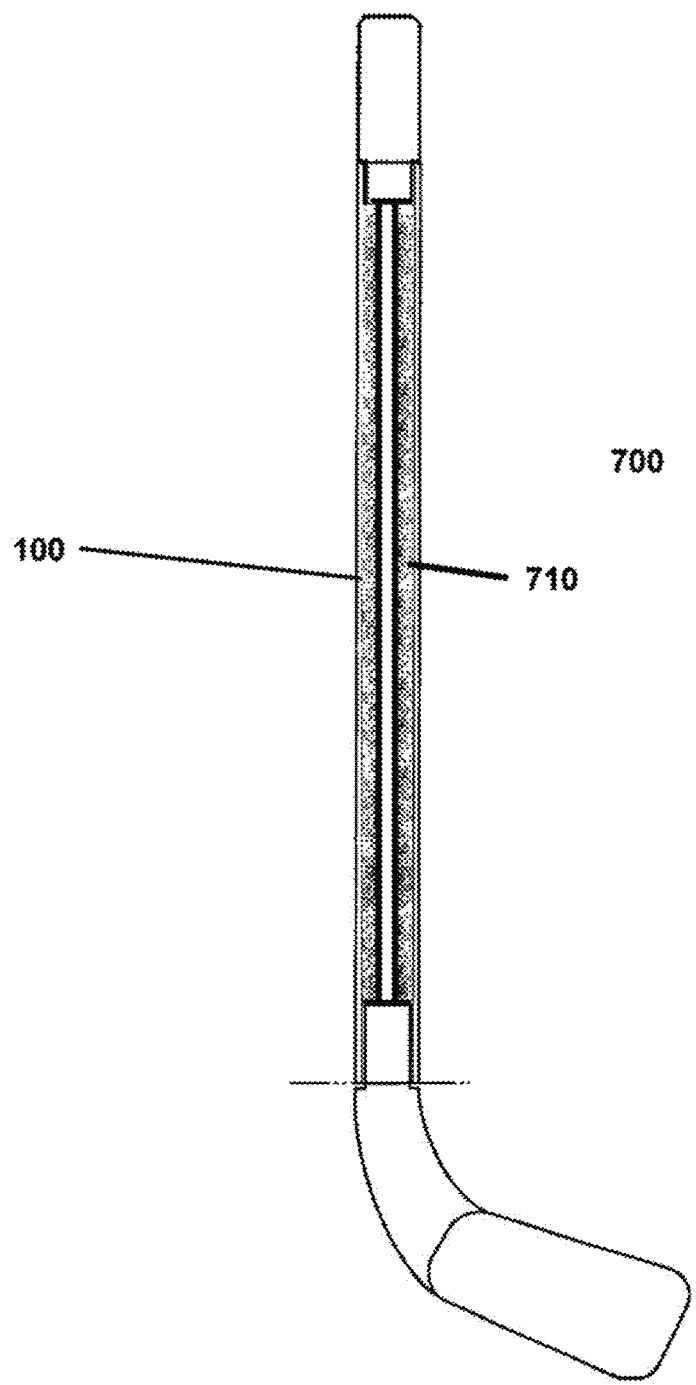
FIG. 7 illustrates an exemplary sports equipment configuration for a resistance beam centrally located within a solid wooden or hollow aluminum or graphite shaft of a hockey stick in accordance with the principles of the invention.

FIG. 7 illustrates a view of an exemplary equipment 700 in accordance with the principles of the invention. In this illustrative embodiment, a VRB 100 held in place by foam or other lightweight material 710 within a hollow shaft 720. The position and/or orientation of the VRB 100 within the hollow shaft 720 may determine the stiffness and/or flexibility of the hollow shaft. That is, in the case, a type I VRB 100 is incorporated into the hollow shaft 720, the length of the type I VRB 100 may determine the stiffness of the hollow shaft. On the other hand, if a type II VRB 100 is incorporated into the hollow shaft, then the orientation of the splines to a proposed bending force determines the stiffness and/or flexibility of the hollow shaft 720.

The resistance beam upon manual customized selected rotation imparts greater flexibility or rigidity to the hockey stick by the user, to customize the equipment's response to the user's athletic ability.

Additionally, another method of imparting greater flexibility or rigidity is to raise or lower the resistance beam within the shaft to change the fulcrum or kick point of the stick.

Figure 8:
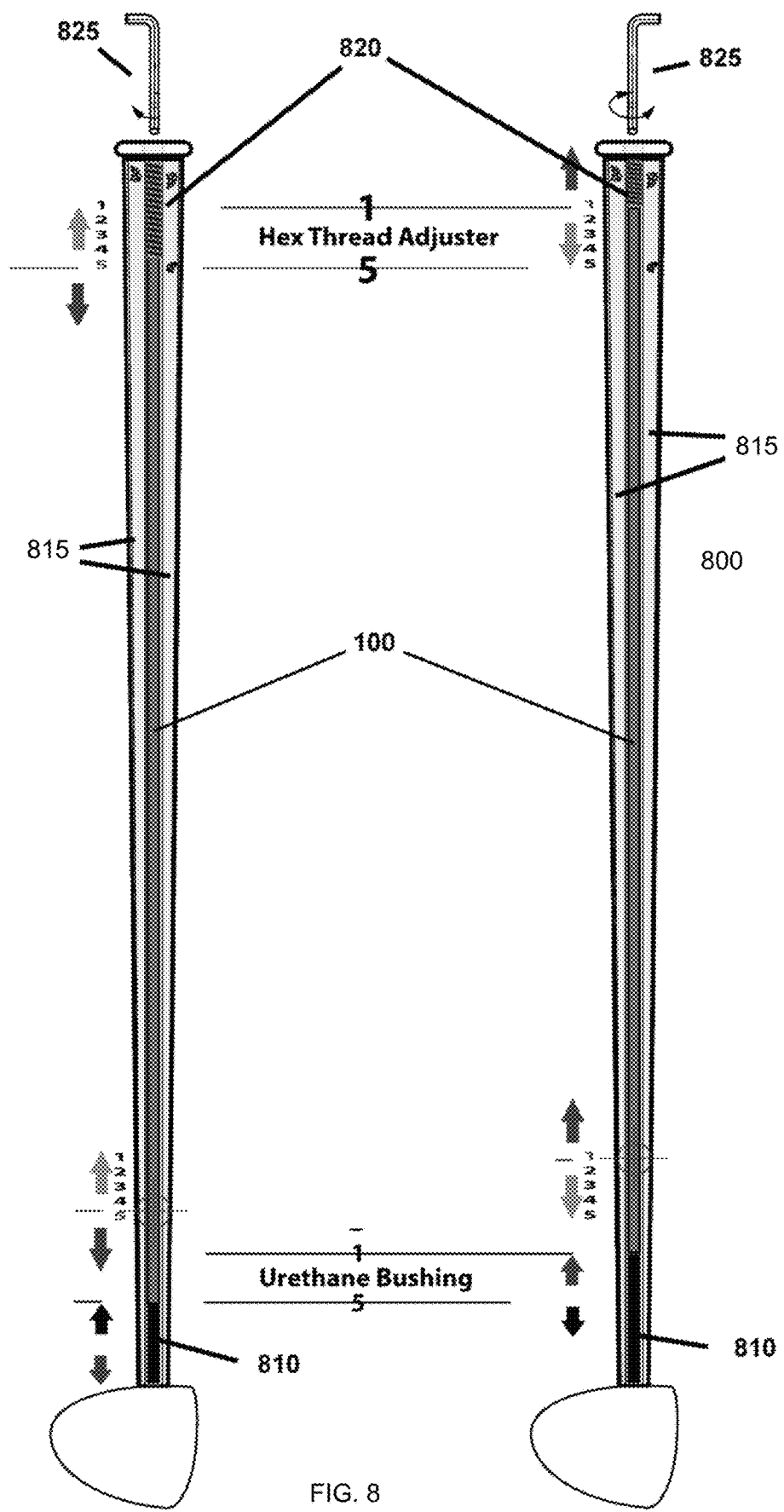
FIG. 8 illustrates an exemplary beam mechanically positioned centrally within a golf shaft configuration in accordance with the principles of the invention.

FIG. 8 illustrates a view of an exemplary embodiment of an equipment 800 in accordance with the principles of the invention. In this illustrative embodiment, an internal VRB 100 is held in position within a hollow shaft by a lightweight material 815, as described with regard to FIG. 7. In addition, one end of the VRB 100 is positioned on a bushing 810 comprising a flexible material such that it may compress or expand as pressure is applied to the bushing 810. In one aspect of the invention, the bushing may be made of an elastomeric material such as a polymer, foam, urethane, rubber, or so the similar material that may be compressed and returned to an original state when the compressive force is removed. At a second end, the VRB 100 is attached to a means 820 for raising or lowering the VRB within the hollow shaft. The means 820 may be a worm gear type mechanism that raises or lowers the VRB 100, to create a variable shaft flex. The VRB 100 may be lowered by compressing the bushing material 810 and raised by removing the compression pressure from the bushing material 810. Although the means for positioning the VRB 100 is shown as a worm gear that may be turned by an Allen key, it would be recognized that other types of rotating means may be incorporated without altering the scope of the invention. For example, the means for adjustment to alter the position of the VRB 100 may be a screw thread position along the outside of the hollow shaft and the turning of a cap on the top of the hollow shaft may lower or raise the VRB 100.

In the illustrated embodiment of the invention shown herein, a VRB 100 rod is centrally raised or lowered within the hollow shaft to increase or decrease flexibility or rigidity of the golf shaft, thereby shifting the kick point or maximum point of flexure up or down the hollow section of the shaft.

Thus, the player or user may select a shaft flex or rigidity range that matches the player's specific swing type, strength and ability.

The 360 degree symmetrical geometry provides a solution for an adjustable golf club and would be fully compliant with the existing USGA (United States Golf Association) rules of golf.

Figure 9:
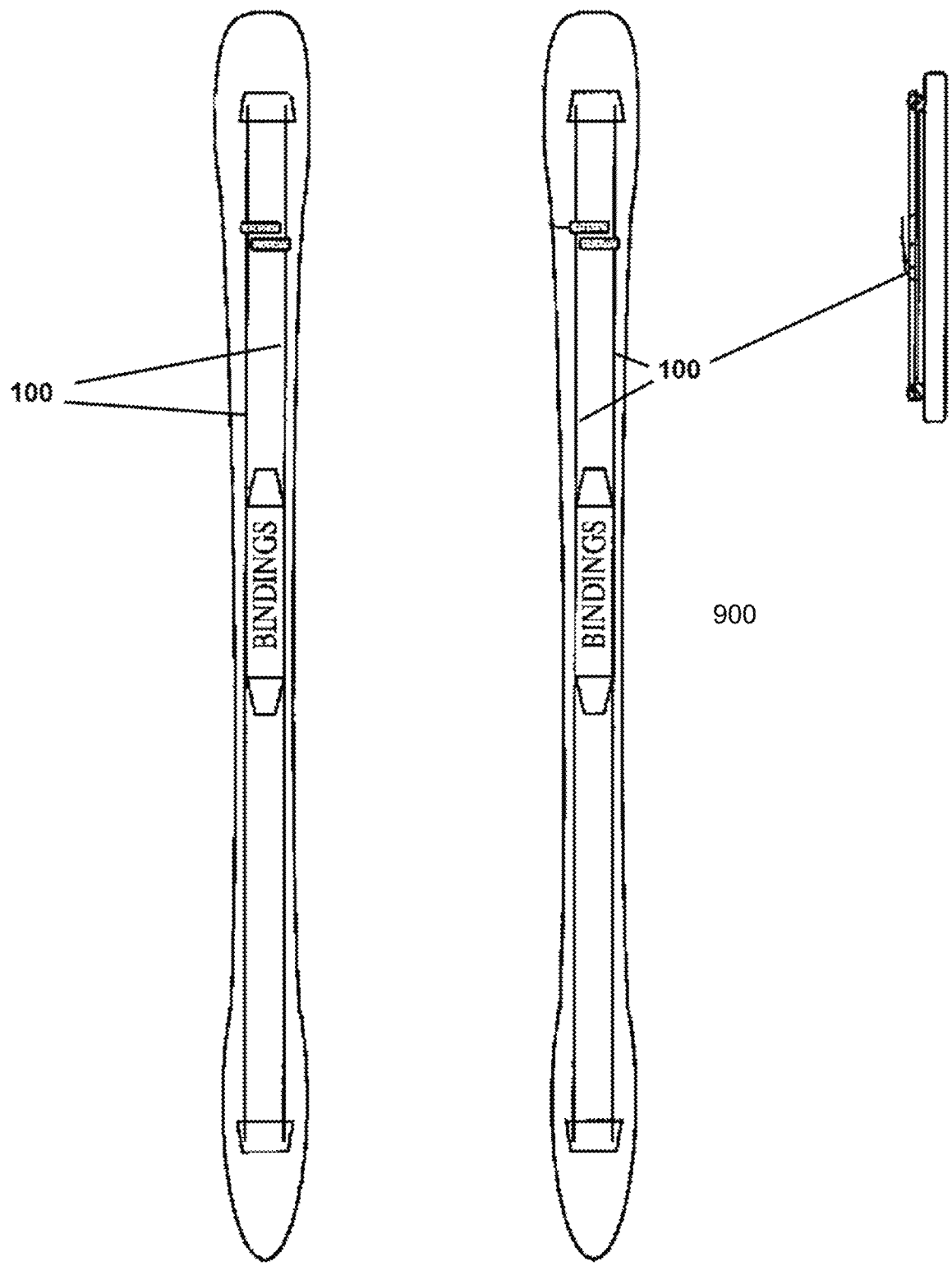
FIG. 9 illustrates an exemplary ski sports equipment configuration with an adjustable resistance beam that imparts a resistance range along the length of the body of the ski in accordance with the principles of the invention.

FIG. 9 illustrates an exemplary ski sports equipment configuration 900 with an adjustable resistance beam VRB 100 that imparts a resistance range along a length of the body of the ski in accordance with the principles of the invention.

The adjustable resistance beam VRB 100 imparts a range of performance characteristics into the ski to match the skier's skill and terrain requirements.

In one application of the VRB described herein, downhill skiing requires a very rigid ski. By adjusting the resistance beam to the highest rigidity setting, the ski will become more rigid with a faster dynamic response when carving turns. A more rigid ski is desirable for icy conditions due to the ability to hold its shape and maintain maximum edge contact with the snow and ice surface.

In another application, mogul skiing over bumps requires a flexible ski. By adjusting the resistance beam to its most flexible setting, the ski will become more conformal to bumps and bend and flex over them.

Thus a terrain adaptable ski is created from a mechanically joined adjustable resistance beam.

The means for positioning the VRB 100 may be similar to that described with regard to FIG. 8.

Figure 10A:
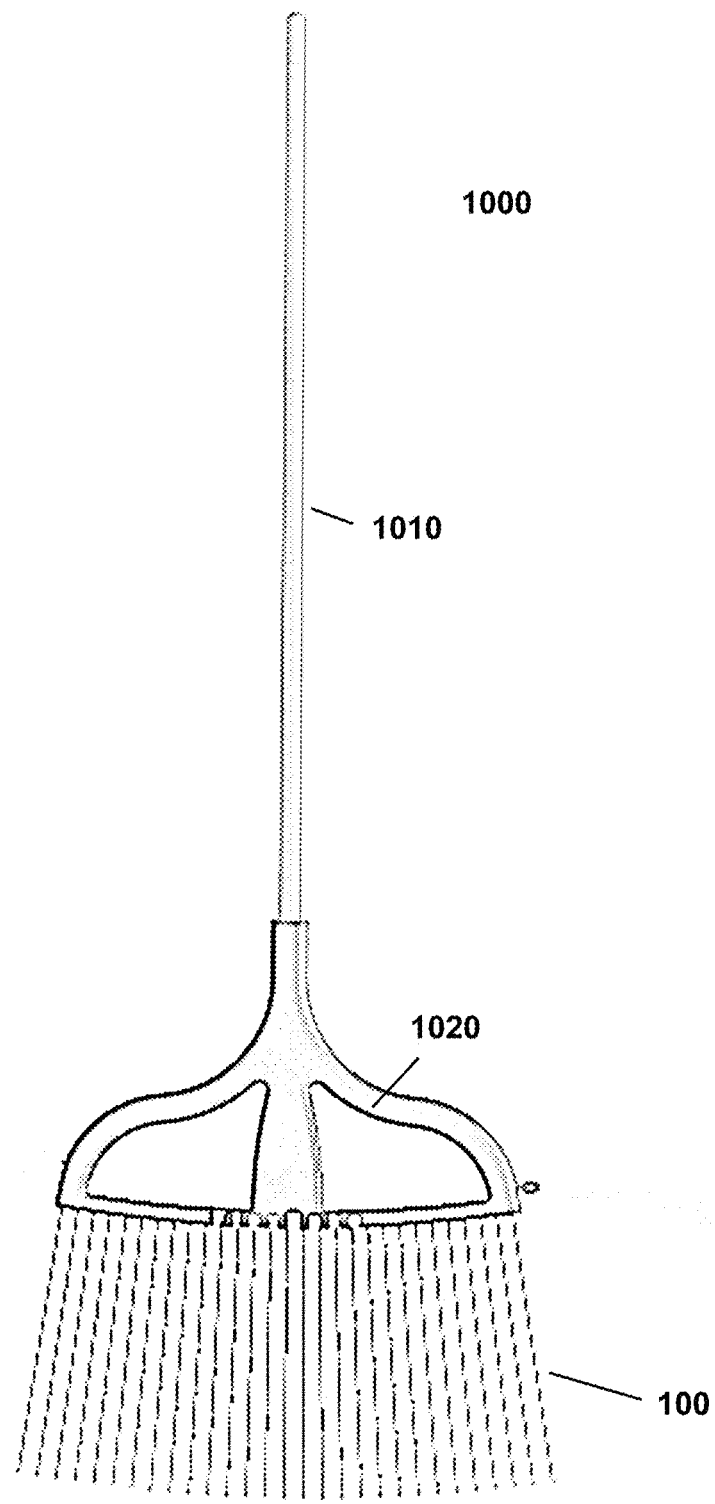
FIG. 10A-FIG. 10B illustrate exemplary configurations of a lawn device configured in accordance with the principles of the invention. The tines of this adjustable flex rake are individual resistance beams that are simultaneously rotated.

FIG. 10A illustrates a view of an exemplary embodiment of a lawn equipment 1000 in accordance with the principles of the invention. In this illustrative embodiment, tines are individual VRBs 100, and can be simultaneously adjusted to create equal flex in each tine.

Figure 10B:
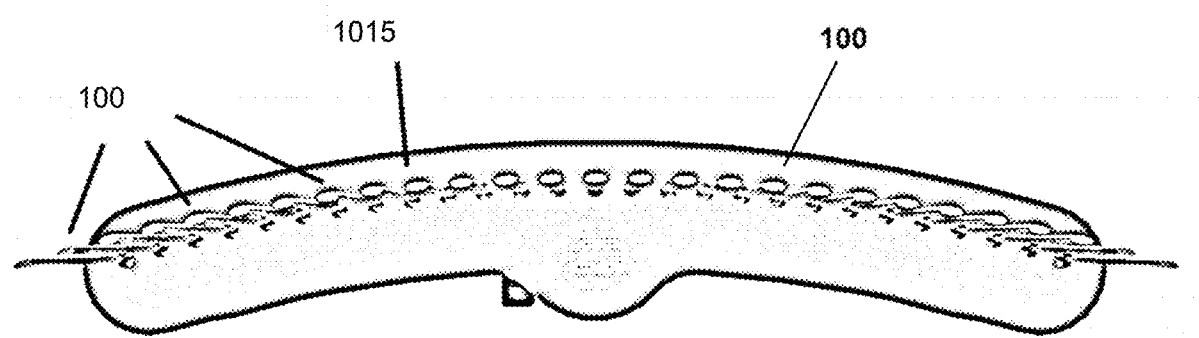

FIG. 10B illustrates a bottom view of an exemplary embodiment of a lawn equipment 1000 in accordance with the principles of the invention. In this illustrative embodiment, the tines VRB 100 may be simultaneously rotated equally to create variable flex.

The rotated tines are locked into an incremental range of resistance positions that are either the most flexible for raking leaves or the most rigid to raking gravel. At the end of each tine is an ellipse that acts a hook dependent upon its rotated orientation.

Figure 11:
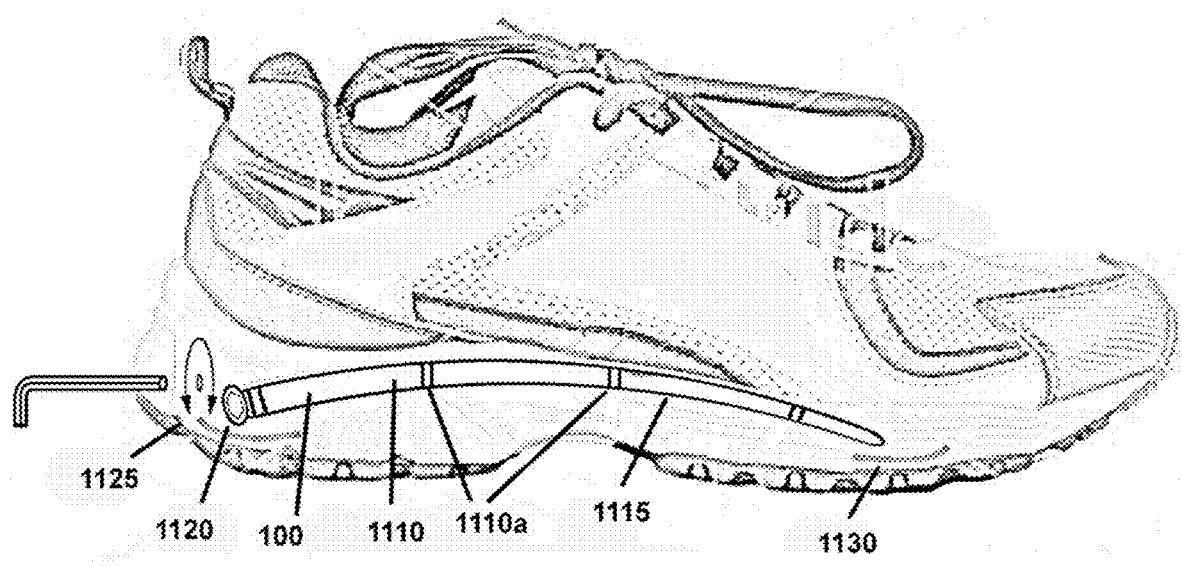
FIG. 11 illustrates an exemplary adjustable active suspension system configuration for sports footwear in accordance with the principles of the invention.

FIG. 11 illustrates a view of an exemplary embodiment of an equipment 1100 in accordance with the principles of the invention. In this illustrative embodiment, internal VRBs 100 are adjusted to create a variable flex. Equipment 1100, which represents an athletic shoe, includes a rubber shoe sole 1115. The athletic shoe 1100 further includes a heel fulcrum 1125 and a toe fulcrum 1130. Between the heel fulcrum 1125 and the toe fulcrum 1130 is an internal cavity 1110. Within cavity 1110 is positioned at least one VRB 100. The VRB 100 includes anti-rollover collars 1110a, which prevent the VRB beam deflection or distortion and are spaced along the VRB 100. The at least one VRB 100 located within the internal cavity 1110 may be adjusted by an adjustment means 1120 that rotates the VRB within cavity 1100. The VRB 100 is further locked in position. The means for positioning the VRB may be similar to that described with regard to FIG. 8.

The transmission of the shoe wearer's strength (power) from their legs into the ground is directly affected by the sole stiffness of the shoe. By employing an adjustable resistance beam as described herein, runners may gain more leverage and, thus more speed, by using a responsive shoe sole customized to their specific requirements.

An adjustable pair of resistance beams within the shoe sole may be insertable, insert molded or structurally connected to the shoe sole in lateral and/or longitudinal positions within the sole and are rotatable to a fixed and mechanically locked position to effect custom flexural resistance range that matches the wearer's optimum performance requirement.

Thus, the resistance beam technology described herein is designed to be a dynamic, adjustable, in-sole suspension system that can absorb the weight of the wearer and release it per each step.

In accordance with the principles of the invention, a VRB footwear suspension support system to provide selectable suspension support may be incorporated into the sole of footwear to provide adjustable support in quadrant zones of the footwear is disclosed.

The VRB footwear suspension support system supports the zones of the foot from the VRBs dynamic, reactive, selective resistance to loading and unloading, resulting in dynamic suspension per one or more zones, e.g. mid arch et al, providing vertical lift from the VRB cantilever to maintain physiologic support with bio-mechanic balance and comfort.

The VRB footwear suspension support system platform effectively maps the differential loading points with resistance or suspension levels of the foot per zone and compensates with reactive support that can be selectively increased or decreased to match any podiatry foot condition or performance enhancement for sports or extreme physical activity, e.g. military, where the wearer's loads are often variable.

The VRB footwear suspension support system platform acts as a type of selectable leaf spring suspension in multiple zones, a cat's paw or multi-zone cantilever in the shape of an 'X' to combine variable resistance settings and/or height geometry from VRB dynamic suspension. This reactive system vertically 'reacts' or lifts body weight loads placed upon its surface per zone, to maintain and respond to proportionate bio-mechanical foot balance loading and therefore comfort or pain relief, with athletic enhancement.

In conjunction with a dedicated mid arch zone or individual VRB arch structure integrated with the footwear cat's paw or X platform with up to four (4) VRBs to create a completely multi-zone adjustable and dynamically supportive footwear.

The reactive, dynamic and selective support levels of the footwear zones with VRBs are a function of the VRBs inclination angle, length and width, material tensile strength or fulcrum position in relation to the underside of the foot loading, and/or extension from within shoe sole. Additionally, selectable resistance in conjunction with different variable footwear shell geometries provides a wider prescriptive resistance range to match heavier bodyweights, severe in-field operating requirements, and/or corrective foot conditions.

In accordance with the principles of the invention, the VRB footwear suspension support system platform and mid arch flex with the VRB so as to provide responsive dynamic and zoned suspension support with conformal geometry mapped to foot loading. The suspension platform maximizes surface area by distributing loads over a greater area, with a responsive and dynamic conformal surface to support the loads in real time and proportion.

Additionally, by extending the length of one or more VRBs, the VRBs become extendable into one or more of the four (4) quadrant zones of the shoe to impart selectable dynamic responsive support to the bio-mechanic loads placed upon the suspension platform. A single VRB may act as a dual cantilever to support two different support zones or structures, e.g. a VRB may support the foot arch and rearward heel zone by one or more fulcrums or 'stops' placed along the VRB length to impart calculated, and therefore, selectable cantilevered suspension to dual zones.

In accordance with the principles of the invention, a VRB acting as a cantilever provides dynamic arch support over a selectable range to match a wearer's biomechanics corrective requirement with comfort. If a prescriptive setting is initially too stiff, hard or uncomfortable for the wearer, a lower VRB setting may be used to allow the wearer 'break-in' time for re-alignment processes of the foot structures to correct, thus maximizing comfort with prescriptive benefit and enhanced customized athletic performance.

Additionally, one or more VRBs are extendable into each of the 4 quadrant zones of the shoe to impart selectable dynamic responsive support to reduce the 'break-in' period for the shoe, increasing comfort.

The VRB selectable support range provides for a range of loads that controls the supportive flexure of footwear. This in turn provides reactive geometry that will flex in proportion to the VRB setting and therefore impart dynamic support proportional to loading.

In accordance with the principles of the invention, the zone loading and/or mid arch loading and, therefore, the VRB loading curve[s] or the quantified in vertical lift force in pounds (Lbs) of response to weight loads placed on the VRB extending into each shoe zone and/or mid arch shell structure are bell curved. The bio-mechanic effect of a cantilever absorbing and releasing proportional loads in a Bell Curve results in maximal comfort throughout the entire gait cycle and at each VRB resistance setting. This is an important and intended integral design engineered bio-mechanic effect of using cantilevers to dynamically support body joints, e.g. foot et al., to provide a smooth bell curve response for maximal comfort throughout the flexural VRB range.

The mechanical resistance or support of the VRB can be design engineered to correspond to any required loading curve, e.g. rehabilitative, post surgical, prophylactic, extreme sports, performance enhancement and the military for high rucksack equipment loading in pounds (Lbs). Equally, more robust VRBs can be easily incorporated into footwear to support the arch from heavy equipment loads carried via rucksack, e.g. 100 Lbs or more.

In accordance with the principles of the invention, responsive, proportioned and dynamic zone(s) of support create a self-levelling structural VRB footwear suspension support system, enhancing the wearer's athletic ability or dynamically correcting imbalances. This provides a real time, proportionately customizing footwear to support the load requirements of the foot.

The greater the load upon the foot, the greater VRB vertical suspension or resistance to compression by immediate vertical (dynamic height) lifting support. The self-leveling platform matches the dynamic loads placed upon the zones of the foot/arch in proportion to load. The VRB compression and release of load results in proportional, vertical lifting support to the arch of the foot or per zone.

The arch and zones are supported by one or more VRBs that dynamically react in direct proportion to the loads placed upon them. The VRB footwear suspension support system can be 'pre-loaded' or positioned at a higher height geometry to allow the foot to engage and proportionally compress and engage the VRB zones (mid arch, et al.) of support levels to ensure a mapping of supported structure with cantilevered resistance ranges. Each individual zone is selectable with customizable suspension range.

In accordance with the principles of the invention, the VRB technology, disclosed, herein, dynamically supports the foot, to stabilize pronation and supination mechanics, by providing customizable, dynamic, cantilever based suspension ranges with up to four or more cantilevered VRB zones of selectable resistance, to further support and correct bio-mechanical imbalances of the foot.

The unique cantilevers configuration of variable resistance beams produces a significant range of selectable performance resistance levels to match a body weight or specifically foot condition.

Additionally, the footwear platform disclosed, herein, provides selectable flex that represents an integrated anti-pronation/supination and posting mechanisms that responds to increasing medial loads by dynamic stiffening in proportioned response to body weight loading. The VRB resistance to compression or suspension is designed to be selectively increased or decreased prescriptively to maximize therapeutic benefit with comfort.

The cantilever system disclosed herein provides selectable incremental resistance to pronation/supination "on demand" to meet the needs of a wide range of patient foot imbalances, comfort requirements and podiatry conditions.

Figure 13A:
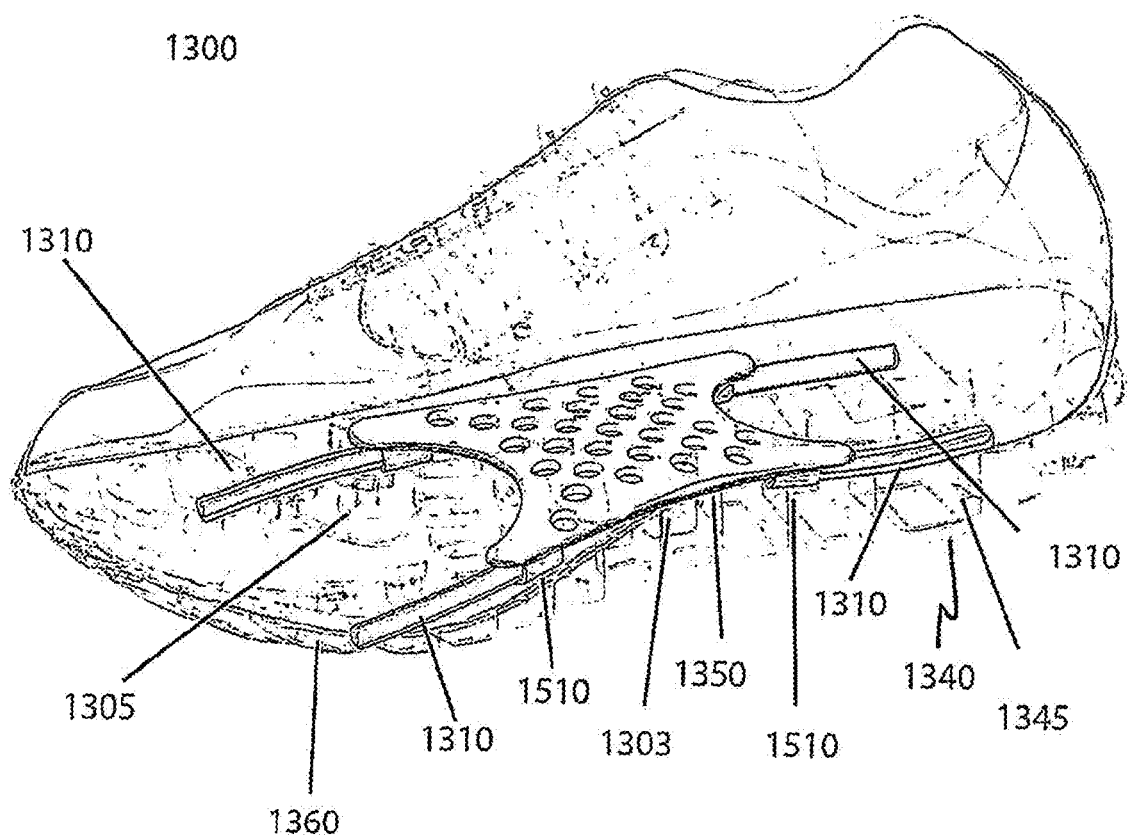
FIG. 13A-FIG. 13B illustrate perspective views of an exemplary configuration of a footwear incorporating a variable resistance (VRB) and suspension system in accordance with the principles of the invention.

FIG. 13A illustrates a perspective view of an exemplary embodiment of a VRB footwear 1300 including a VRB suspension support system 1303 in accordance with the principles of the invention.

As shown in FIG. 13A, the VRB footwear variable resistance and suspension system 1303 includes a plurality of VRBs 1310, which are inserted through heel 1340 and extend to the platform section 1350, positioned below an insole or force plate 1305 of footwear 1300.

Further illustrated is heel section 1340. Flat surface 1345 and front section 1360 rest on a same plane.

As will be discussed, the VRB 1310 comprises a generally elongated cylindrical beam or bar that includes a major axis greater than a minor axis. The orientation of the VRB 1310 with respect to platform 1350 determines a degree of flexibility (or rigidity) that supports a foot load impacting or applied to the platform 1350. The VRB 1310 may be oriented at different degrees of orientation with regard to its major axis in order to adjust the degree of flexibility (or rigidity) of platform section 1350. The degree of rotated orientation imparts a selectable resistance range per increment of rotation. For example, using an elliptical VRB, as is described with regard to FIG. 22D, in a 90° vertical or long axis position, the VRB 1310 is most rigid, while in the 0° horizontal (flat) position, VRB 1310 is most flexible. VRB 1310 operates as a cantilever to dynamically support and suspend the mid arch section 1350 with selectable resistance. In one aspect of the invention for selecting resistance, tensile strength of the material comprising VRB 1310 may be selected to affect flex performance, e.g., 1,000, 5,000, 10,000 or higher PSI Polymer tensile modulus.

As shown, VRB 1310 extends at an angle from heel section 1340 to platform section 1350 to form a cantilever upon which platform 1350 rests. As a load is applied to the platform section 1350, the platform section 1350 engages and depresses VRB 1310. Based on the orientation of VRB 1310 with respect to platform section 1350, VRB 1310 applies different levels of resistance to the force or load applied to platform section 1350.

Platform 1350 includes a plurality of pockets 1510 into which a corresponding one of VRB 1310 are captured.

Each VRB selected resistance or suspension level provides and imparts a zone of tailored bio-mechanical support to dynamically correct imbalances, e.g., Pronation/Supination/Posting of the foot, by redistributing ground reaction forces while standing, walking or running.

The biomechanics from each zone reacts by providing a smooth bell curve of support to dynamically and proportionally correct foot imbalance(s) to enhance foot performance per specific activity, e.g., weight dynamics, energy return from loading and unloading, cornering, sprinting, running, walking or to ease of locomotion.

Figure 13B:
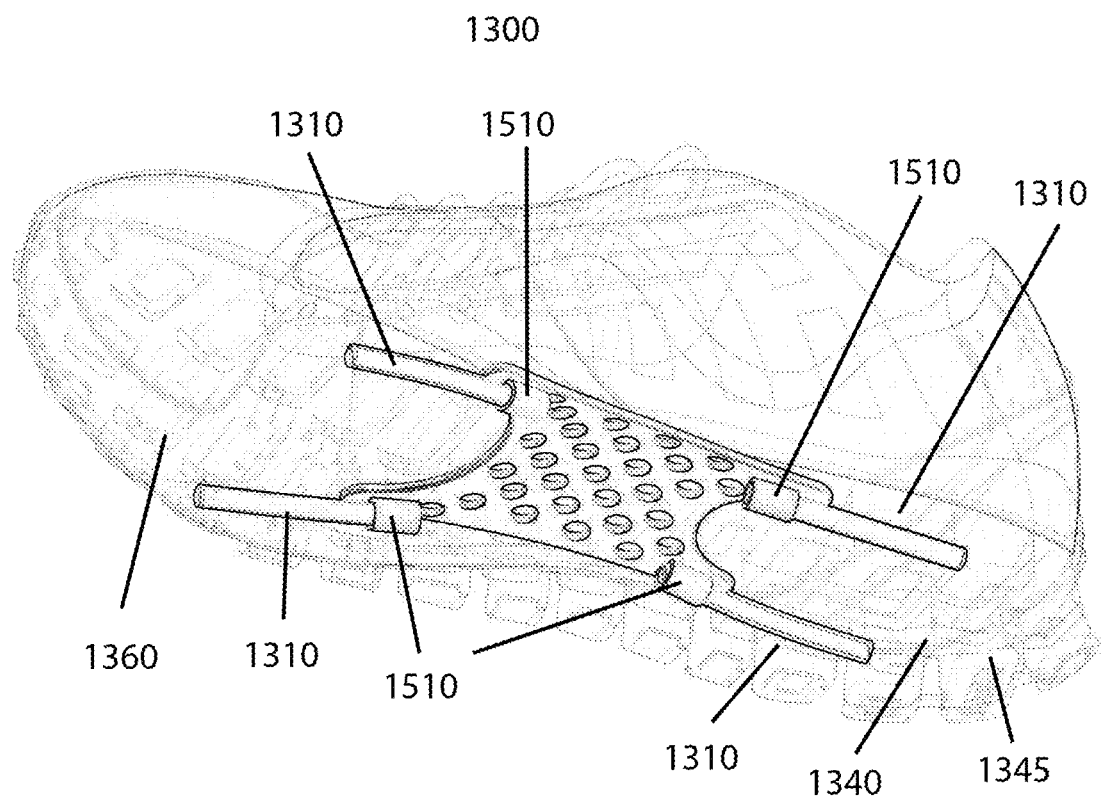

FIG. 13B illustrates a perspective, underview, of a VRB footwear suspension system 1303 in accordance with the principles of the invention.

As illustrated, VRBs 1310 extend from platform 1350, wherein the VRBs 1310 terminates in pocket 1510. Pocket 1510 captures a free end of VRB 1310, while allowing the VRB 1310 to rotate from a minimum resistive position to a maximum resistive position. As VRB 1310 rotates from a minimum resistive position to a maximum resistive position, the height of platform section 1350 is changed, while simultaneously altering the degree of support or rigidity applied to the platform section 1350.

Also illustrated in this exemplary embodiment VRBs 1310 extend from a front section 1360 to platform section 1350, wherein the VRBs 1310 terminate in pocket 1510. Pocket 1510 captures a free end of the corresponding VRB 1310, while allowing the VRB 1310 to rotate from a minimum resistive position to a maximum resistive position. As VRB 1310 rotates from a minimum resistive position to a maximum resistive position, the height of platform 1350 is changed, while simultaneously altering the degree of support or rigidity applied to the platform 1350.

Figure 13C:
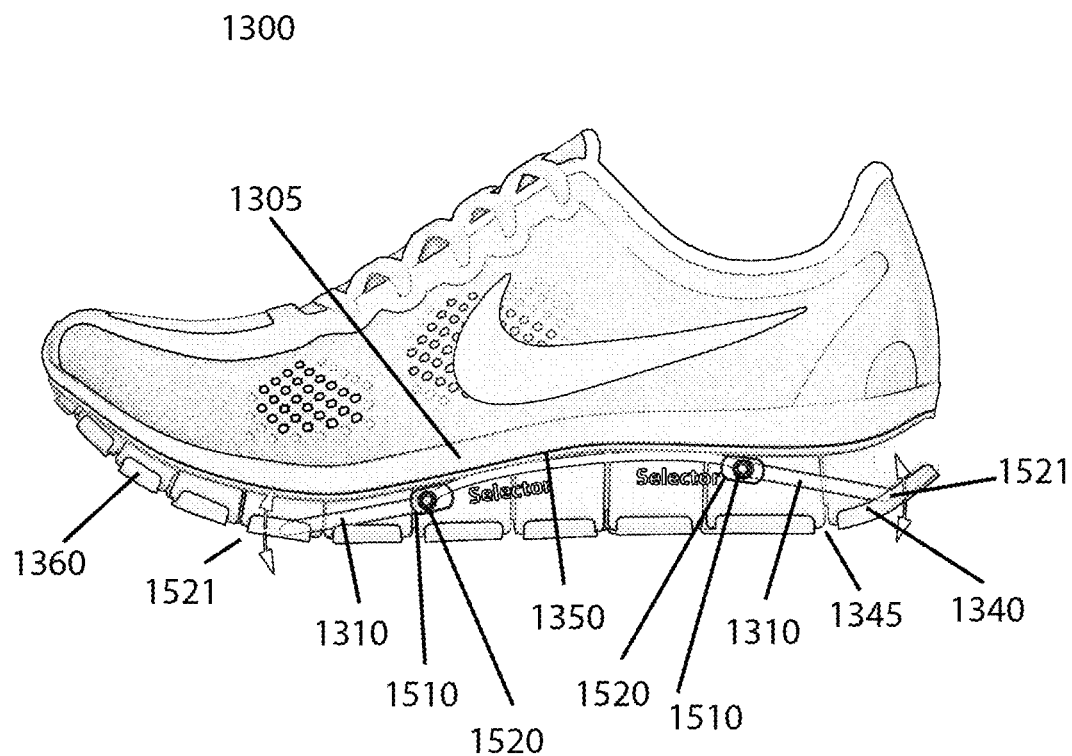
FIG. 13C illustrates a side view of an exemplary configuration of a footwear incorporating a variable resistance (VRB) and suspension system in accordance with the principles of the invention.

FIG. 13C illustrates a side view of an exemplary footwear 1300 in accordance with the principles of the invention.

As illustrated platform 1350, positioned in a center of insole 1305 of footwear 1300, includes pockets 1510 that capture corresponding VRB 1310 at a first end. VRB 1310 extends, at an angle of declination, toward, in this illustrative example, both the front section 1360 and the heel section 1340. Although the VRB suspension support system 1303 shown herein includes four (4) VRBs 1310, it would be appreciated that the number of VRBs 1310 may be increased or decreased without altering the scope of the invention.

Further illustrated is selector or adjustment mechanism 1520 incorporated into pockets 1510. Adjustment mechanism 1520 provides individual control of a corresponding VRB 1310. In this illustrative example, adjustment mechanism 1520 alters the orientation of VRB 1310 with respect to platform section 1350 through the rotation of a gear assembly, as will be discussed. In an alternative embodiment, selector or adjustment mechanism 1520 may be incorporated, referred to as 1521, at one or more of front section 1360 and heel section 1340. Incorporation of selector 1521 into front section 1360 and/or heel section 1340 provides for additional types of selector mechanisms to be utilized.

Figures 14A, 14B, 14C:
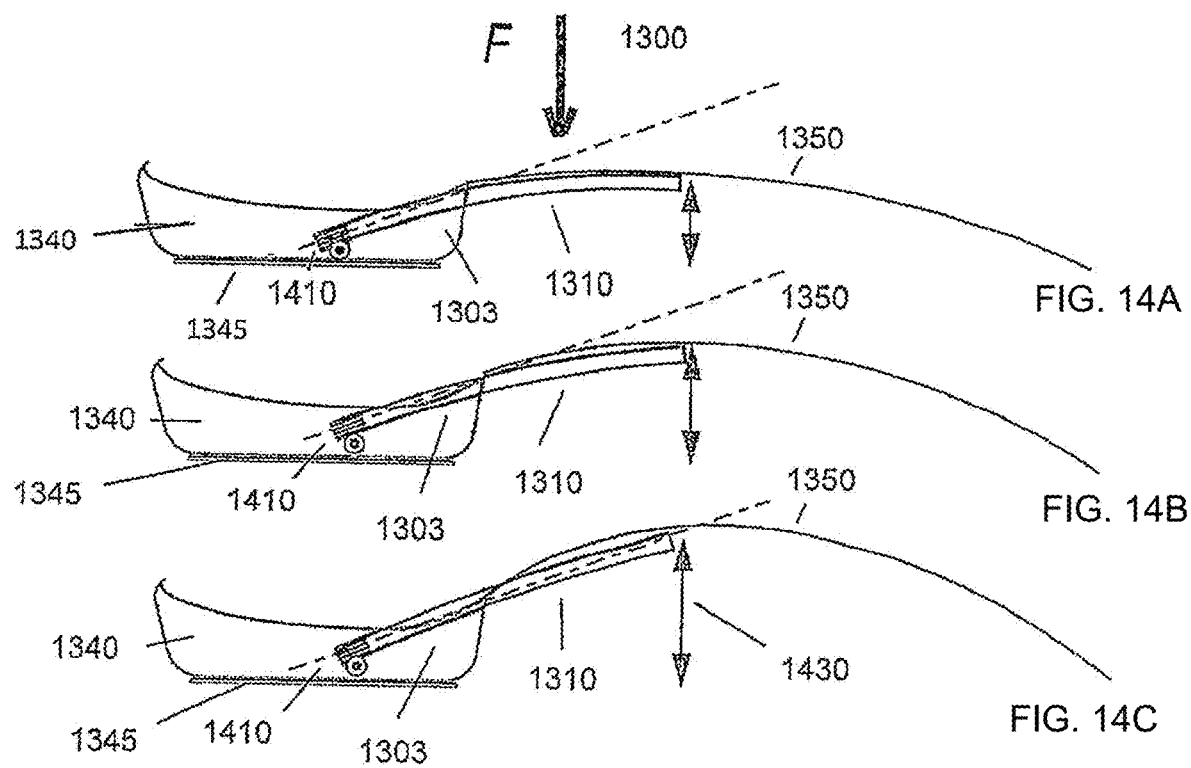
FIG. 14A-FIG. 14C illustrate side views of an exemplary first embodiment of a footwear incorporating a variable resistance (VRB) and suspension system in accordance with the principles of the invention.

FIG. 14A-FIG. 14C illustrate different degrees of support for a platform section 1350 based on an orientation of VRB 1310 with regard to a same level of force (F) applied to the platform section 1350. In these illustrate examples, selector 1521 is shown incorporated into heel section 1340, wherein VRB 1310 extends at an angle of inclination 1410 from surface 1345 to platform section 1350, wherein an end of VRB 1310 is captured in pocket 1510. Although FIG. 14A-FIG. 14C illustrate only a single VRB 1310 it would be appreciated that a second VRB 1310 may extend from front section 1360 to platform 1350, as shown in FIG. 13A, for example.

FIG. 14A illustrates a degree of support for platform section 1350 when VRB 1310 is in a minimum resistive position. In this case, VRB 1310 has a minimum resistance to force F applied to platform section 1350, such that VRB 1310 may have a maximum deviation from an angle of inclination 1410 of VRB 1310 measured with respect to heel surface 1345.

FIG. 14B illustrates a degree of support for platform section 1350 when VRB 1310 is in a position between a minimum resistive position and a maximum resistive position. In this case, VRB 1310 has a mid-level resistance to force F applied to platform section 1350, such that VRB 1310 may have a mid-range deviation from an angle of inclination 1410 of VRB 1310 measured with respect to heel surface 1345.

FIG. 14C illustrates a degree of support for platform section 1350 when VRB 1310 is in a maximum resistive position. In this case, VRB 1310 has a maximum resistance to force F applied to platform section 1350, such that VRB 1310 has a minimum deviation from an angle of inclination 1410 of VRB 1310 measured with respect to heel surface 1345.

As shown in FIG. 14A-FIG. 14C, a height 1430 of platform section 1350 may be altered based on the orientation of VRB 1310 with respect to the platform section 1350 and heel section 1340.

In another aspect of the invention, a height 1430 of platform section 1350 may be determined based the angle of inclination 1410 of VRB 1310 with respect to surface 1345 (or with regard to an angle of declination from attachment plate 1510). In a preferred embodiment, the angle of inclination 1410 of VRB 1310 with respect to a surface 1345 is in the range of 1 degree to 45 degrees. As would be recognized, the angle of inclination of VRB 1310 contributes to the height of platform section 1350 and to the resistance of VRB 1310 to a force applied to platform section 1350.

Figure 15A:
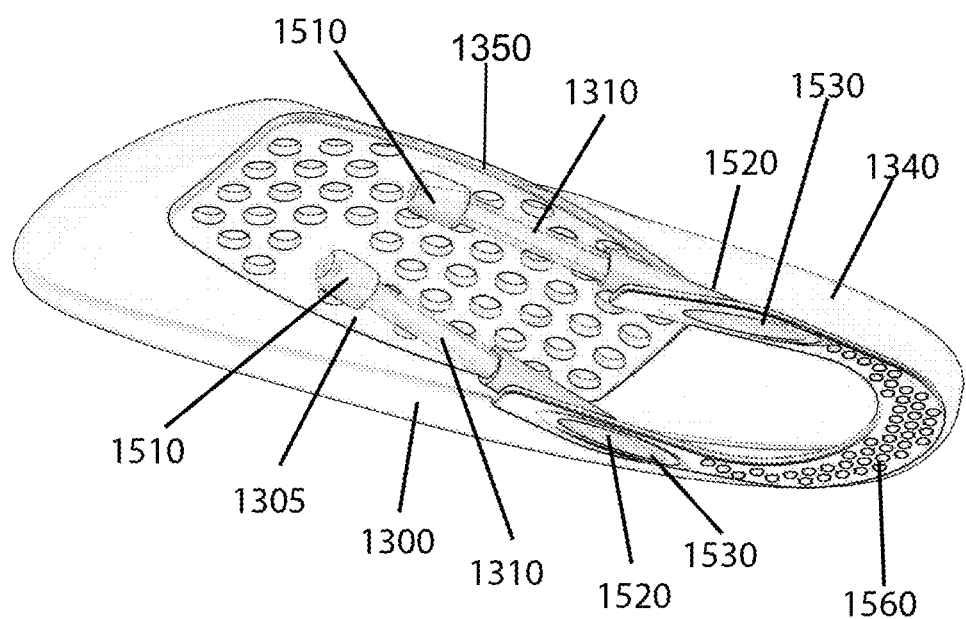
FIG. 15A illustrates a perspective view of an exemplary embodiment of a variable resistance (VRB) and suspension system in accordance with the principles of the invention.

FIG. 15A illustrates a perspective view of an exemplary second embodiment of a VRB footwear variable resistance and suspension system 1303 in accordance with the principles of the invention.

In this illustrated embodiment, two VRBs 1310 are shown supporting platform section 1350 under force plate 1305. In this illustrated embodiment, two VRBs 1310 are positioned on a left side and a right side of platform section 1350. Application of multiple VRBs 1310 provides for symmetric or asymmetric support of a force applied to platform section 1350. Although two VRBs 1310 are shown, it would be appreciated that additional VRBs 1310, extending toward the front of force plate 1305 may be incorporated without altering the scope of the invention.

Also shown are corresponding entry points 1530 that allow access to adjustment mechanisms 1520, which provide individual control of a corresponding VRB 1310. In this illustrative example, adjustment mechanism 1520 alters the orientation of VRB 1310 with respect to platform section 1350 through the rotation of a gear assembly, as will be discussed with regard to FIG. 17A-FIG. 17C, for example.

In the configuration shown, support provided by the VRB 1310 under the platform section 1350 may be adjusted to be firmer on one side than support provided by the VRB 1310 the other side to provide a customized level of support.

Also illustrated is heel plate 1560 that may be incorporated into VRB footwear variable resistance and suspension system 1303. Heel plate 1560 provides additional support for heel 1340 and determines an angle of inclination of VRB 1310.

Figure 15B:
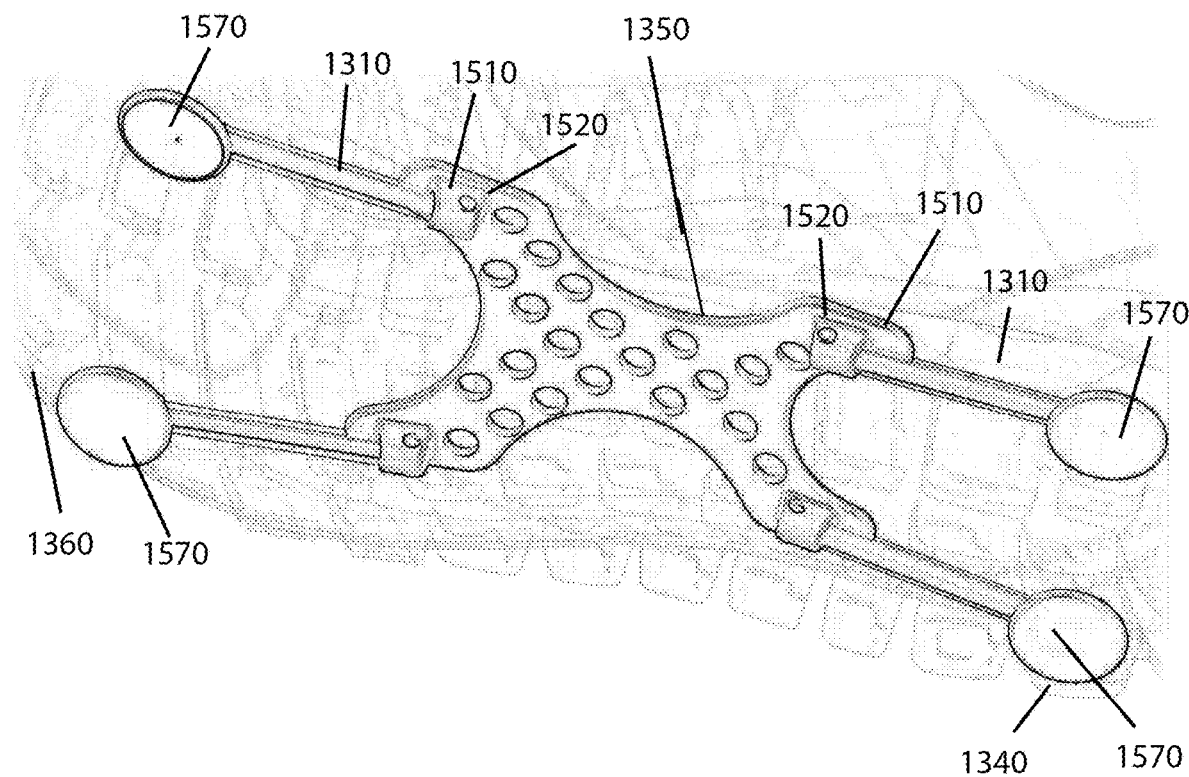
FIG. 15B illustrates a perspective view of a second exemplary embodiment of a variable resistance (VRB) and suspension system in accordance with the principles of the invention.

FIG. 15B illustrates a perspective view of an exemplary embodiment of a VRB footwear variable resistance and suspension system 1303 in accordance with the principles of the invention.

In this illustrated embodiment, VRB 1310 extend from corresponding pockets 1510 attached to platform section 1350. Platform section 1350 is positioned substantially centered in insole 1305 in footwear 1300. Also illustrated are selectors or adjustment mechanisms 1520 incorporated into pockets 1510. As discussed, selectors 1520 provide for rotation of VRB 1310 with respect to attachment plate 410.

Further illustrated are pads 1570 which include pockets (not shown) that capture a free end of a corresponding VRB 1310. Pads 1570 provide for the containment of the VRB footwear variable resistance and suspension system 1303 within footwear 1310, without any exposure (FIG. 15A, element 1530) to an outside environment.

Also shown is platform section 1350 being in a shape of an "X." As would be appreciated platform section 1350 may also be shaped flat, contoured (see FIG. 15A) or conformed to a user, without altering the scope of the invention.

Figure 16A:
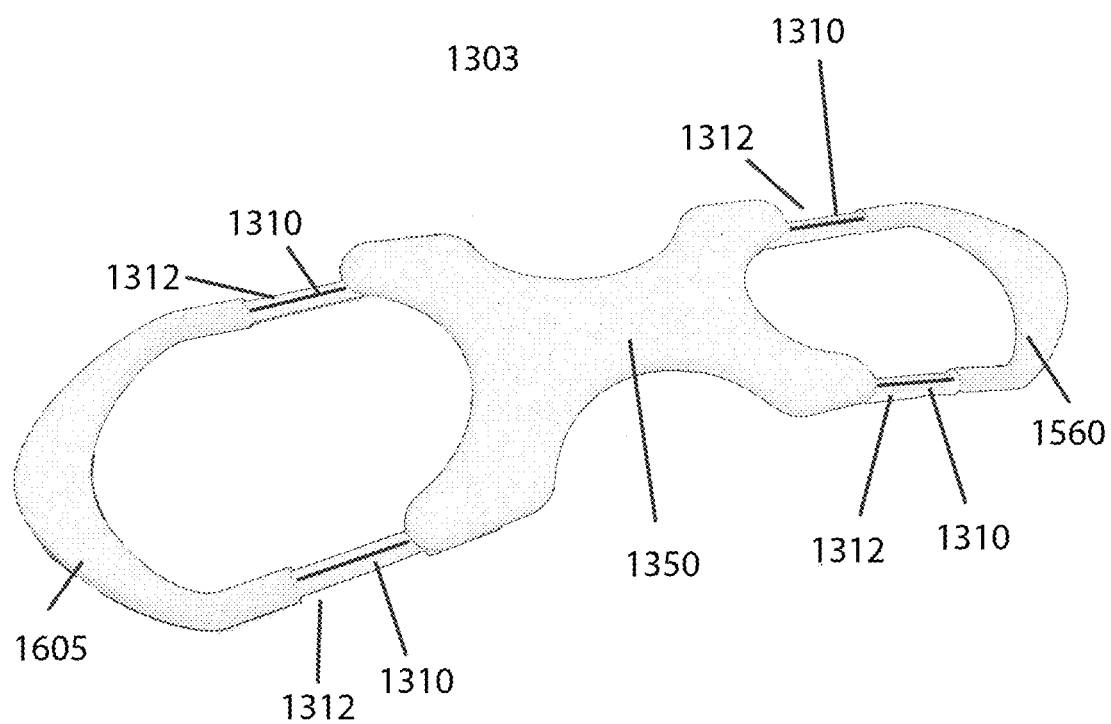
FIG. 16A illustrates a perspective view of an exemplary variable resistance and suspension system in accordance with the principles of the invention.

FIG. 16A illustrates a perspective view of an exemplary embodiment of a VRB suspension support system 1303 in accordance with the principles of the invention.

In this illustrated embodiment VRB 1310 extend, at a known angle of inclination with respect to heel plate 1560 and front plate 1605 towards platform section 1350. As previously discussed, platform section 1350 includes pockets 1510 (not shown) that capture a free end of corresponding VRB 1310. Furthermore, selector 1520 may be incorporated into pockets 1510 or may be incorporated (i.e., selector 1521) into heel plate 1560 and/or front plate 1605 (see FIG. 15A).

In one aspect of the invention, plate of platform section 1350 may be customized to be provide individualized support. As would be appreciated, plate 1350 may be flat, conformed and/or customized without altering the scope of the invention.

As is further shown, VRB 1310 may be contained within a substantially circular housing, sleeve or sheathing 1312. Housing 1312 enables VRB 1310 to rotate substantially uniformly from a minimum resistance position to a maximum resistance (or support) position. In one aspect of the invention, the VRB 1310 may rotate within sheathing 1312, wherein sheathing 1312 is fixed. In another aspect of the invention, VRB 1310 may be attached to sheathing 1312 and as sheathing 1312 rotates, the contained VRB 1310 rotates.

As will be discussed with regard to FIG. 22A-FIG. 22F, VRB 1310 may possess an elongated shape having a major axis greater than a minor axis, which is substantially perpendicular to the major axis.

Figure 16B:
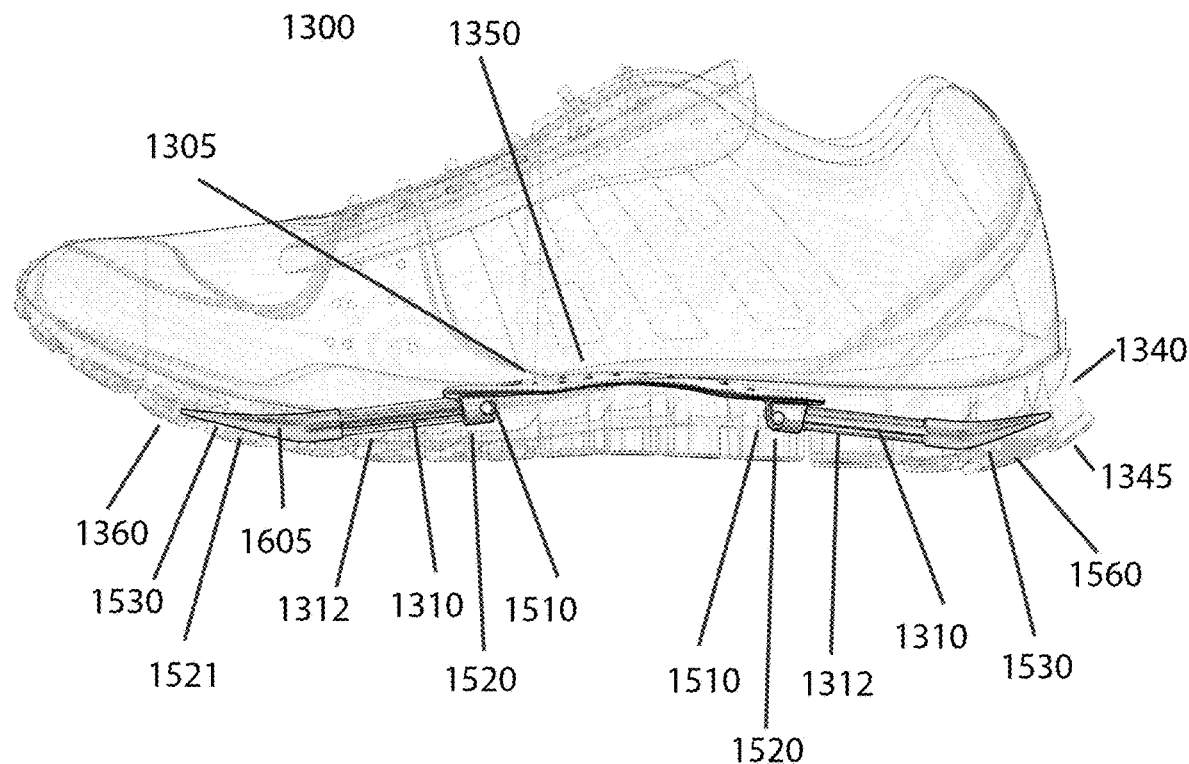
FIG. 16B illustrates a side view of a footwear incorporating a variable resistance and suspension system in accordance with the principles of the invention.

FIG. 16B illustrates a side view of an exemplary embodiment of a footwear 1300 incorporating a VRB suspension support system 1303 as shown in FIG. 16A.

In this exemplary embodiment, VRB suspension support system 1303, positioned substantially center of insole 1305 of footwear 1300 includes platform section 1350, VRBs 1310 extending from pockets 1510, through sleeves 1312, to corresponding heel plate 1560 and front plate 1605, at a known angle of declination (or angle of inclination with regard to heel surface 146 and a surface of front section 1360). As would be appreciated, the angle of inclination may be the same or different for each of the illustrated VRBs 1310.

Also illustrated is an alternate embodiment, wherein front plate 1605 and heel plate 1560 include opening elements 1530 (see FIG. 15A), which allow selector 1521 to be incorporated into front section 1360 and heel section 1340, respectively.

Figure 17A:
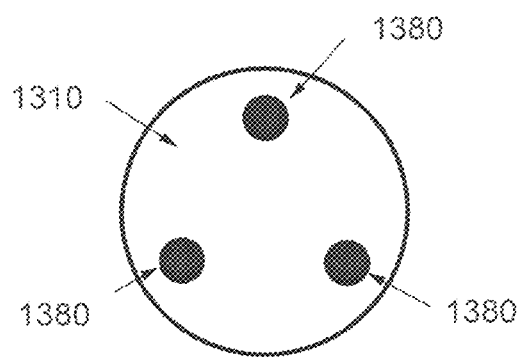
FIG. 17A-FIG. 17C illustrate aspects of a first exemplary embodiment of an adjustment mechanism for controlling rotation of a VRB configuration in accordance with the principles of the invention.
Figure 17B:
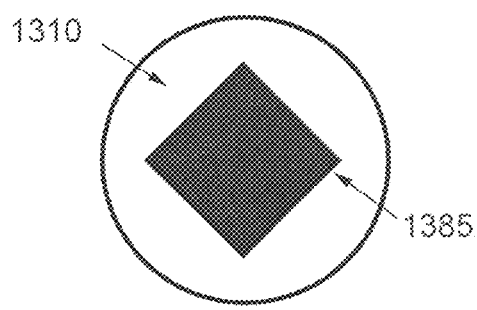
Figure 17C:
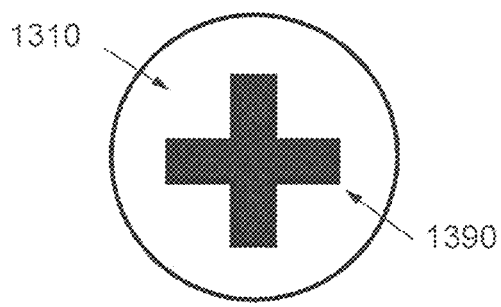

FIG. 17A-FIG. 17C illustrate end views of VRB 1310 including aspects of a first embodiment of an adjustment mechanism for altering the orientation of the VRB 1310.

FIG. 17A illustrates an example of an end of VRB 1310, which is accessible through heel section 1340, for example, that includes three circular cut-outs or indentations 1380 formed in a triangular pattern. Insertion of a tool (e.g., a screw driver) matching the indentation pattern 1380 allows for the rotation of VRB 1310.

Although indentations 1380 are shown in a triangular pattern, it would be recognized that the indentations 1380 may be arranged in any pattern that allows rotation of VRB 1310 to change the orientation of its major axis with respect to heel surface 1345.

FIG. 17B illustrates a second example of an end of VRB 1310 that includes a diamond shaped indentation 1385. In this case Insertion of a tool (e.g., a screw driver) matching the diamond shaped indentation pattern 1385 allows for the rotation of VRB 1310 to change the orientation of its major axis with respect to heel surface 1345.

FIG. 17C illustrates a third example of an end of VRB 1310 that includes a Philips (or cross) pattern. In this case Insertion of a tool (e.g., a screw driver) matching the Philips (or cross) indentation pattern 1390 that allows for the rotation of VRB 1310 to change the orientation of its major axis with respect to heel surface 1345.

The selector or adjustment mechanism shown in FIG. 17A-FIG. 17C may be suitable for use as selector 1521, wherein access to the end of VRB 1310 may be obtained through entry point 1530.

FIG. 18A-FIG. 18F illustrate exemplary aspects of a second exemplary embodiment of an adjustment mechanism in accordance with the principles of the invention.

Figure 18A:
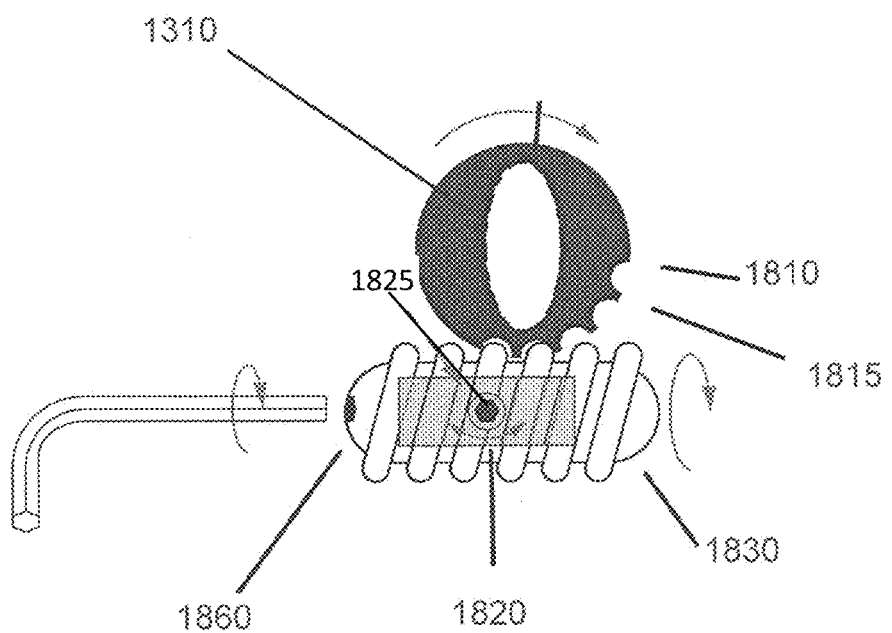
FIG. 18A-FIG. 18F illustrate a second exemplary embodiment of an adjustment mechanism for controlling rotation of a VRB configuration in accordance with the principles of the invention.

FIG. 18A illustrates an exemplary adjustment mechanism represented by a worm gear 1830, which engages a gear 1815 that is incorporated on a substantially circular gear head 1810 to which VRB 1310 is attached. Worm gear 1830 may include an adjustment means (such as an indentation 1860, which may capture an Allen key, Torx key, a Philips tip, for example, as shown in FIG. 17A-FIG. 17C). Insertion of the Allen key into indentation 1860 and rotation of Allen key causes rotation of worm gear 1830. As worm gear 1830 rotates, the rotation of worm gear 1830 is transferred to the gear 1815 of head 1810 causing the rotation of VRB 1310.

FIG. 18A further illustrates a locking plate 1820. Locking plate 1820 retains worm gear 1830 (and consequentially VRB 1310) in a locked position, as will be discussed.

As would be appreciated as VRB 1310 rotates from a minimum resistance position, corresponding to minor axis position, to a maximum resistance position, corresponding to major axis position, support to platform 1350 increases from a minimum to a maximum.

Figures 18B, 18C, 18D:
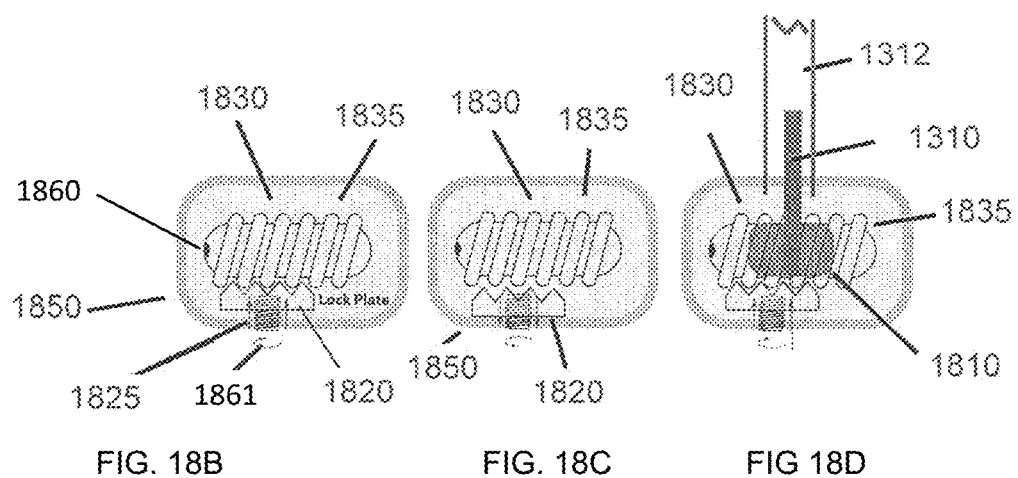

FIG. 18B illustrates a top view of worm gear assembly 1850 including worm gear 1830 and locking plate 1820. Further illustrated is screw (e.g. a set screw) 1825 that alters the position of locking plate 1820 with respect to worm gear 1830.

In one aspect of the invention, as shown in FIG. 18B, assembly 1850 includes a threaded opening 1861, through which passes set screw 1825 to engage locking plate 1820. As set screw 1825 is rotated in a first direction, locking plate 1820 is moved toward worm gear 1830. Locking plate 1820 further includes a toothed surface opposite screw threads 1835 of worm gear 1830. As locking plate 1820 advances towards worm gear 1830, the toothed surface of plate 1820 engages screw threads 1835 of worm gear 1830. In this position, worm gear 1830 is locked in position. Thus, the position of the VRB 1310 is fixed at that position to which VRB 1310 has been rotated by the rotation of worm gear 1830.

In another aspect of the invention shown in FIG. 18C, as screw 1825 is rotated in an opposite direction, the toothed surface of locking plate 1820 is withdrawn from screw threads 1835 and worm gear 1830 is free to rotate. In this manner, locking plate 1820 moves inward or outward along screw 1825 as screw 1825 is rotated. The position of locking plate 1820 may be altered by the insertion of an adjusting means, such as an Allen Key, a Philips screwdriver, etc., in screw hole 1860 to engage screw 1825.

FIG. 18D illustrates a planar view of exemplary embodiment of the worm gear assembly 1850 in accordance with the principles of the invention. In this exemplary embodiment, locking plate 1820 engages screw threads 1835 of worm gear 1830. Also illustrated is gear head 1810 engaging screw threads 1835. Gear head 1810 may be attached to VRB 1310, which enables VRB 1310 to rotate within sheathing or sleeve 1312. Alternatively, gear head 1810 may be attached to sheathing 1312 to allow rotation of VRB 1310.

Figure 18E:
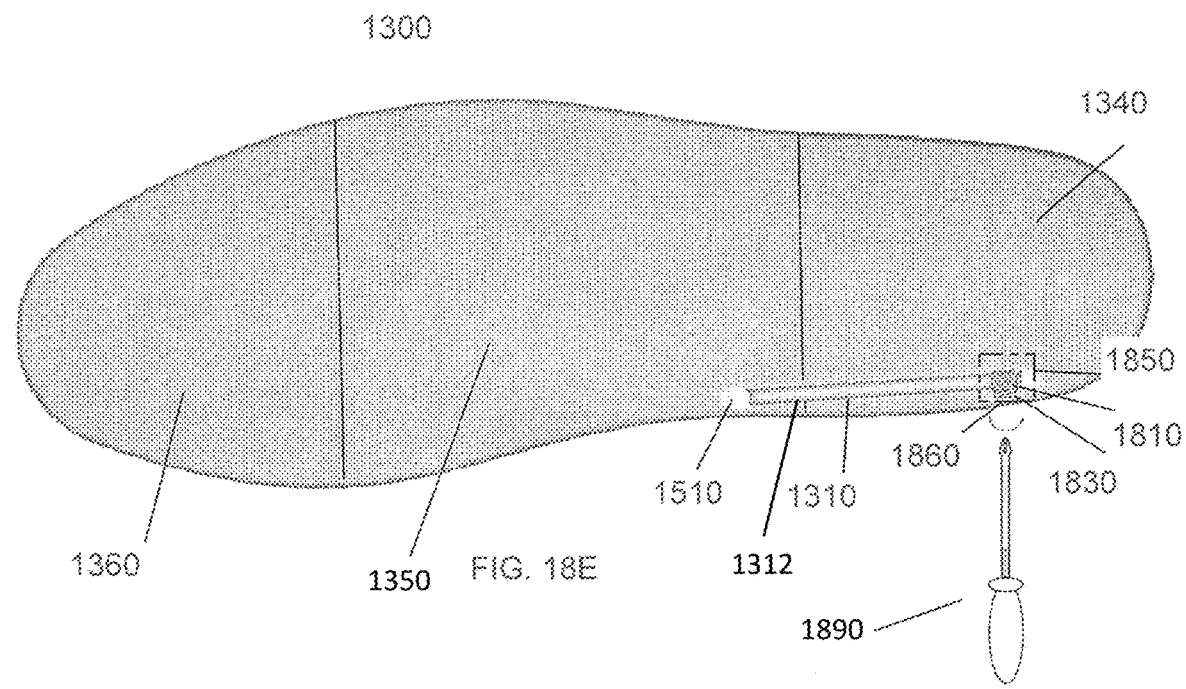

FIG. 18E illustrates a planar view of footwear 1300 including platform section 1350 incorporating the gear assembly 1850, shown in FIG. 18A-FIG. 18D, in heel section 1340. Assembly 1850 includes gear 1830, which engages gear head 1810 attached to VRB 1310. VRB 1310 is captured in pocket 1510, as previously described.

Further illustrated is a conventional Philips tip screw driver 1890 that may be used to rotate gear 1830 by insertion of the Philips tip into indentation 1860, which is shaped in a manner similar to that shown in FIG. 17C.

Although a conventional Philips tip screw driver 1890 is illustrated, it would be appreciated that indentation 1860 may comprise a proprietary shape requiring a corresponding proprietary tip similar to those shown with regard to FIG. 17A-FIG. 17B.

Although a single VRB 1310, it would be appreciated that a plurality of VRBs 1310 may be incorporated in the support system 1302, as shown in FIG. 15B, for example.

Figure 18F:
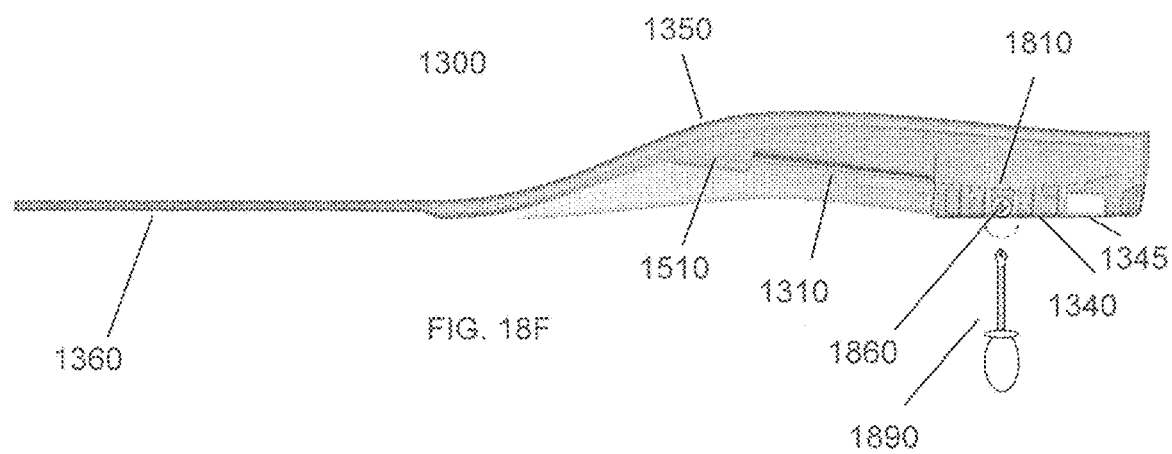

FIG. 18F illustrates a side view of footwear 1300 including platform section 1350 wherein indentation 1860 is shown having a cross shape that engages the tip of Philips screw driver 1890.

As previously discussed, as gear 1830 is rotated, VRB 1310 is rotated through the engagement of gear head 1810 with gear 1830.

The selector or adjustment mechanism shown in FIG. 18A-FIG. 18F may be suitable for use as selector 1520 and selector 1521, wherein access to the adjuster 1860 is through a side of pocket 1510 or a side of heel section 1340.

FIG. 19A-FIG. 19D illustrate aspects of a third exemplary adjustment mechanism for controlling rotation of a VRB utilized in the footwear 1300 shown in FIGS. 13A and 13B, for example.

Figure 19A:
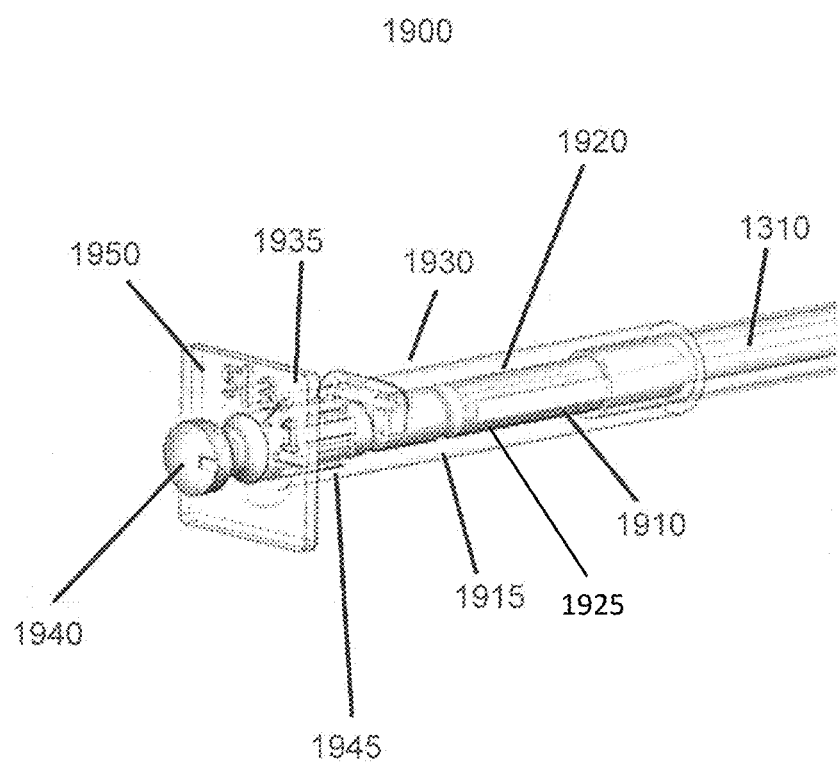
FIG. 19A-FIG. 19D illustrate a third exemplary embodiment of an adjustment mechanism for controlling rotation of a VRB configuration in accordance with the principles of the invention.

FIG. 19A illustrates a perspective view 1900 of a third exemplary configuration of a control or adjustment means in accordance with the principles of the invention.

In this exemplary configuration, referred to herein after as "spline/socket", a manual, geared, mechanism selectively rotates VRB 1310 in controlled increments ranging from 0° to 90° while simultaneously controlling torque.

As shown, the socket/spline 1900 provides an adjustable locking system that secures a VRB 1310 from rotation and therefore mechanically maintains a constant resistance or suspension.

VRB 1310 further includes a fork or tongue 1910 that is insertable into spline 1920. Spline 1920 is a substantially round, solid, rod including tongue or fork 1925. Tongue or fork 1925 engages (and matches) tongue or fork 1910 of VRB 1310.

Also shown is socket 1930 into which spline 1920 is inserted. Socket 1930 contains fork 1925 and tongue 1910 in a manner such that as spline 1920 is rotated, VRB 1310 is similarly rotated.

At a proximal end of socket 1930 is shown grooves 1935 and spline elements 1945 formed between adjacent ones of grooves 1935. In one aspect of the invention, the spacing of spline elements 1945 (grooves 1935), provides for a desired locking rotation. For example, 16 spline elements 1945 provide for 22.5° of incremental VRB 1310 rotation. (360°/16=22.5°).

In accordance with the principles of the invention, VRB 1310 plus spline 1920 form an adjustable assembly, wherein the spline element 1920 maybe pulled out by grasping spline head 1940, rotating the spline element 1920 and re-inserting the spline 1920 into socket 1930, to provide a higher or lower resistance or suspension level. This level of resistance is dependent upon the rotation VRB 1310.

Also illustrated is faceplate 1950. Faceplate 1950 includes an indicia of the degree of rotation of VRB 1310.

As would be appreciated, tongues or forks 1925 and 1910 are sized so that they remain engaged, even when spline 1920 is pulled out, turned and re-inserted into socket 1930.

Figure 19B:
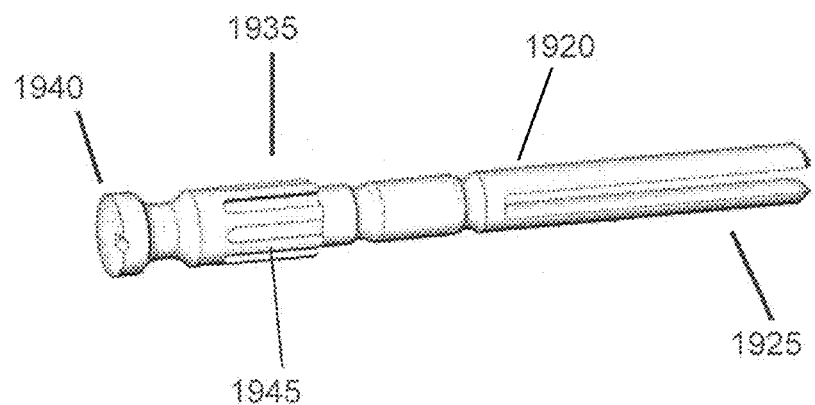

FIG. 19B illustrates a perspective view of spline 1920. In this illustrative embodiment, spline 1920 is a substantially cylindrical rod including at a first end fork 1925 and a spline head 1940 on a second end. Further illustrated are spline elements 1945 positioned about a circumference of spline 1920 between adjacent ones of grooves 1935.

As shown, a length of fork 1925 is sufficiently greater than a length of spline elements 1945 in order to prevent spline 1920 from disengaging VRB 1310 (not shown) when spline 1920 is pulled from socket 1930

Figure 19C:
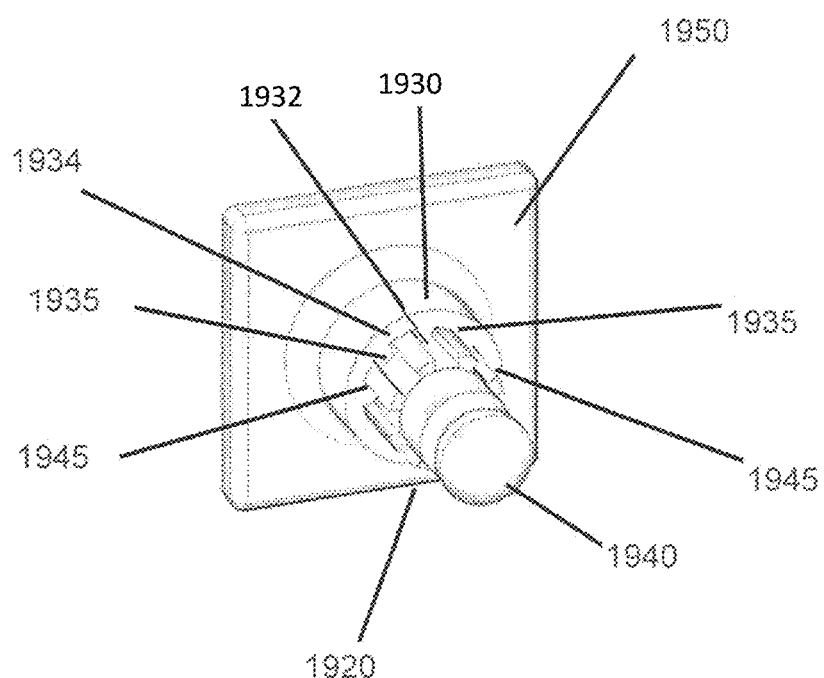

FIG. 19C illustrates a perspective view of a spline element 1945 of spline 1920 engaging grooves 1932 of socket 1930. In this illustrative example, socket 1930 includes a plurality of grooves 1932 and spline elements 1934 between adjacent ones of grooves 1932. Grooves 1932 and spline elements 1934 of socket 1930 match in number and width with spline element 1945 and grooves 1935.

As discussed, spline 1920 may be withdrawn from socket 1930, rotated and reinserted into socket 1930. The rotated and reinserted spline 1920 alters the position of the VRB 1310 (not shown) such that a different level of rigidity of VRB 1310 may be achieved (see FIG. 14A-FIG. 14C). The engagement of spline elements 1945 with grooves 1932 lock and retain VRB 1310 (not shown) in a desired position.

Figure 19D:
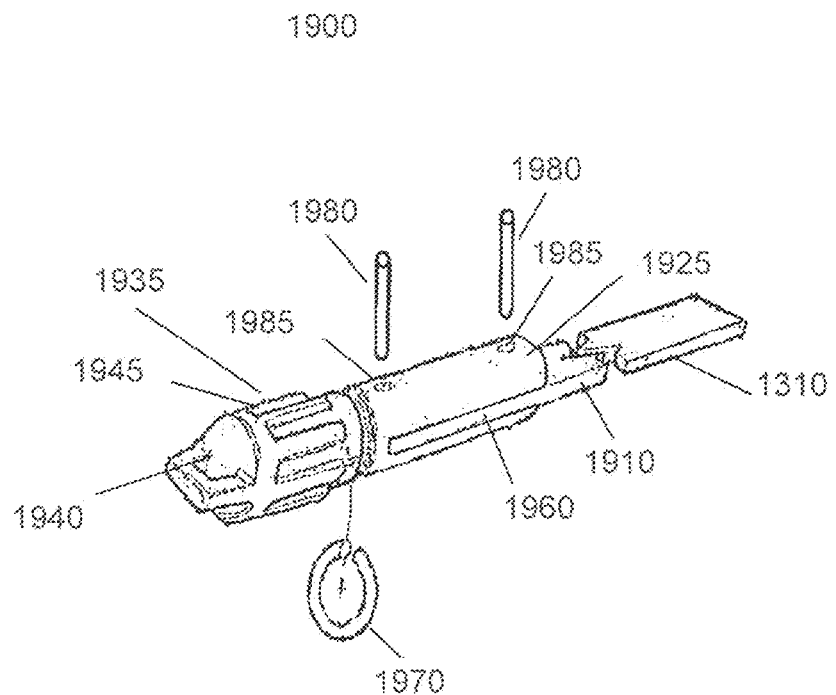

FIG. 19D illustrates a perspective view of a control mechanism 1900 illustrating VRB 1310 engaging fork 1925 in spline 1920 in accordance with the principles of the invention.

In this illustrative embodiment, VRB 1310, which is shown having a rectangular cross-section, includes tongue 1910 that may be inserting into fork 1925 in order to provide a secure connection between tongue 1910 and fork 1925, as previously discussed.

Further illustrated is retaining ring 1970. Retaining ring 1970 represents a spring loaded mechanism that enables spline head 1940 to be withdrawn from socket 1930 by pushing spline head 1940 into socket 1930. The act of pushing spline head 1940 into socket 1930 disengages retaining ring 1970 and the spring loaded mechanism forces spline head 1940 to withdraw from socket 1930. In one aspect of the invention, retaining ring 1970 may be constructed of a spring-able material and shaped to operate as the spring mechanism.

Further illustrated are pins 1980, which when inserted into holes 1985 provide a secure connection between fork 1925 and tongue 1910.

As would be appreciated holes 1985 may be elongated in order to allow spline head 1940 to be withdrawn from socket 1930*a* limited distance. In this case, spline head 1920 may not be totally withdrawn from socket 1930 (not shown) even if spline head 1940 is inadvertently pushed in.

The selector or adjustment mechanism shown in FIG. 19A-FIG. 9C may be suitable as selector 1521, wherein access to the end of VRB 1310 may be obtained through entry point 1530 (see FIG. 15, element 1530).

FIG. 20A(a) illustrates a planar view of an exemplary variable resistance and suspension system 1303 in accordance with the principles of the invention. In this illustrative embodiment, the VRB configuration includes an adjustment mechanism similar to that shown in FIG. 19A, wherein the VRB 1310 may be rotated in discrete intervals. It would, however, be appreciated, that the adjustment mechanism shown in FIG. 17A-FIG. 17C or FIG. 18A-FIG. 18F may similarly be utilized without altering the scope of the invention.

As shown bio-sensor 2030 may be incorporated onto the platform 1350 of footwear 1300. Incorporation of bio-sensor 2030 provides for a prognostic and injury avoidance capability to measure a mechanical deflection of dynamic loads being exerted on a body joint or structure. This is principally achieved through the monitoring of the flexing shape of a VRB (Variable Resistance Beam) or multiple VRBs as loads are dynamically applied, quantified and recorded with the wearer notified of loading conditions that would exceed the joints physical ability sustain normal operation without damage, e.g. repetitive strain. Thus, measurement of dynamic joint loading over time provides a real time health monitoring and predictive system to prevent or treat injury.

A few examples of physical sensors 2030 to measure and quantify joint stress, strain loading cycles, and/or changing suspension support requirements are Thin Films, Wheatstone Bridges (metal foil sensor structures), potentiometers, temperature gauges, pressure gauges, foils, piezo-resistors, semiconductors, nano-particulates, conductive nano-layers, silver nanowire, Graphene, e.g. graphene imbued rubber bands: flexible, low-cost body sensors, such as nanoelectro-mechanical devices, piezoresistive devices, conductive electroplating, diffraction grating, optical fiber, optical grid (Non-Intrusive Stress Measurement System—NSMS), wire, micro tubes, miniature WiFi transmitters, accelerometers, load cells and or other means to detect VRB flexure or movement of any kind.

Physical sensing of the application of a force or strain occurs when one or more VRBs 1310 is deflected or flexed. As the physical shape of the VRB is deformed, an electrical resistance changes. Similarly other measurement quality (ies) or physical parameter(s), e.g. optical, physical location or acceleration, are similar effected.

For example, the Wheatstone bridge illustrates the concept of a difference measurement, which can be extremely accurate. Variations on the Wheatstone bridge can be used to measure capacitance, inductance, impedance and other quantities to calculate total potential movement over time.

Figure 20B:
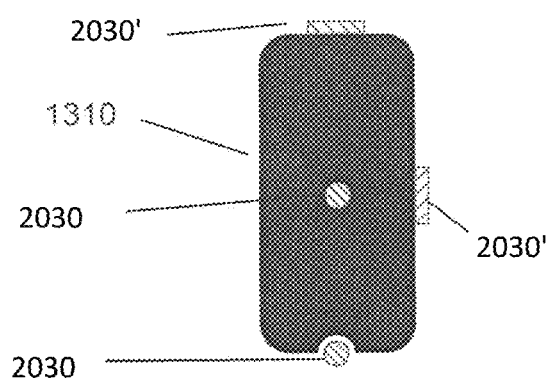
FIG. 20B illustrates exemplary placements of sensing technology in accordance with the principles of the invention.

Although FIG. 20A(a) illustrates the placement of biosensor 2030 on platform, placement and locations of the bio-mechanic sensors 2030 may be bonded onto or along the surface length of VRB 1310, into a side channel and/or internally through an interior diameter hole, bore and or extruded geometry to accept and hold the sensor. (see for example, element 2030'). FIG. 20B illustrates exemplary placement of sensors 2030 on or within VRB 1310.

FIG. 20A(b) illustrates a side view of an exemplary placement of a PCB 2030 on platform 1350.

In another aspect a strain gauge may be incorporated in which advantage is taken of the physical property of electrical conductance and its dependence on the conductor's geometry. For example, when an electrical conductor is stretched within the limits of its elasticity without permanent deformation, the sensor will become narrower and longer. This changes or increases the electrical resistance along the sensors length or end to end. Silver nanowire is an excellent example of an electrical conductor with a 150% stretch limit while measuring conductivity with fidelity.

When measuring electrical resistance of a strain gauge bonded to a VRB 1310, the amount of applied stress may be inferred. As an example, another typical strain gauge arranges a long, thin conductive strip in a zig-zag pattern of parallel lines such that a small amount of stress in the direction of the orientation of the parallel lines results in a multiplicatively larger strain measurement over the effective length of the conductor surfaces in the array of conductive lines—and hence a multiplicatively larger change in resistance—than would be observed with a single straight-line conductive wire.

Other methods of sensing VRB deflection, range from temperature (kinetic heating), piezo (milli-voltage generation), electromagnetic sensing, optical sensing (diffraction grating), to miniature WiFi signalling physical location and or accelerometer chips.

As would be recognized one or more of the described sensors, herein, may be incorporated into the illustrative sensor 2030 (or 2030'). All sensors may directly wired and connected to a physical circuit. Or by means of a wireless signal to an embedded printed circuit board (PCB) with processing algorithm, battery and transmitter information regarding the flex and/or stress detected may be processed (using one or more algorithms) on the PCB and the results forwarded to a remote receiver (i.e., handheld or worn) to alert the wearer to potential injury or current physical condition. Similarly, the measured parameters (i.e., raw data) may be provided to a remote receiver for subsequent processing.

In another aspect of the invention, with the addition of accelerometer microchips, e.g. similar to ones used in smartphones/tablets/watches or such devices, 360° X Y Z axial data is produced and therefore a more informative and prescriptive biomechanic measurements may be captured to warn of impending injury and inform the wearer whether the feet are increasingly pronating or supinating mechanics.

An accelerometer chip interfaced with one or more bio-sensors 2030 may provide further prescriptively diagnose of the body joint condition, i.e. foot, by using quadrant data of the foot to compare and contrast body weight loading (history) and changing weighting dynamics per zone. Specifically, this quadrant data of weight loading combined with an accelerometer chip detecting movement in 360° X Y Z axes may determine whether an injury or foot condition is worsening, progressing to injury, failure, as well as monitor and quantify podiatry foot conditions, e.g. heel posting.

This data would be central to the diagnosis, treatment and physical therapy. Measurement of the parameters associated with the application a force to the variable resistance and suspension system 1303 shown in FIG. 13A, for example, may be customized and tailored to each individual's support requirement and notably reduce atrophy by allowing the wearer degrees of movement.

Figure 21:
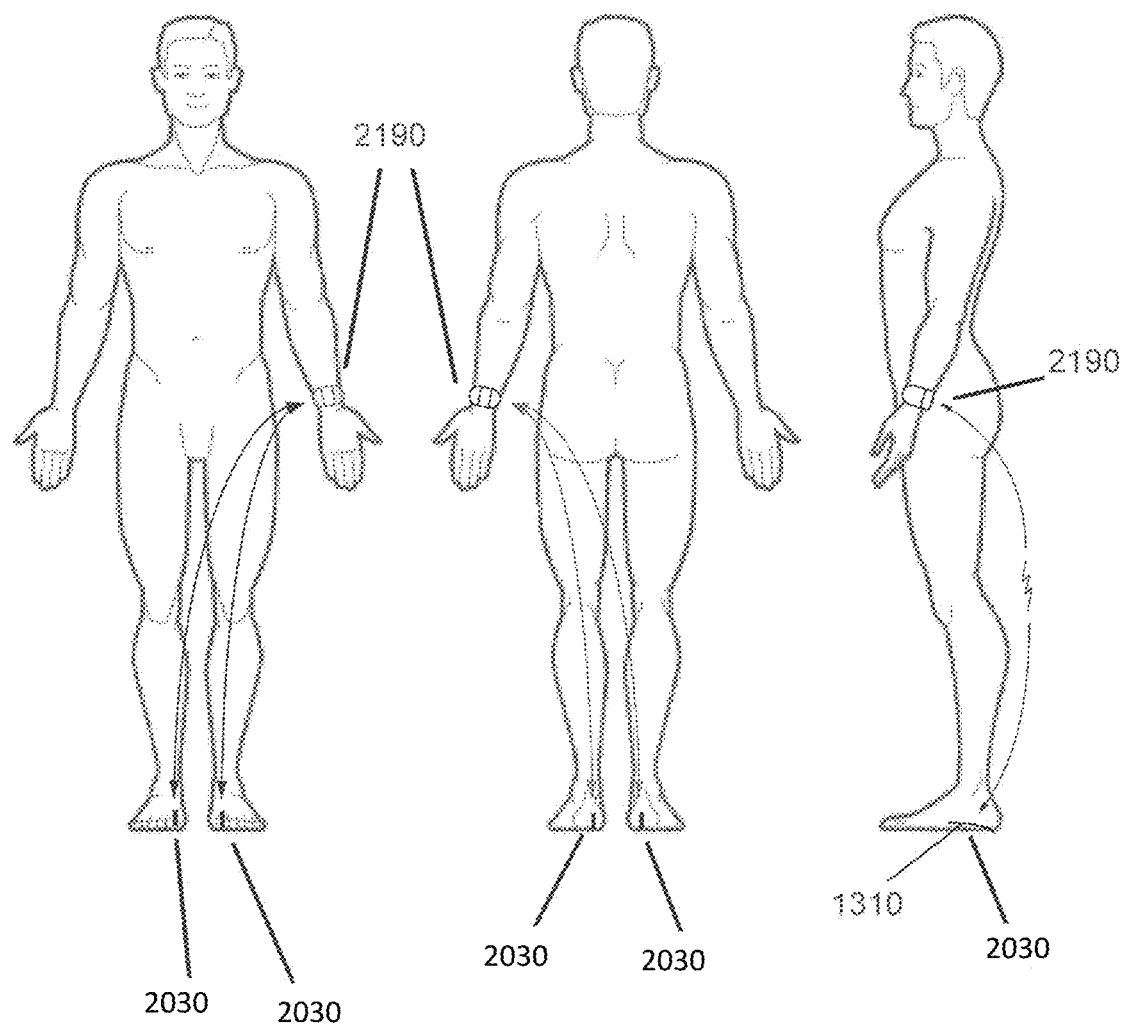

FIG. 21 illustrates an exemplary configuration of a handheld device 2190 communicating with one or more sensors 2030 (2030') incorporated into the variable resistance and suspension system 1303 shown in FIG. 13A, for example.

As would be appreciated communication between sensors 2030 (2030') may be through a short range communication protocol, such as BLUETOOTH, NFC, etc.

In one aspect of the invention, the VRB 1310 mechanical movement may be captured by piezo, dynamo (polyphase AC/DC electric motor), hydraulic or other mechanism to capture and store mechanical energy from the VRB flexing or footwear shell cyclical compression during walking. This system may be used as a battery recharging system using a device capable of capturing mechanical movement and converting the mechanical movement into electrical energy. For example, piezo-material or PvF2 (PolyVinylidene Fluoride 2) may be incorporated into the VRB assembly to create a battery recharging system and/or a heel cushion to absorb bodyweight impacts via shock absorbing diaphragm. Additionally, part of the energy generated would be used to transmit the bio-sensor data to a wearable device (2190, FIG. 21) to inform the wearer in real time of the condition of their body joint condition, i.e. left or right foot.

In another aspect of the invention, the recharging system may also be connected to and provide energy to drive a worm gear servo to change the VRB resistance setting to prescriptively support the body joint condition in response to the bio-sensor data. This closed looped system provides a prescriptively corrective, rehabilitative, prophylactic or preventative support system for a body joint or extremity, e.g. foot, by increasing and/or decreasing the support imparted. The closed data loop system consists of a flexing VRB 1310 to biomechanically support a body structure or joint bonded to a Biosensor whose data stream is connected to an 'onboard PCB' (printed circuit board). The biosensor data signal is received, transmitted and stored onto the PCB to produce an algorithm output. The closed data loop system is sustained by a mechanism to continually charge a battery and/or supply electricity to charge the system. An advanced version of this charging system could be employed to automatically instruct a worm gear servo to change the VRB support levels (lower or higher) per biosensor diagnostic algorithm data stream.

In another aspect of the invention additional means of creating self-adjusting footwear shell geometry may incorporate the use of programmable smart materials, such as carbon fiber, nitinol wire mesh, smart, self-morphing filaments, e.g. wood, or composite materials designed to become highly dynamic in form and function, specifically when a electric charge is applied or other shaping factors.

FIG. 22A-FIG. 22F illustrate cross-sectional views of exemplary embodiments of a VRB in accordance with the principles of the invention. The VRBs, presented as resilient rods, beams or shafts, may be composed of solid, semi-solid or hollow construction in accordance with embodiment the principles of the invention. The VRB technology comprises a major and minor axis, which produces variable resistances when orientated in a direction of x, y, z plane or combination of planes in 360 degrees of rotation, bending movement.

FIG. 22A represents a Type II I-Beam configuration 2210 that includes one of: a static outside and internal diameter geometry or combination, thereof. The Type II I-Beam cross section geometry produces proportional adjustable resistance according to a rotated orientation creating a relationship between an orientation and a resistance.

FIG. 22B represents a Type III Dual I-Beam configuration 2215 that includes inner and outer I-Beam tubes with inner and/or outer geometry or combination thereof to create variable I-beam resistance.

FIG. 22C represents a Type IV Conical beam configuration 2220 that includes hollow, additive or subtractive wall geometry. Conical Beam cross section geometry produces proportional adjustable resistance according to a rotated orientation.

FIG. 22D represents a Type V Ellipsoidal beam configuration 2225 that may be a solid, a semi-solid or a hollow beam with or without outside and/or internal diameter geometry or a combination, thereof along its major axis, thus, generating additional I-beam mechanics and/or subtractive, e.g., conical hollow, geometry along its minor axis. Ellipsoidal beam with a major axis that is wider than the minor axis with or without internal or external geometry along the major axis.

FIG. 22E represents a Type VI Internal 'I-beam' configuration 2230 that includes one or more spines within a hollow cylindrical or conical shaft.

FIG. 22F represents a Type VII Rectangular beam configuration 2235 that includes two sides wider than the remaining two sides.

VRB 1310, which may be solid, semi-hollow or hollow, with or without geometrically created I-beam effect (i.e., asymmetric geometry, spines) on the outside or interior diameter generates resistance depending on the axis of orientation and/or a fulcrum position has been described herein. A VRB 1310, with incorporated I-beam geometry on the outside diameter, may allow for the dynamic adjustment of resistance of the device. An advantage of a device including VRBs described herein may be compact, lightweight and offer the ability to more easily and quickly change a desired level of resistance than is typically found in units using weights, rubber bands, bows or springs. By simple reposition or rotation of a VRB incorporated into the device, a desired selectable range of resistance level may be achieved. The VRBs 1310 disclosed, herein, can provide resistance, depending on the orientation of the beam, to a bending direction. In addition, an exemplary device incorporating the VRB technology may vary the resistance provided to the user during rehabilitative exercise, without interrupting the exercise cycle. Additional beam resistance is achieved depending upon the relative orientation of the beam within a 180° degree hemisphere of movement relative to the user.

Hence, according to the principles of the invention, a progressive dynamic resistance may be achieved with a variation of the orientation of the beam or shaft shown herein.

In one aspect of the invention, rods with symmetrical cross sections vary their bending resistance by shortening and lengthening the arc length, from fulcrum to anchor point by hand position per indicia.

In another aspect of the invention, rods with asymmetrical cross sections may increase or decrease their bending resistance by rotation of the elongated orientation with respect to a bending force, while maintaining the same hand adjusted position or fulcrum length.

In one aspect of the invention, the VRBs 1310 may be composed of thermoplastic polymers, especially high tenacity polymers, include the polyamide resins such as nylon; polyolefin, such as polyethylene, polypropylene, as well as their copolymers such as ethylene-propylene; polyesters, such as polyethylene terephthalate and the like; vinyl chloride polymers and the like, and polycarbonate resins, and other engineering thermoplastics such as ABS class or any composites using these resins or polymers. The thermoset resins include acrylic polymers, resole resins, epoxy polymers and the like.

Polymeric or composite materials may contain reinforcements that enhance the stiffness or flexure of the flexure resistance spine. Some reinforcements include fibers, such as fiberglass, metal, polymeric fibers, graphite fibers, carbon fibers, boron fibers and Nano-composite additives, e.g., carbon nano-tubes, et al., to fill the molecular gaps, therefore strengthening the material.

Additional materials that the resistance rods or VRBs 1310 may also be composed of include high tensile aircraft aluminum and high carbon spring steel and/or high tensile strength to weight materials.

Figure 12:
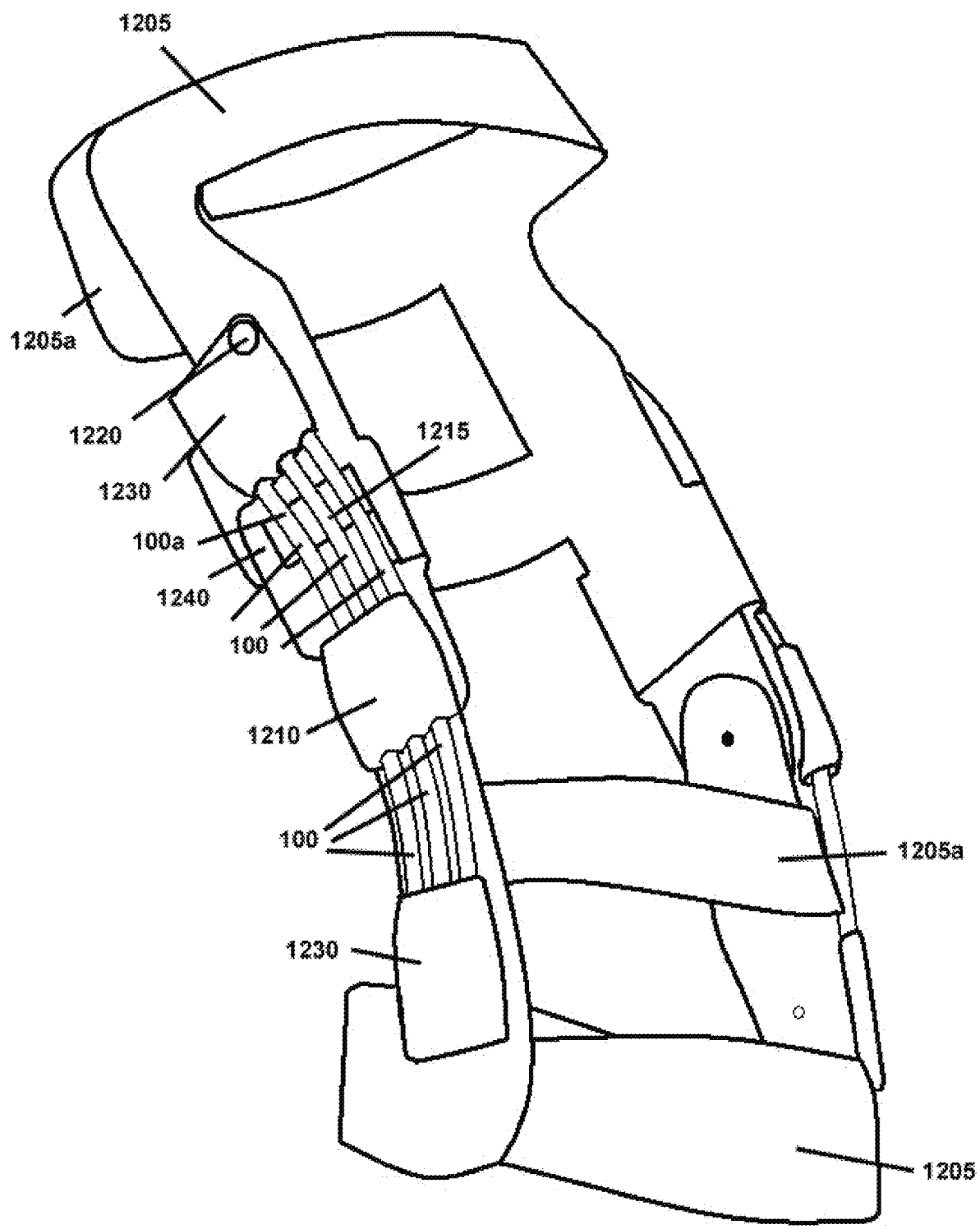
FIG. 12 illustrates an exemplary medical device configured in accordance with the principles of the invention. The resistance beams are employed into mobility assistance and rehabilitative braces that provide dynamic support and suspension via a fulcrum mechanism.

FIG. 12 illustrates an exemplary medical brace in accordance with the principles of the invention. In this illustrative example, at least one VRB 100 is incorporated into a VRB assembly 1215 into an anchor 1230, an adjuster 1220, and a fulcrum 1210. The bracing system in FIG. 12 is comprised of a thigh leg strap collar 1205 attached to a frame with a fulcrum 1210 connected to a hinge 1225 with an upper arm 1240 with a bushing piston acting as a second cartilage.

In this illustrative embodiment, VRBs 100 are adjusted to create a variable flex. Element 1205 illustrates leg strap or collar (thigh). Element 1205a illustrates leg strap or collar (calf). Element 1210 illustrates fulcrum for VRB to maintain controlled bending. Element 1215 illustrates a VRB assembly (one or more VRB's) that acts as a leaf-spring/unloader; i.e., a first suspension point. Element 1220 illustrates VRB assembly adjuster to customize flexibility or resistance. The assembly adjuster 1220 may be a worm gear as previously described. Element 1225 illustrates a hinge that mimics the bio-mechanical movement or range of an anatomical joint (e.g. knee). Element 1230 illustrates VRB assembly anchor with spring/bushings: i.e., a secondary suspension point. Element 1240 illustrates a telescoping upper hinge arm with a bushing piston, a second cartilage: i.e., a third dampening or cushioning point. VRB assemblies 100a or 1215 provides a dynamic supportive structure designed to act as an artificial or second knee to support a damaged or injured one.

An additional benefit of incorporating the VRB 100 technology into medical devices is that the resistance rods, under compression, create a proportioned constant vertical lift to unload 1215 and dynamically support the joint (e.g., a knee) during post op, rehabilitation, arthritis or during extreme sports. Hence, the VRB 100 technology described herein provides a truly functional and adjustable brace that provides for Shock Absorbing 1215, 1230, 1240, Active Suspension 1215, Adjustable Comfort DST Unloader Knee Brace.

As previously described, resistance ranges are generated by rotating the beams over a fulcrum positioned adjacent to a body joint.

Dynamic support is also beneficial for the recuperative period following operation, rehabilitation, arthritis or during extreme sports. Additionally, resistance beam assemblies may also contribute to shock absorption via a bushing and piston arm mechanically connected to the beam assembly. Furthermore, beam assemblies positioned on each side of a joint act as lateral stabilizers.

FIG. 23A illustrates a further example of the incorporation of a VRB 100 into a running or athletic shoe 2300 (similar to 1300, FIG. 13A) in accordance with the principles of the invention.

In this illustrated embodiment, the shoewear 2300 includes an upper section and a lower or sole section 2310 that are formed together. Further illustrated are a plurality of footwear module or adjustable platforms 2305, wherein one platform is positioned, within the sole section 2310, a forward portion, before the foot arch section 2307, and one is positioned aft of the foot arch section 2307. The footwear module or adjustable platform 2305 is composed of a VRB 100 (referred to hereinafter as 2320 (and is similar to form and characteristics as that described with regard to VRB 100 (and 1310) in FIG. 1A-FIG. 1G. VRB 2320 further includes a threaded end section 2360. Further illustrated is an anchor plate 2330, which includes a containment pocket or socket 2370. The containment pocket 2370 includes an internal thread. The containment pocket may be a separate section attached to the anchor plate or may be conformally formed as a part of the anchor plate 2330. The threaded end section 2360 of VRB 2320 engages the internally treaded socket or pocket 2370 such that VRB 2320 is rotatable within the threaded socket 2370.

Although a plurality of footwear module or adjustable platforms 2305 are shown, it would be appreciated that the shoewear 2300 may comprise a single footwear module or adjustable platform 2305 without altering the scope of the invention.

As is further illustrated the footwear module or adjustable platforms 2305 may be oriented within the sole 2310 such that an angle of orientation of the footwear module or adjustable platform 2305, with respect to a surface upon which the shoewear 2300 rests may be set at any desired angle. As shown, the rear footwear module or adjustable platform 2305 is essentially parallel to the surface while the forward footwear module or adjustable platform 2305 is set at an angle of approximately 20 degrees.

However, it would be understood that the angle of orientation of a footwear module or adjustable platform 2305 may be set as shown in FIG. 14A-FIG. 14C, wherein a height of the VRB 2320 above the surface may be altered, FIG. 23B illustrates a bottom view of the shoewear 2300 further illustrating the arrangement of the VRBs 2320 and anchor plate 2330 in accordance with the principles of the invention.

In this illustrated embodiment, each footwear module or adjustable platform 2305 is composed of two VRBs 2300 extending from a corresponding anchor section 2330. The anchor sections 2330 reside on either side of the shoe arch section 2307 and the VRBs extend form the corresponding anchor section toward the forward and back of the shoewear respectively.

Further illustrated are access nodes 2350 within sole 2310. Access nodes 2350 allow a user to gain access to a corresponding VRB 2320 so as to rotate the VRB 2320 and, thus, adjust the level of flex (or resistance) the VRB 2320 possesses in response to a downward force applied by the shoewear (see FIG. 14A-FIG. 14C, for example).

Although the access nodes 2350 are shown under the shoe 2310, it would be recognized that the access nodes 2350 may be positioned in a manner as shown in FIG. 13C, wherein the access nodes 1530 are used to obtain access to the VRBs are arranged along a side of the sole 2310.

Also illustrated is an angle of orientation ($\alpha$) of the VRBs 2310, within a same anchor plate 2330, with respect to each other. The angle of orientation is selected to provide a stable platform for the shoewear to limit an amount of twisting experienced by the shoewear with an unequal application of force of the footwear module or adjustable platform 2305. In one aspect of the invention, the angle of orientation may be selected as zero (0) degrees i.e., substantially parallel VRB orientation). However, the angle of orientation may be selected, based in part on the length of the VRB 2320 and the width of the shoewear to substantially 45 degrees.

FIG. 24A illustrate an exemplary VRB 2320 including a threaded or helix end section 2360. As previously discussed the VRB 2320 is equivalent to the VRB 100 and possesses the shapes and characteristics previously discussed.

FIG. 24B illustrates an exemplary anchor section 2330 including the threaded pockets 2370. The thread pitch of pocket 2370 is comparable to the thread pitch of thread section 2360. As would be recognized the degree of rotation of the VRB 2320 is determined based on the thread pitch. As discussed, the rotation of VRB 2320 alters the resistance of the VRB to a downward force applied by a user, for example, wearing the shoewear.

Returning to FIG. 23A, further illustrated is a wrap element 2425 that may be optionally placed around the thread section 2360. The wrap element 2425 may be of a material that compensates for any irregularities between the thread section 2360 and the internal thread within threaded pocket 2370. The wrap element 2425 may further allow for a frictional force to retain VRB 2320 in a set position.

FIG. 24C illustrates a completed footwear module or adjustable platform 2305, in accordance with the principles of the invention, wherein the threaded section 2360 of a corresponding VRB 2320 is inserted in a corresponding threaded pocket 2370 of angle 2330. In this case the angle of orientation (a) between the VRBs 2320 is set by the angle of threaded pockets 2370 of the anchor 2330.

FIG. 25A illustrates a bottom view of the completed footwear module or adjustable platform 2305, similar to that shown in FIG. 24C. Further illustrated is an adjustment tool 2510 which is insertable into an open end 2520 (not shown) of threaded pocket 2370. The adjustment tool 2510 enable a user to alter the orientation of the VRB 2320, as has been discussed previously.

FIG. 25B illustrates a side view of the footwear module or adjustable platform 2305 shown in FIG. 25A, wherein the adjustment tool 2510 engages an end of VRB 2320 through open end 2520. Although adjustment tool 2510 is shown in a key shape it would be appreciated that the adjustment tool 2510 may be of any shape, such as a screwdriver.

Although not shown, in FIG. 25B, the end of VRB 2320 includes an indentation that allows the adjustment tool 2510 to engage the VRB 2320 in order to turn the VRB 2320. For example, the indentation within the end of the VRB 2320 may be similar to those disclosed with regard to FIG. 17A-FIG. 17C. In addition other indentation shapes have been contemplated and are considered to be within the scope of the invention.

FIG. 25C illustrates an end view of VRB 2320, which in this illustrated example is shown with an elliptical shape (see Type V bar, FIG. 1E). Further illustrated is thread 2540 circumventing VRB 2320. In this illustrated example, the treaded section 2370 is a substantially circular configuration (similar to that shown in FIG. 18A). It would be understood that threaded pocket 2370 would be of a similar configuration. Further shown is indentation 2530, which is substantially semi-elliptical or elongated semi-circular shape. The orientation of the semi-elliptical shape in this case provides an indication of the orientation of the VRB 2320. That is, as the semi-elliptical indent is aligned with the major axis of the VRB 2320, the orientation of the indent provides an indication of the orientation of the major axis and, hence, the degree of resistance the VRB 2320 possesses with respect to a force applied to the shoewear. That is FIG. 25C illustrates a maximum resistance, while FIG. 25D illustrates a minimum resistance.

Although FIG. 25C and FIG. 25D illustrate a substantially circular threaded section 2360, it would be recognized that the treaded section 2360 may be incorporated directly on the VRB 2320 and the threaded section 2360 would engage the threaded pocket as previously discussed. In this case, any non-conformity between the shape of the threaded section 2360 and the pocket 2370 may be compensated for with wrapping 2510 as previously discussed.

FIG. 26A illustrates a second embodiment of a footwear module or adjustable platform 2605 in accordance with the principles of the invention. In this illustrated embodiment, the footwear module or adjustable platform 2605 is comprised of a plurality of footwear module or adjustable platforms 2305 and a flexible membrane 2610 joining the plurality of footwear module or adjustable platforms 2305. The orientation of the footwear module or adjustable platforms 2305 is similar to that shown in FIG. 23A, and as previously discussed may be selected based on the previously discussed criteria.

FIG. 26B illustrates a bottom view of a footwear module or adjustable platform 2605 shown in FIG. 26A. As shown a flexible membrane 2610, positioned under the arch section 2307 of the shoewear 2300, joins the two footwear module or adjustable platforms 2305. The flexible membrane 2610 provides further resistance force as a force is applied to the footwear and provides a restoring force to return the footwear to its original configuration when the applied force is removed.

FIG. 26C illustrates a side view of the footwear module or adjustable platform 2605 shown in FIG. 26A and FIG. 268.

In this illustrated example, the footwear module or adjustable platforms 2305 and the flexible material 2610 are essentially flat and, thus, may be positioned within a shoewear to achieve a desired configuration. That is, the angle of orientation of the forward and the rear footwear module or adjustable platform 2305 may be set as desired and as previously discussed.

FIG. 27A illustrates a second exemplary embodiment of the VRB 2720 in accordance with the principles of the invention.

In this illustrated embodiment, which is similar to that shown in FIG. 23A, includes a threaded section 2760 positioned substantially at a mid-point of VRB 2360, rather than at an end. In this configuration, VRB 2720 operates in a manner as previously discussed, wherein the orientation of the VRB 2720 determines an amount of resistive force the VRB 2720 possess with regard to a force applied to the VRB 2720.

FIG. 27B illustrates a complete footwear module or adjustable platform 2705 in accordance with the second exemplary embodiment of the VRB 2720 shown in FIG. 27A. As shown, the angle of orientation of the VRBs 2720 is substantially zero as the VRBs 2720 are illustrated in a parallel configuration. However, it would be understood that the angle of orientation (a) may be set as previously discussed.

As further illustrated, the VRB 2720 extends through the threaded pocket and exits the open end 2520. Further illustrated is the VRBs 2720 may be adjusted to have different lengths with respect to the anchor 2330. The different lengths of the VRBs extending from the anchors 2330 in conjunction with the orientation of the orientation of VRB 2720 may determine an amount of resistive force the VRB 2720 possess with regard to a force applied to the VRB 2720.

FIG. 28A and FIG. 28B illustrate a configuration for manufacturing a shoewear incorporating a footwear module or adjustable platform 2305 in accordance with the principles of the invention.

FIG. 28A illustrates a footwear module or adjustable platform 2305 including a plurality of entry holes 2820 in VRB 2320 and 2825 in anchor module 2330. FIG. 28B illustrates the insertion of alignment stakes 2810 into corresponding entry holes 2820 and 2825.

FIGS. 29A and 29B illustrate a side view of a molding jig for retaining the footwear module or adjustable platform 2305 in a desired position during a molding process. In this illustrated aspect, the alignment stakes 2810 are contained within molding base 2910. The footwear module or adjustable platform 2305 is positioned on the alignment stakes 2810 through the entry holes 2820 and 2825 as previously discussed. In this illustrated case, alignment stakes 2810 are sized to position the footwear module or adjustable platform 2305 at a desired angle. In this illustrated example, the stakes 2810 are selected such that the footwear module or adjustable platform 2305 is oriented at an 8 degree angle with regard to the molding base. However, as has been previously discussed, the orientation of the footwear module or adjustable platform 2305 may be selected to satisfy desired conditions. Although, the footwear module 2305 is shown at an eight (8) degree angle, it would be appreciated that the footwear module 2305 may be set at any desired angle. Preferably, the footwear module 2305 is set within a range of zero (0) to twenty-five (25) degrees.

FIG. 29B illustrates an additional setup configuration of footwear module positioning at a predetermined incline held in place by two sets of positioning pins 2810. One set on pins is secured to the bottom 2910 of the mold while the other set of pins 2810 is secured to a top 2920 of the mold.

When the mold closes wherein the top 2920 engages the bottom 2910, the footwear module platform 2305 is held in position, as a polymer is injected into the sealed mold to form the shoe sole. The bottom and top pin sets the footwear module securely in position in situ of the mold.

Two sets of pins are required when higher injection pressures are used to ensure module position in situ during molding. Two pin sets provide a compressive sandwich, i.e., top down/bottom up, that creates a strongest clamping force to hold the module in position, when the mold is closed and sealed for polymer injection.

FIG. 30 and FIG. 31 illustrated molding configurations for the shoewear shown in FIG. 23A and FIG. 26A, wherein the alignment stakes are positioned within the base 2910, the footwear module or adjustable platforms 2305 are positioned on alignment stakes 2810 to achieve a desired orientation of a corresponding footwear module or adjustable platform 2305 and the sole is then molded containing the footwear module or adjustable platforms 2305 set at the desired orientation.

Note in this case, the rear footwear module or adjustable platform 2305 is set at an angle different than that shown in FIG. 23A and FIG. 26A, to illustrate that the orientation of the footwear module or adjustable platform 2305 may be changed as desired.

FIG. 32A illustrates a top view of an exemplary VRB 3220 in accordance with the principles of the invention.

In this illustrated embodiment, the shape of the VRB 3220 is a conical shape along its longitudinal axis. As illustrated, the VRB 3220 includes a screw thread 3260, similar to the screw thread previously discussed.

Further illustrated is the width of the VRB 3220 "X2," at the base of the screw thread is greater than the width of the VRB 3220 "X1" at the other end of the VRB.

FIG. 32B illustrates a side view of the exemplary VRB 3220 shown in FIG. 32A. In this illustrated case, the height, "Y2," of the VRB 3220, at the base of the screw thread is greater than the width of the VRB 3220 "Y1" as the other end of the VRB.

In this illustrated example, VRB 3220 is representative of an elongated VRB having a major axis (X) greater than a minor axis *Y).

Further illustrated is a bulbous section 3230 at the free end of the VRB 3220, The bulbous (e.g., spherical) section 3230 further includes an indentation 3260. Indentations 3260 may similar to the indentations 1860 (FIG. 18A) or 2530 (FIG. 25C) operate to rotate the VRB 3220 using adjustment tool, similar to tool 2510.

In the case the indentations 3260 are incorporated into the VRB 3220 then the corresponding access entry point (e.g., 2350, FIG. 23B; 1530, FIG. 13C) is positioned such as access to indentation 3260 is achieved.

Although not shown it would be recognized that the section 3220 and/or the indentation 3260 may be incorporated into the VRB 1320 (FIG. 13A) or VRB 2330 (FIG. 24A) or VRB 2730 (FIG. 27A), without altering the scope of the invention.

Although not shown, it would be further recognized that a sensor unit, similar to that shown in FIG. 20, may be incorporated into the footwear configuration shown in FIG. 23A and FIG. 26A without altering the scope of the invention.

FIG. 33A and FIG. 34A illustrate prospective views of exemplary conically-shaped VRB 2330 having a major axis greater than a minor axis in along a longitudinal axis of said VRB 2330. FIG. 33A illustrate an exemplary trapezoidal shaped VRB 2330 and FIG. 34A illustrates an exemplary elliptically shaped VRB 2330. In each these exemplary shaped VRBs 2330, a screw thread 2360 is shown at the end of the VRB. Further illustrated are cross-section views, labelled A-A, B-B E-E, to show the cross-sectional shape of the VRB from a first end to the screw thread end.

FIG. 33B and FIG. 34B illustrate multi-cross-sectional views of the longitudinally conically shaped cross-section trapezoidal shaped VRB 2330 shown in FIG. 33A and the longitudinally conically shaped cross-section elliptically shaped VRB 2330 shown in FIG. 34A. In each of these exemplary conically shaped VRBs 2330, as with the VRBs previously described, herein, the X axis width is always wider than the Y axis height.

In one aspect of the invention, the VRB's 100 may be composed of thermoplastic polymers, especially high tenacity polymers, include the polyamide resins such as nylon; polyolefin, such as polyethylene, polypropylene, as well as their copolymers such as ethylene-propylene; polyesters, such as polyethylene terephthalate and the like; vinyl chloride polymers and the like, and polycarbonate resins, and other engineering thermoplastics such as ABS class or any composites using these resins or polymers. The thermoset resins include acrylic polymers, resole resins, epoxy polymers, and the like.

Polymeric materials may contain reinforcements that enhance the stiffness or flexure of the flexure resistance spine. Some reinforcements include fibers, such as fiberglass, metal, polymeric fibers, graphite fibers, carbon fibers, boron fibers and Nano-composite additives, e.g. carbon nano-tubes, et al, to fill the molecular gaps, therefore strengthening the material.

Additional materials that the resistance rods or VRB's may also be composed of include high tensile aircraft aluminum and high carbon spring steel and/or high tensile strength to weight materials.

Although the different applications of the VRBs shown herein refer to VRB 100 (type I), it would be recognized that each of the applications may incorporate one or more of the other type of VRBs (i.e., type II through type VII) without altering the scope of the invention.

The resilient VRB's shown in herein may be used with or in conjunction with sports equipment and exercise apparatus to create meaningful exercise and or other useful mechanisms. For example, devices suitable for exercise equipment, sports equipment, home improvement and medical mobility may be created to selectable control bending strength or resistance ranges to impart performance benefits. VRB's may be secured at one or more fixed points with the appropriate device may be used to provide appropriate variable resistance. In addition, the VRBs may be handheld at various points along the beam length to affect fulcrum resistance and or rotated to different incremental orientations to affect resistance with discrete geometric cross sections. In one aspect of the invention, VRB's may be perpendicularly mounted to a variety of mechanical apparatus to affect resistance and may additionally be handheld in the air to expand the exercise envelop.

The VRB's described herein may be manufactured based on a method selected from a group consisting of: rapid prototyping, stereolithography, molding, casting, extrusion and other known in the art.

A VRB's, which may be solid, semi-hollow or hollow, with or without geometrically created I-beam effect (i.e., spines) on the outside or interior diameter generates resistance depending on the axis of orientation and/or a fulcrum position has been described herein. VRBs 100, with incorporated I-beam geometry on the outside diameter, can allow for the dynamic adjustment of resistance of the device. An advantage of a device including a VRBs described herein may be—compact, lightweight and offer the ability to more easily and quickly change a desired level of resistance than is typically found in units using weights, rubber bands, bows or springs. By simple hand reposition, as shown in FIG. 3, or rotation of beam of the incorporated into the device a desired resistance level may be achieved. The VRBs 100 disclosed, herein, can provide resistance, depending on the orientation of the beam, to the user. In addition, the device can vary the resistance provided to the user during an exercise, without interrupting the exercise cycle. Additional beam resistance is achieved depending upon the relative orientation of the beam within a 180° degree hemisphere of movement relative to the user. Hence, according to the principles of the invention, a progressive dynamic resistance may be achieved with a variation of the orientation of the beam or shaft shown herein.

The principle of Progressive Dynamic Resistance (PDR) are:

controlled and rotatable (variable) resistance beam with ergonomic work zones:

Multiple, sequential, mechanical resistances are achieved for the purpose of rehabilitation and exercising of endoskeletal musculature.

Increased/decreased incremental mechanical resistance and exercise adjustability is achieved through beam rotation and or fulcrum hand position relative to the beam or arc length/distance along the resistance beam to impart desired work load.

PDR's 180° or 360° degree range of dynamic arcing motion provides an exercise resistance program for every male or female body type with variability in muscle size and strength to provide gain after unilateral resistance training of progressive resistance exercise (PRE).

PDR's incremental mechanical resistance capability (i.e., resistance adjustability through rotation and or fulcrum hand position) facilitates and customizes the user's strength curve and exercise requirements from simply moving hand/leg position to tailor the optimum resistance to maximize the workout of the targeted muscle group.

PDR resistance beam technology does not have mechanical flat spots or dead spots and provides continuous resistance curve to maximize workout loading on the targeted muscle groups, thus creating a more effective work out.

PDR's bend/arc/range of motion means that as the resistance beam is bent farther away from a plane of minimum resistance, the sustained mechanical resistance incrementally increases, creating a progressively more intense and effective work out/work load on the target muscle group.

Continuous Progressive Dynamic Resistance loading from the bending of VRBs 100 is a highly effective biomechanical exercise.

In other aspects of the invention, different types of sport equipment and apparatus may incorporate the VRBs 100 technology described herein. Examples in which VRB 100 technology may be applied are:

FlexGym & FlexTrax products represent an apparatus or structure to hold a plurality of rod holders into which VRB 100 resilient adjustable or non-adjustable solid or tubular rods and other exercise apparatus are inserted to allow users to perform a variety of exercises. FIGS. 3, 4 and 5 illustrate an exemplary system in accordance with the principles of the invention.

FlexBoard product represents an apparatus or structure wherein a transportable structural panel resting on the ground with rod holders into which VRB's 100 are inserted perpendicularly to allow users to perform a variety of exercises. FIG. 6 illustrates an exemplary FlexBoard system in accordance with the principles of the invention.

FlexGym represents an apparatus or structure wherein the VRB 100 technology of the present invention may be incorporated into a plurality of structural tracks with rod holders providing multiple positions into which the VRB 100 resilient adjustable or non-adjustable solid or tubular rods and other exercise apparatus are inserted to allow users to perform a variety of exercises in an I-formed structure, with a cantilevered bench that folds down or may be a free form bench. In addition, the floor tracks, which also comprise the lower structure of the unit, can be optionally retracted to the vertical tracks when not in use.

In one aspect of the invention a means to track and record exercise cycles per set of the user may be incorporated. For example, biometric data of the user may be recorded on a smart card, a smart phone, a computer, etc. so exercise cycles can be recorded. In addition, biometric data of the user may be conveyed by magnet, reflector, RFID, WiFi or other means to measure or quantify exercise cycle.

In another aspect of the invention, the exercise apparatus may include sensors (e.g., WiFi) to sense proximity of the user as the user approaches the exercise apparatus. The sensors may also be in communication with a user's smart phone transmitter or other technical means and the exercise apparatus respond may be setup to correspond to a user's particular exercise regime.

Another embodiment of the exercise apparatus sensors would recognize a user via sensor or WiFi or iPhone transmitter that would initiate servo-mechanisms to proactively set a customized workout cycle. This would mean that the track holder along the track, be it vertical or horizontal, and would be matched to the user's ergonomic body size and requirements.

In another aspect of the invention a video display or monitor may be incorporated to enable a user to receive instructions regarding a particular exercise or to watch one or more programs of interest during the exercise session.

Returning to FIG. 3, FIG. 3 represents a method for incorporating the VRB 100 technology into an apparatus for exercise with one or more anchor point which is represented by the product FlexToner. More specifically, the present invention related to a resilient adjustable or non-adjustable solid or tubular rod exercise apparatus handheld at one or more places and flexed.

Other VRB 100 exercise apparatus applications are, but not limited to, upper and or lower body exercise machines: (e.g. treadmills, stair climbers, elliptical trainers, stationary bikes, mobility, medical, rehabilitative systems that create and control selectable bending strength or resistance ranges with fixed rotation to impart PDR) isolating the upper and or lower body for exercise.

The present invention may be incorporated into devices that provide for low impact/low resistance exercises (e.g., Rehabilitative and Geriatric exercisers) to strengthen and rehabilitate post surgical, bed-ridden, sport injury and or geriatric benefit. Typically, these devices may employ VRBs 100 that are matched to the strength of the user. For example, VRB 100 may be adjusted to provide rigid support during an initial healing phase of a sports injury and then adjusted to provide lesser amount of support to compensate for progress during the healing of the sport injury.

Although, the present invention is described with regard to a plurality of different equipment, it would be recognized that the described equipment are merely examples to which the VRB technology described herein may be applied. The examples provided herein are merely illustrative of the application of the claimed technology and the examples are not intended to limit the subject matter claimed.

In other aspects of the invention, other types of sports equipment and apparatus may incorporate the VRB 100 technology described herein. Examples in which VRB 100 technology may be applied are, but not limited to:

Golf Clubs

Golf clubs may be formed of graphite, wood, titanium, glass fiber or various types of composites or metal alloys.

Each varies to some degree with respect to stiffness and flexibility. However, golfers generally carry onto the golf course only a predetermined number of golf clubs.

Varying the stiffness or flexibility of the golf club is not possible, unless the golfer brings another set of clubs of a different construction. Even in that case, however, the selection is still somewhat limited.

Nevertheless, it is impractical to carry a huge number of golf clubs onto the course, each club having a slight nuance of difference in flexibility and stiffness than another. Golf players prefer taking onto the course a set of clubs that are suited to the player's specific swing type, strength and ability.

Returning to FIG. 8, which illustrates an exemplary embodiment of an internal VRB 100 in a hollow shaft (e.g., a golf shaft). As previously discussed, the VRB 100 is centrally raised or lowered within the golf shaft, the fulcrum or kick point is raised or lowered, thereby changing the shaft flex. The 360 degree symmetrical geometry provides a solution for an adjustable golf club and would be fully compliant with the existing USGA rules of golf and assorted international golf associations.

Running Shoes, Training Shoes, Basketball Shoes

The transmission of the shoe wearer's strength (power) from their legs into the ground is directly affected by the sole stiffness of the shoe. Runners may gain more leverage and, thus more speed, by using a stiffer sole. Basketball players may also affect the height of their jumps through the leverage transmitted by the sole of their shoes. If the sole is too stiff, however, the toe-heel flex of the foot is hindered.

It is advantageous that the shoe wearer have the ability to tailor the sole stiffness to his/her individual weight, strength, height, running style, and ground conditions. Preferably, the shoe wearer may tailor the stiffness of the shoe sole to affect the degree of power and leverage that is to be transmitted from the wearer into the ground.

In this example, VRB 100 are insertable, insert molded or structurally connected to the shoe sole in lateral and/or longitudinal positions within the sole and are all rotatable to a fixed and mechanically locked position to effect custom flexural resistance range. Additionally, zones of resistance are customizable, e.g. the right pad of the foot can be made more rigid than the left pad side through the beam's rotated orientation. Thus, the degree of flexibility may be customized to accommodate a user's desired preferences.

Incorporation of the VRB 100 technology into running shoes, as shown in FIG. 11, and FIG. 23-34B provides a dynamic adjustable in-sole suspension system that can absorb the weight of the wearer and release it per each step.

Hockey Sticks

Hockey includes, but is not limited to, ice hockey, street hockey, roller hockey, field hockey and floor hockey.

Hockey players may require that the flexure of the hockey stick be changed to better assist in the wrist shot or slap shot needed at that particular junction of a game or which the player was better at making. Players may not usually leave the field to switch to a different piece of equipment during play.

Younger players may require more flex in the hockey stick due to lack of strength and such flex may mean the difference between the younger player being able to lift the puck or not when making a shot since a stiffer flex in the stick may not allow the player to achieve such lift.

In addition, as the younger players ages and increases in strength, the player may desire a stiffer hockey stick, which in accordance with convention means the hockey player would need to purchase additional hockey stick shafts with the desired stiffness and flexibility characteristics. Indeed, to cover a full range of nuances of differing stiffness and flexibility characteristics, hockey players would have available many different types of hockey sticks.

Even so, the hockey player may merely want to make a slight adjustment to the stiffness or flexibility of a given hockey stick to improve the nuances of the play. Thus, the incorporation of the VRB technology into hockey sticks (shaft and/or blade) provides for variations in the stiffness and flexibility that may be adjusted as the user progresses in their ability.

Incorporation of the VRB technology into hockey sticks is similar to that shown in FIG. 7.

In other aspects of the invention, different type of Do-it-Yourself (DIY) and Home Improvement products and devices may incorporate the VRB technology described herein. Examples in which VRB technology may be applied are:

Lawn Equipment:

Adjustable lawn rake with VRB 100 tines:

The VRB 100 technology described by the present invention may be incorporated into a lawn rake. In this case, an adjustable rake with a rotatable VRB 100 down the shaft of the rake may be created. The VRB 100 facilitates the adjustment of the lawn rake, with the ability to adjust stiffness of the shaft relative to the load (e.g., light grass clippings, heavy grass clipping, wet grass clippings).

Incorporation of the VRB 100 technology into lawn rake (or other similar handled devices) is similar to that shown in FIG. 10A and FIG. 10B.

In another embodiment, the VRB 100 technology described by the present invention may be incorporated into tines of a lawn rake creating an adjustable rake. Thus, the VRB 100 facilitates the adjustment of a lawn/utility rake by providing the ability to create variable shaft resistance for light or heavy duty gravel raking due to its rotated orientation. The VRB 100 adjustment setting may simultaneously rotate the rake's tines from 0° to 90°, thus affecting a stiffer tine orientation. The tines may be elliptical or oval in shape in an embodiment of an elliptical VRB 100. When the tines are in a 0° orientation, they are the most flexible and suitable for raking leaves or light duty yard work. When the tines are in a 90° orientation, they are the most rigid and suitable for raking heavy duty gravel. The flexural change of tines can be further impacted by means of adjusting where the center point of a fulcrum of the flex of tines is located.

FIG. 10A illustrates an exemplary lawn rake incorporating the VRB 100 technology disclosed herein. FIG. 10A and FIG. 10B illustrates a rake assembly 1000 including a handle 1010 and a tine assembly 1015 including a plurality of VRB 100 tines that are simultaneously adjusted through rotation. FIG. 10B illustrates a bottom view of rake 1000 showing the orientation of the tines 100 at a maximum resistance level (90 degree orientation).

Thus, the incorporation of the VRB 100 technology in the tines creates a flexible lawn rake to alter the flex characteristics of the rake.

Although, the present invention is described with regard to a plurality of different lawn equipment, it would be recognized that the lawn equipment described herein are merely examples to which the VRB technology described herein may be applied. The examples provided herein are merely illustrative of the application of the claimed technology and the examples are not intended to limit the subject matter claimed.

In other aspects of the invention, different type of medical products and devices may incorporate the VRB technology described herein. Additional examples in which VRB technology may be applied are: Mobility assistance and Rehabilitative Braces that provide dynamic support and suspension for joints and orthotic braces: Foot, ankle, knee, hip, back, shoulder, elbow, wrist, neck (i.e., Prophylactic, Functional Support, Post-operative, Unloader and or Extreme Sports, acting as a second compression driven reactive joint, et al.).

In this aspect of the invention, the VRBs 100 may be used to create a medical brace or orthotic device that by provides a dynamic support and suspension system with variable and adjustable resistance settings to achieve an adjustable performance range so as to customize the brace or device during the recuperation stage of the wearer, acting as external supporting spring ligament or adjustable box spring structure and/or further supported by a conformal brace framework. For example the conformal brace framework may be a mechanical joint and/or a flexible webbing, e.g., Ballistic nylon/Neoprene et al.

In one aspect of the invention, the medical brace or orthotic device may be used to:

1. control, guide, limit and/or immobilize an extremity, joint or body segment for a particular reason;
2. To restrict movement in a given direction;
3. To assist movement generally;
4. To reduce weight bearing forces for a particular purpose;
5. To aid rehabilitation from fractures after the removal of a cast; and
6. To otherwise correct the shape and/or function of the body, to provide easier movement capability or reduce pain.

Although, the present invention is described with regard to knee brace, FIG. 12, it would be recognized that the described braces are merely examples to which the VRB technology described herein may be applied. The examples provided herein are merely illustrative of the application of the claimed technology and the examples are not intended to limit the subject matter claimed. For example, the VRB technology described herein may be applied to braces that are used for the back, arm, elbow, neck, and legs, without altering the scope of the invention.

In another aspect of the VRB technology described herein, braces or devices may be constructed wherein the VRB beams are equipped with attached sensors [e.g. Electrogoniometer] to provide continuous bio-mechanic feedback or other biomechanical sensor means of medical or injury diagnostic. For example, compression, extension, articulation, Range and/or twisting measurements may be made and provided to a network (e.g., a WIFI, wireless) to monitor the movement of the user.

In another aspect of the invention, the braces including the VRB technology described herein may include sensors, such as impedance wire sensors, accelerometer, stressors, etc., to measure flexural strength, cycle counts per day to measure Joint performance, injury, damage assessment, etc., so that an appropriate monitoring of the healing of the effected joint may be monitored. Such monitoring is valuable in the field of professional sports medicine, for example.

In still another embodiment of the VRB technology described herein provides further benefits in the medical profession, wherein a VRB may be made from a BIO-Degradable Polymer that may be incorporated into an Internal Fixation brace. In this case, the internal VRB may be rotatable using outside setting pins connected to an internal worm gear at the head of the internal VRB. The main benefit of bio-degradable VRB fixation beams is that they require no post-operative surgery to remove. The biopolymers may be of a non-toxic material capable of maintaining strong mechanical integrity until engineered to degrade, wherein controlled rates of degradation (typically a function of crystallinity) are predetermined. An additional benefit is to not create an immune response and or the products of degradation must also be non-toxic.

Controlled degradation rates may be affected by a percentage of polymer crystallinity, molecular weight, hydrophobicity and location within the body.

Examples of promising biodegradable polymers to be made into VRBs through extrusion and or injection molding are, but not limited to, 3-hydroxypropionic acid, the suture polymer Polyglycolide and or Poly(lactic acid) or polylactide (PLA). A thermoplastic aliphatic polyester that degrades into lactic acid, a natural waste product of the body.

Although the different applications of the VRB shown herein refer to VRB 100 (type I), it would be recognized that each of the applications may incorporate one or more of the other type of VRBs (i.e., type II through type VII) without altering the scope of the invention.

The specification is to be regarded in an illustrative manner, rather than with a restrictive view, and all such modifications are intended to be included within the scope of the invention.

Benefits, advantages, and solutions to problems have been described above with regard to specific embodiments. The benefits, advantages, and solutions to problems, and any element(s) that may cause any benefits, advantages, or solutions to occur or become more pronounced, are not to be construed as a critical, required, or an essential feature or element of any or all of the claims.

While there has been shown, described, and pointed out fundamental novel features of the present invention as applied to preferred embodiments thereof, it will be understood that various omissions and substitutions and changes in the apparatus described, in the form and details of the devices disclosed, and in their operation, may be made by those skilled in the art without departing from the spirit of the present invention. It is expressly intended that all combinations of those elements that perform substantially the same function in substantially the same way to achieve the same results are within the scope of the invention. Substitutions of elements from one described embodiment to another are also fully intended and contemplated. For example, any numerical values presented herein are considered only exemplary and are presented to provide examples of the subject matter claimed as the invention. Hence, the invention, as recited in the appended claims, is not limited by the numerical examples provided herein.

What is claimed is:

1. A footwear comprising:
    an upper section; and
    a sole section attached to the upper section:
    at least one footwear module embedded in the sole section, the at least one footwear module comprising:
        an anchor plate comprising:
            at least one containment pocket containing an internal thread; and
        at least one variable resistance beam having a major axis and a minor axis, said major axis being greater than said minor axis, wherein said at least one variable resistance beam extends towards a corresponding containment pocket in the anchor plate, wherein a threaded section of the variable resistance beam engages the internal thread of the containment pocket; and a selection mechanism incorporated into an end of a corresponding one of the at least one variable resistance beam, said selection mechanism configured to: rotate said variable resistance beam within said containment pocket.

2. The footwear of claim 1, wherein each of said at least one containment pocket includes an open end configured to allow access to the end of the corresponding variable resistance beam.

3. The footwear of claim 1, wherein said at least one footwear module is positioned at at least one of: forward of, and aft of, an arch section of said footwear.

4. The footwear of claim 1, further comprising:
a flexible membrane joining two of said at least one footwear module.

5. The footwear of claim 1, wherein said variable resistance beam is contained within a sleeve.

6. The footwear of claim 5, wherein said variable resistance beam rotates within said sleeve.

7. The footwear of claim 5, wherein said sleeve is rotatable, said variable resistance beam being attached to said sleeve.

8. The footwear of claim 1, wherein the selection mechanism comprises one of: a cross shape, a diamond shape, a plurality of indentations and a semi-elliptical shape.

9. The footwear of claim 1, wherein said variable resistance beam is composed of high tenacity, high tensile strength materials selected from a group consisting of: plastics, thermoplastic polymers, copolymers, polyesters, vinyl chloride polymers, polycarbonate resin, metal, re-enforced plastics and nano-reinforced plastics.

10. The footwear of claim 1, wherein a cross-sectional view of said variable resistance beam is selected from a group consisting of: rectangular, elliptical, sculptured, internal spline and external spline.

11. The footwear of claim 1, further comprising:
at least one sensor, said at least one sensor attached to at least one of: said anchor plate and at least one of said at least one variable resistance beams.

12. The footwear of claim 1, wherein the treaded section is positioned at one of: an end of the variable resistance beam and in a middle portion of the variable resistance beam.

13. The footwear of claim 1, further comprising:
a plurality of access entry points for providing access to an end of the variable resistance beam.

14. The footwear of claim 13, wherein the access entry points are positioned with one of: a side of said sole and a bottom of said sole.

15. The footwear of claim 1, wherein the variable resistance beam comprises a longitudinal shape selected from a group consisting of: cylindrical, conical and trapezoidal.

16. A footwear comprising:
an upper section; and
a sole section attached to the upper section:
two footwear modules embedded in the sole section, wherein one of the footwear modules is positioned forward of an arch section of the footwear and one of the footwear module is positioned rear of the arch section, each of the footwear modules comprise:
an anchor plate comprising:
two containment pockets, each of the containment pockets containing an internal thread; and
two variable resistance beams extending from a corresponding containment pocket in the anchor plate, wherein a threaded section of the variable resistance beam engages the internal thread of the containment pocket; and
a selection mechanism incorporated into an end of each of the variable resistance beam, said selection mechanism configured to:
rotate said variable resistance beam within said containment pocket.

17. The footwear of claim 16, further comprising:
a plurality of access entry points for providing access to an end of each of the variable resistance beams, wherein the access entry points are positioned with one of: a side of said sole section and a bottom of said sole section.

18. The footwear of claim 16, further comprising:
a flexible membrane joining said two footwear modules.

19. The footwear of claim 16, wherein the variable resistance beam comprises a longitudinal shape selected from a group consisting of: cylindrical, conical and trapezoidal.

20. The footwear of claim 16, wherein a cross-sectional view of said variable resistance beam is selected from a group consisting of: rectangular, elliptical, sculptured, internal spline and external spline.

* * * * *